US008766034B2

(12) United States Patent
Shih et al.

(10) Patent No.: US 8,766,034 B2
(45) Date of Patent: Jul. 1, 2014

(54) TL1A MODEL OF INFLAMMATION FIBROSIS AND AUTOIMMUNITY

(75) Inventors: David Q. Shih, Los Angeles, CA (US); Stephen R. Targan, Santa Monica, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 13/240,117

(22) Filed: Sep. 22, 2011

(65) Prior Publication Data

US 2012/0079611 A1 Mar. 29, 2012

Related U.S. Application Data

(60) Provisional application No. 61/431,809, filed on Jan. 11, 2011, provisional application No. 61/385,273, filed on Sep. 22, 2010.

(51) Int. Cl.
*A01K 67/00* (2006.01)

(52) U.S. Cl.
USPC .......... 800/9; 800/8; 800/13; 800/18

(58) Field of Classification Search
CPC ............. A01K 2267/0325; A01K 2267/0387; A01K 2227/105; A01K 2227/05
USPC ....................................... 800/8, 9
See application file for complete search history.

(56) References Cited

U.S. PATENT DOCUMENTS

| | | | |
|---|---|---|---|
| 6,215,040 B1* | 4/2001 | Lee et al. ............ | 800/18 |
| 7,060,869 B2* | 6/2006 | Tsien et al. .......... | 800/18 |
| 7,368,527 B2 | 5/2008 | Rosen et al. | |
| 2002/0198371 A1 | 12/2002 | Wang | |
| 2003/0198640 A1 | 10/2003 | Yu et al. | |
| 2004/0013655 A1 | 1/2004 | Shiozawa et al. | |
| 2007/0037165 A1 | 2/2007 | Venter et al. | |
| 2008/0293582 A1 | 11/2008 | Li et al. | |
| 2010/0190162 A1 | 7/2010 | Rotter et al. | |
| 2010/0240043 A1 | 9/2010 | Rotter et al. | |
| 2012/0053131 A1 | 3/2012 | Rotter et al. | |

FOREIGN PATENT DOCUMENTS

| | | |
|---|---|---|
| WO | WO 2006/075254 | 7/2006 |
| WO | WO 2008/106451 | 9/2008 |
| WO | WO 2008/109782 | 9/2008 |
| WO | WO 2009/052512 | 4/2009 |
| WO | WO 2010/075579 | 7/2010 |

OTHER PUBLICATIONS

Hsu et al. J Immunol 2005;175:5153-45.*
Bamias et al. PNAS 2006;103:8441-6.*
Hörnquist et al. J Immunol 1997;158:1068-77.*
Shih, G.Q. et al., Constitutive TL1A (TNFSF15) Expression on Lymphoid or Myeloid Cells Leads to Mild Intestinal Inflammation and Fibrosis, PLOS One, Jan. 2011, 6(1): 1-16.
Shih, D.Q. et al., Microbial Induction of Inflammatory Bowel Disease Associated Gene TL1A (TNFSF15) in Antigen Presenting Cells, NIH-PA Author Manuscript (20 pgs), published as Eur J. Immunol. Nov. 2009; 39 (11):3239-3250.
Takedatsu, H. et al., IL1A (TNFSF15) Regulates the Development of Chronic Colitis By Modulating both T helper ((Th)1 and Th17 Activation, NIH-PA Author Manuscript (39 pgs), published as Gastroenterology, Aug. 2008; 135(2) (2):552-567.
PCT/US2008/055020 International Search Report and the Written Opinion dated Aug. 14, 2008, 10 pages.
Yamazaki et al., Single nucleotide polymorphisms in TNFSF15 confer susceptibility to crohn's disease. Human Molecular Genetics 2005, 14(22):3499-3506.
Wen et al., TL1A-induced NF-kB activation and c-IAP2 production prevent DR3-mediated apoptosis in TF-1 cells. The Journal of Biological Chemistry, 2005, 278(40): 39251-39258.
PCT/US2008/055020 International Preliminary Report on Patentability dated Aug. 26, 2009, 6 pages.
Aggarwal, B.B. et al., The role of TNF and its family members in inflammation and cancer: Lessons from gene deletion, Curr. Drug Targets Inflamm. Allergy, Dec. 2002, 1(4):327-341.
Ghosh et al., Anti-TNF therapy in Crohn's disease, Novartis Foundation Symposium, 2004, vol. 263:193-210.
Mascheretti et al., Pharmacogenetic investigation of the TNF/TNF-receptor system in patients with chronic active Crohn's disease treated with infliximab, The Pharmacogenomics Journal, 2002, 2:2, pp. 127-136.
Plevy et al., A role for TNF-alpha and mucosal T helper-1 cytokines in the pathogenesis of Crohn's disease, The Journal of Immunology, 1997, 159(12): 6276-6282.
Shetty et al., Pharmacogenomics of response to anti-tumor necrosis factor therapy in patients with Crohn's disease, American Journal of Pharmacogenomics, 2002, 2(4):215-221.
U.S. Appl. No. 12/528,055 Restriction Requirement dated Apr. 6, 2011.
U.S. Appl. No. 12/528,055 Non-Final Office Action dated Jun. 27, 2011.
Leong et al., NOD2/CARD15 gene polymorphisms and crohn's disease in the Chinese population. Aliment Pharmacol Ther 2003, vol. 17:465-1470.
Ogura et al., A frameshift mutation in NOD2 associated with susceptibility to crohn's disease. Nature 2001, 411:603-606.
Yamazaki et al., Absence of Mutation in the NOD2/CARD15 Gene among 483 Japanese patients with crohn's disease. Journal of Human Genetics 2002, 47:469-472.

(Continued)

*Primary Examiner* — Janice Li

(74) *Attorney, Agent, or Firm* — Sean D. Senn; Nixon Peabody LLP

(57) ABSTRACT

This invention relates transgenic animals that overexpress TL1A in a tissue specific manner to model inflammatory bowel disease (IBM such as colitis, Crohn's disease and ulcerative colitis, fibrosis, and related inflammatory diseases and conditions. TL1A transgenic animals constitutively express both TL1A and GFP in lymphoid and myeloid cell lineages, allowing convenient identification and sorting of immune cells involved in IBD disease progression, such as T-cells, antigen presenting cells (APC), and dendritic cells (DC). TL1A transgenic animals may be induced to exhibit gross fibrosis, or isolated cells may be implanted into immunodeficient mice to establish colitis.

18 Claims, 71 Drawing Sheets

(56) References Cited

OTHER PUBLICATIONS

U.S. Appl. No. 12/528,055 Final Office Action dated Mar. 27, 2012.
PCT/US2008/080526 International Search Report and the Written Opinion dated Mar. 25, 2009, 11 pages.
PCT/US2008/080526 International Preliminary Report on Patentability dated Apr. 20, 2010, 6 pages.
U.S. Appl. No. 12/675,718 Restriction Requirement dated Aug. 7, 2012.
Heresbach et al., NOD2/CARD15 gene polymorphisms in crohn's disease: a genotype-phenotype analysis. European Journal of Gastroenterology & Hepatology 2004, 15(1):55-62.
U.S. Appl. No. 12/675,718 Non-Final Office Action dated Feb. 6, 2013.
PCT/US2009/069531 International Search Report and Written Opinion dated Aug. 4, 2010, 12 pages.
PCT/US2009/069531 International Preliminary Report on Patentability dated Jun. 29, 2011, 7 pages.
U.S. Restriction Requirement dated Feb. 22, 2013.

* cited by examiner

A.

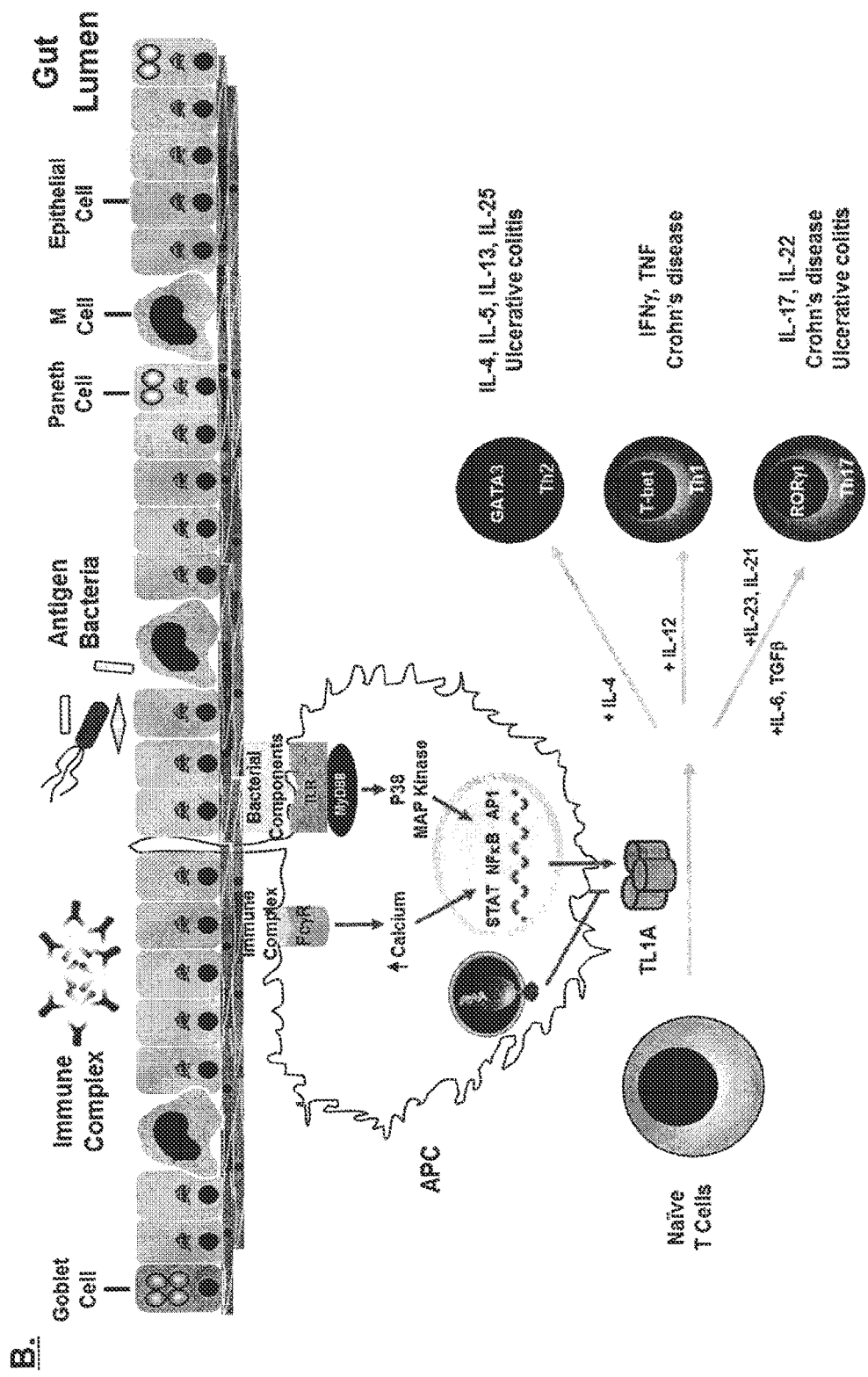

A.

B.

A.

B.

■ WT
---- L-*Tg*
— M-*Tg*

2 Months

CD11c

71%

F4/80

78%

10 Months

CD11c

72%

F4/80

70%

*GFP*

Figure 10

| | | Transgenic Frequency | Expected Frequency |
|---|---|---|---|
| Lymphoid Transgenic | Male | 38% (16/42) | 50% |
| | Female | 40% (15/37) | 50% |
| Myeloid Transgenic | Male | 43% (24/55) | 50% |
| | Female | 38% (20/53) | 50% |

A.

B.

A.

B.

A.

B.

A.

B.

A.

B.

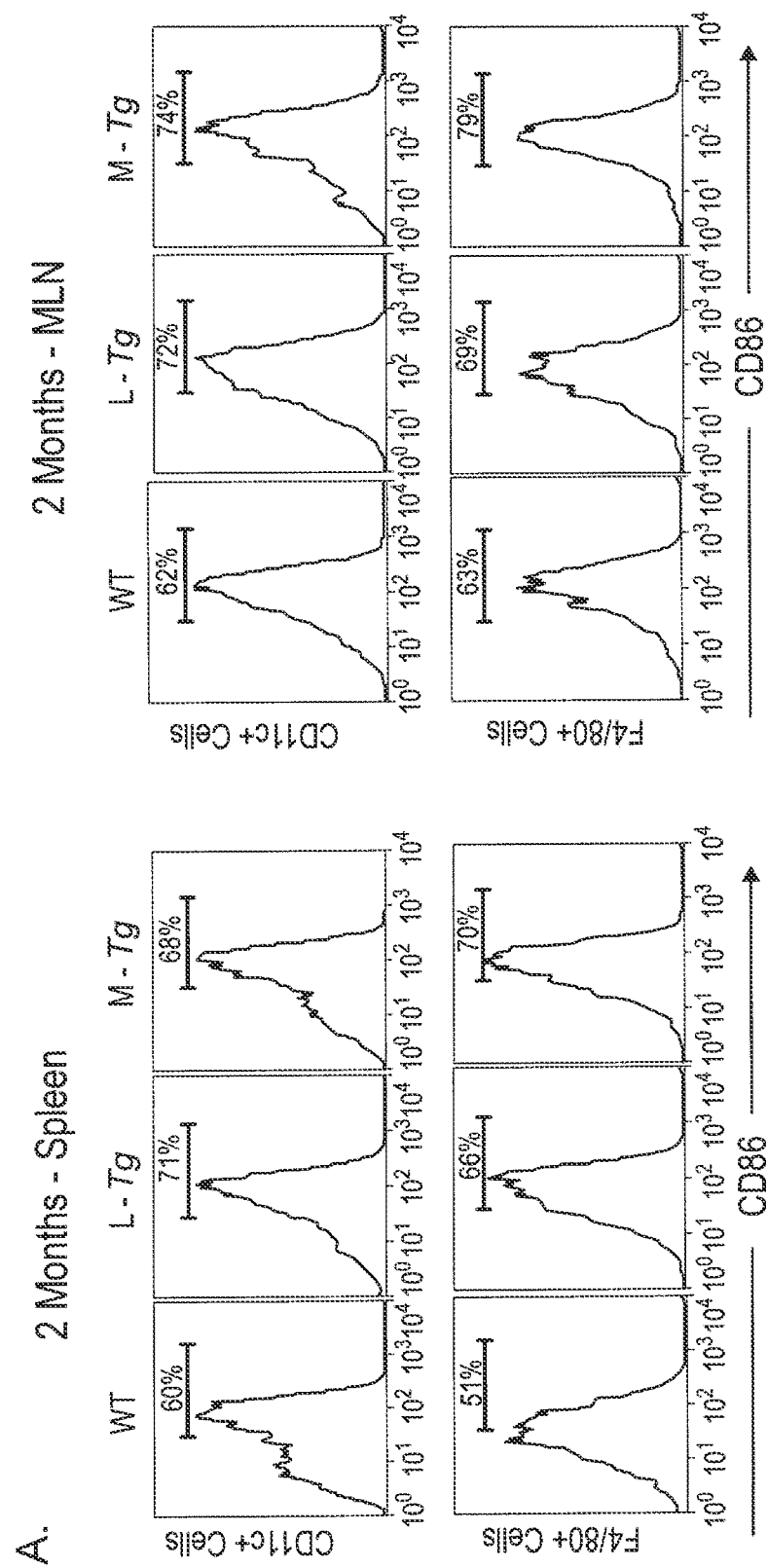

B.

A.

B.

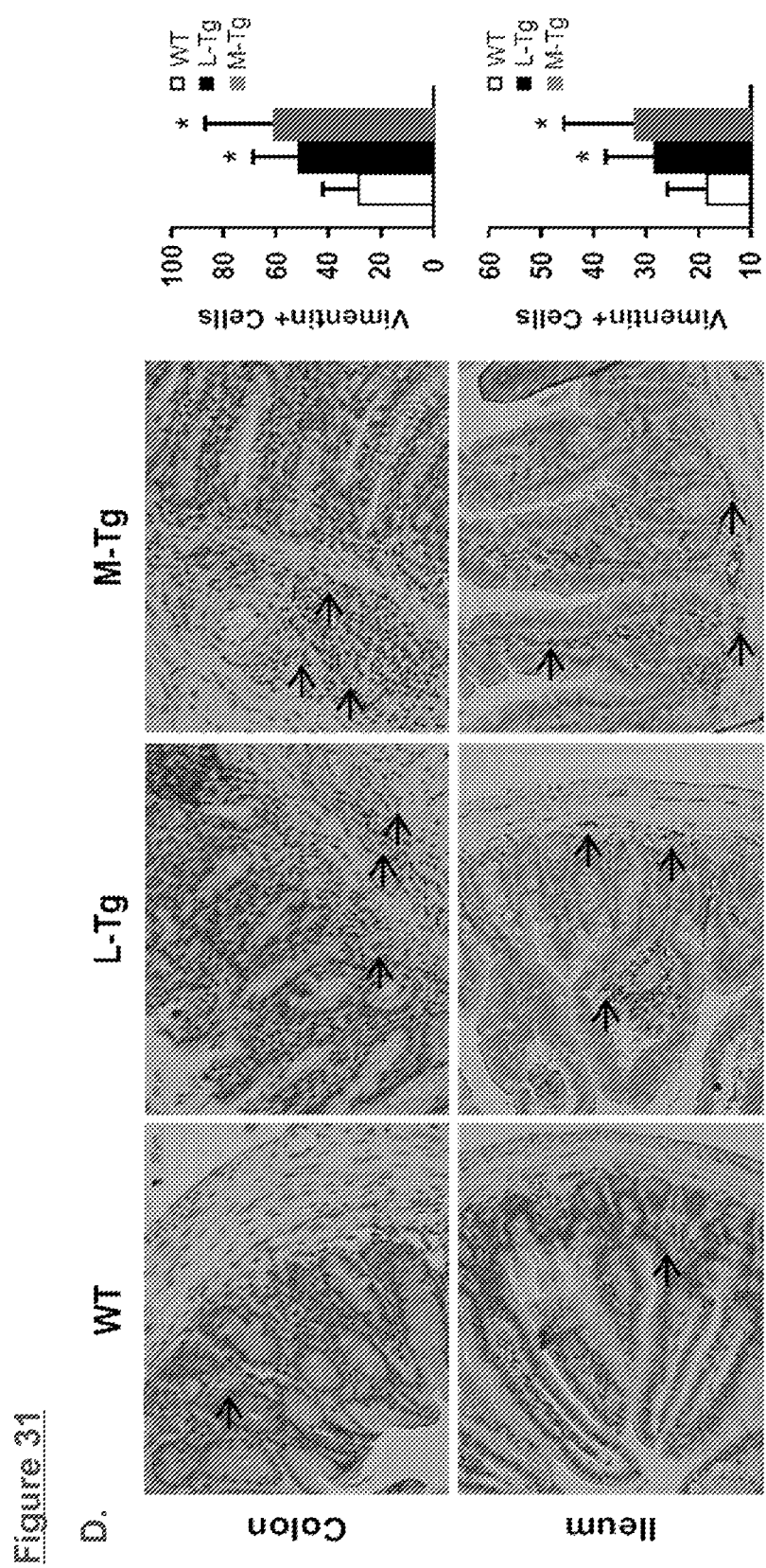

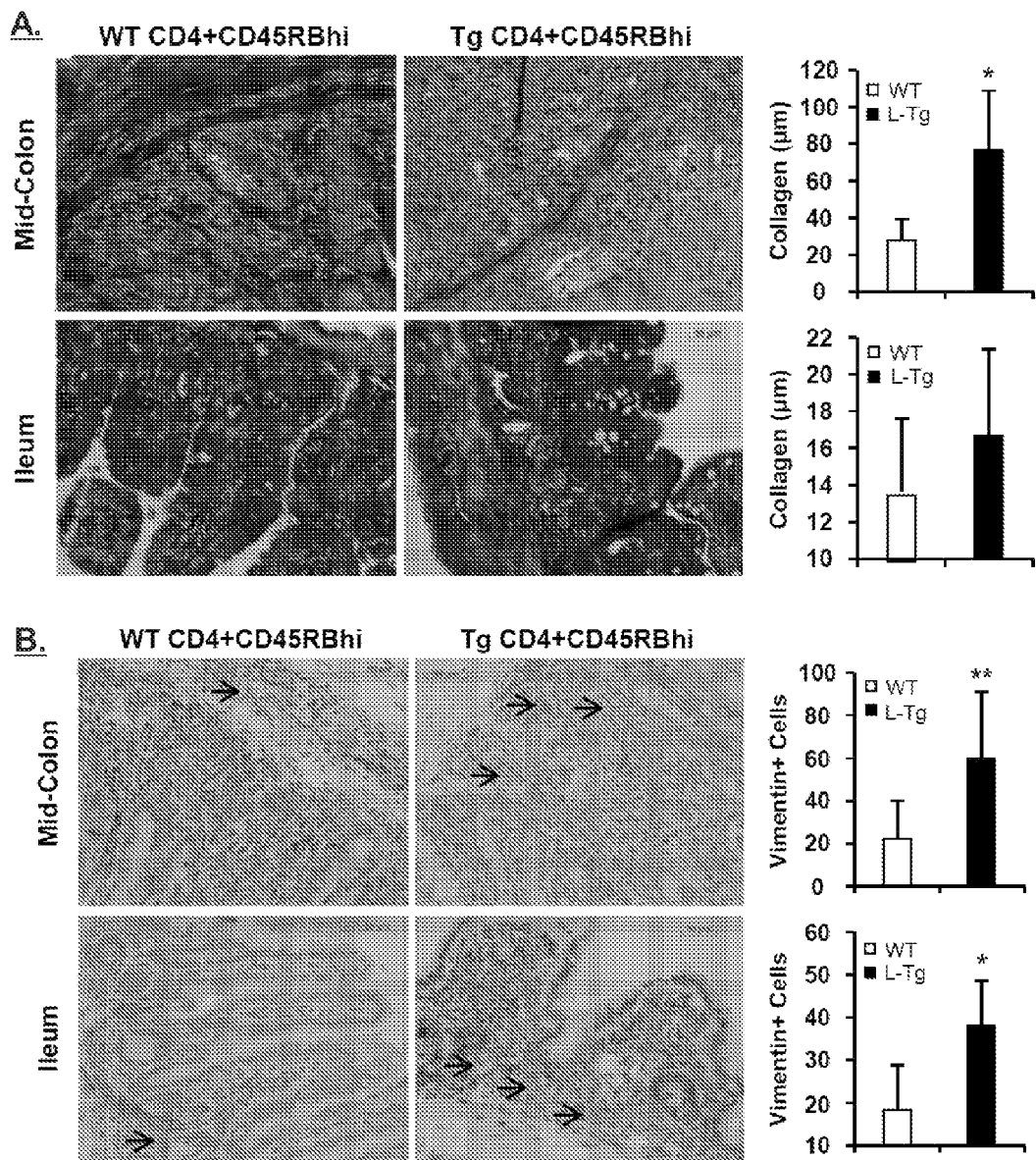

A.

B.

C.

A.

B.

C.

C.

D.

A.

B.

A.

B.

SEQUENCE LISTING

<160> NUMBER OF SEQ ID NOS: 11

<210> SEQ ID NO 1
<211> LENGTH: 3331
<212> TYPE: DNA
<213> ORGANISM: Mus musculus

```
<400> SEQUENCE: 1
aagaggtaat ccttaatggg gggctctctg gtcagaaggg atcagaagtc tctccaagac      60
agcagaagga tggcagagga gctggggttg ggcttcggag aaggagtccc agtggaagtg     120
ctgccggaag gctgtagaca caggccagag gccagggccg ggctagctgc caggagcaaa     180
gcctgcctgg ctctcacctg ctgcctgttg tcatttccca tcctcgcagg acttagcacc     240
ctcctaatgg ctggccagct ccgggtcccc ggaaaagact gtatgcttcg ggccataaca     300
gaagagagat ctgagccttc accacagcaa gtttactcac ctcccagagg caagccgaga     360
gcacacctga caattaagaa acaaacccca gcaccacatc tgaaaaatca gctctctgct     420
ctacactggg aacatgacct agggatggcc ttcaccaaga acgggatgaa gtacatcaac     480
aaatccctgg tgatcccaga gtcaggagac tatttcatct actcccagat cacattccga     540
gggaccacat ctgtgtgtgg tgacatcagt cggggagac gaccaaacaa gccagactcc      600
atcaccatgg ttatcaccaa ggtagcagac agctaccctg agcctgcccg cctactaaca     660
gggtccaagt ctgtgtgtga aataagcaac aactggttcc agtccctcta ccttggggcc     720
acgttctcct tggaagaagg agacagacta atggtaaacg tcagtgacat ctccttggtg     780
gattacacaa aagaagataa aactttcttt ggagcttttct tgctataagg aggagaaaac     840
catcattcca aggggctccc ctgcctccta cttttccaatt tccttttctc atatggatct     900
ataaacaggg gctttagagg gatcagggaa ggggacagtg gtttagctat ataatttagg     960
aacccaatat tgatccgtat atgccttatg gactaaaata gtaaatggaa acccagtac    1020 agctcatgtt tgatagagac ctgctgggtt ttaaaaattg aaacacgcct catccaatgg    1080
cacaatctac tgatttcagg acagaaccct tccacagtgc cctctgtcca gtccttttct    1140
gaattcagca gttcagttag agctgaattc gacaatgaac ttactccaga tcaagagcta    1200
aagacagaat ccaaagaaag actgagaaaa tgatgttatt tctccaagag gcaatgcatt    1260
tccacattct tttgtgccta acctaaaaaa taagaaagaa gaaaggaagg aaggaaggaa    1320
ggaaggaagg aaggaaggaa ggaaggaagg aaggaaggaa ggaaggaagg gacaagaaaa    1380
gacaagacaa gacaagaaaa aagaaaaaat ggtatttctc gtgaatattc cctaaaagga    1440
attggttttc tgctgtgaag gagaaacctc acctttcttc tgattgcatc ctttagtatc    1500
caaacataca agtgggaatt ccaaatgcac atggaacata gaacactttt attattgtga    1560
gaacatgttt attgagtacc tactatgctc tgggcactca gcccacagga ccatgaagag    1620
aaagtcaaat tttcttaaaa actaaatgaa tcctcaatac atacttcctg atcaactacc    1680
actcaaaatg tataacttcc aaagtataac ttcaagtcag ccatctaggt ggtttcttgg    1740
gtaaaggtgc ttgtcattaa gcctgacacc tgggtttgac ctcccagaac ccaaaagctg    1800
gaaggagaga attggttccc acaaattatc ctcaaacccc catacaaatg atgtggcatg    1860
cacacatgta actaaataaa taagtgtaaa acaaaaacaa aaacaaaatt ttaaagaaaa    1920
atttcaagtc ctgaaagaca gcattcctga gaatgttgtc tccatcgttg tccagtatag    1980
gctaaccagc tgatagagac actgaaggaa tttaaagaca gacatcaagt gaaatggagc    2040
actgtagaaa cacttgattc atgccaggag tcaatgtact atgaagacca acaacaaagt    2100
gtcagtcatc aaatccagag gtgtttatct agatctgctt tcaagtttgg tttgcagcct    2160
ttatatagtc tctattacaa atgctcgtgt catggtagat gccacaagga gtcagggggt    2220
aaacttagcc ccaaaccact gctgagccat cttctaggaa accttcgaag cagagctggg    2280
cagcgtgact cccacacaat gactgggaaa gtagtagctg atcaaaattt gttgagtaat    2340
```

-continued

```
aatttgttag aaaattcatc tccactgcct actaaaccta agttgtatac tatctagctt    2400
ctgctaagcc aacttacatt ggccactttt tctgtcttca acttcttgaa gtatcacagg    2460
tctcagtgag aacacaggga aaggtgaggt cgccttcccc tggttcttca tagggggaaac   2520 cacacctgaa agaagatgag cagcctgagg tgacctggag gaagggctgt ctcagaagaa    2580
ggacttattt tttggcttag gtctaaaacc ttgagagtaa tgctcactgg tcaattgagg    2640
atgctttatc aatgactcca gtctgactcc aaggtcagaa aggagagtga gatgctctct    2700
ctgcctgcat atatcttcat ggaacatgag aatattgagc aacatagact tataggaaaa    2760
cacttgccca aaagtagcca gagtaacctg gtcatcccct ctactaaacc caagctttgt    2820
gtcaagggcc ttcaaagctg cccagaagtg atctggatgg cttgggaatt tatccaagac    2880
aggaatttcc tgacagccaa agatgcttga gtccttgtgc ctgacatgca tttattttgc    2940
ccctgtttat tgaagactgt aactgttgat ttgtgggtat acatacatac atacatacat    3000
acatacatac atacatacat atgctgtcat gaaggcagca tcaaacatta ctaattggac    3060
tcaaaccagc atttctgttt ccaagatact aagtattccc atgcaaacag gagcatgcta    3120
tttttctaaa gcaaaatgaa aaaaatagtt ttgaaagtat atatatgatg gagtcaagtg    3180
taatggcata catctgtaaa cccagcacat gggatgctga gccaggagga tcgccgtgag    3240
tttgaggaga acaggggcta aatagtaatt ttcaggaaag ccttgcctat ataacaagac    3300
cttgtctcaa atgaaaaaaa aaaaaaaaaa a                                   3331
```

<210> SEQ ID NO 2
<211> LENGTH: 39
<212> TYPE: DNA
<213> ORGANISM: Mus musculus

<400> SEQUENCE: 2

```
aatggggcg cgccgggctc tctggtcaga agggatcag                              39
```

<210> SEQ ID NO 3
<211> LENGTH: 39
<212> TYPE: DNA
<213> ORGANISM: Mus musculus

<400> SEQUENCE: 3

```
tttacgggcg cgccccttaa gatacattga tgagtttgg                             39
```

<210> SEQ ID NO 4
<211> LENGTH: 25
<212> TYPE: DNA
<213> ORGANISM: Mus musculus

<400> SEQUENCE: 4

```
gactaacaaa gatgcctgcc tgtgg                                            25
```

<210> SEQ ID NO 5
<211> LENGTH: 24
<212> TYPE: DNA
<213> ORGANISM: Mus musculus

<400> SEQUENCE: 5

```
gccatccttc tgctgtcttg gaga                                             24
```

<210> SEQ ID NO 6
<211> LENGTH: 23
<212> TYPE: DNA
<213> ORGANISM: Mus musculus

```
<400> SEQUENCE: 6
ttggaagctg attgaagggt cca                                              23

<210> SEQ ID NO 7
<211> LENGTH: 23
<212> TYPE: DNA
<213> ORGANISM: Mus musculus

<400> SEQUENCE: 7
agctcctctg ccatccttct gct                                              23

<210> SEQ ID NO 8
<211> LENGTH: 6705
<212> TYPE: DNA
<213> ORGANISM: Homo sapiens

<400> SEQUENCE: 8
ggaaaaggga aggaggagac tgagtgatta agtcacccac tgtgagagct ggtcttctat      60
ttaatggggg ctctctctgc ccaggagtca gaggtgcctc caggagcagc aggagcatgg     120
ccgaggatct gggactgagc tttggggaaa cagccagtgt ggaaatgctg ccagagcacg     180
gcagctgcag gcccaaggcc aggagcagca gcgcacgctg gctctcacc tgctgcctgg      240 tgttgctccc cttccttgca ggactcacca catacctgct tgtcagccag ctccgggccc     300
agggagaggc ctgtgtgcag ttccaggctc taaaaggaca ggagtttgca ccttcacatc     360
agcaagttta tgcacctctt agagcagacg gagataagcc aagggcacac ctgacagttg     420
tgagacaaac tccacacag cactttaaaa atcagttccc agctctgcac tgggaacatg      480
aactaggcct ggccttcacc aagaaccgaa tgaactatac caacaaattc ctgctgatcc     540
cagagtcggg agactacttc atttactccc aggtcacatt ccgtgggatg acctctgagt     600
gcagtgaaat cagacaagca ggccgaccaa acaagccaga ctccatcact gtggtcatca     660
ccaaggtaac agacagctac cctgagccaa cccagctcct catggggacc aagtctgtat     720
gcgaagtagg tagcaactgg ttccagccca tctacctcgg agccatgttc tccttgcaag     780
aaggggacaa gctaatggtg aacgtcagtg acatctcttt ggtggattac acaaaagaag     840
ataaaacctt ctttggagcc ttcttactat aggaggagag caaatatcat tatatgaaag     900
tcctctgcca ccgagttcct aattttcttt gttcaaatgt aattataacc aggggttttc     960
ttggggccgg gagtaggggg cattccacag ggacaacggt ttagctatga aatttgggc     1020 ccaaaatttc acacttcatg tgccttactg atgagagtac taactggaaa aaggctgaag    1080
agagcaaata tattattaag atgggttgga ggattggcga gtttctaaat attaagacac    1140
tgatcactaa atgaatggat gatctactcg ggtcaggatt gaaagagaaa tatttcaaca    1200
ccttcctgct atacaatggt caccagtggt ccagttattg ttcaatttga tcataaattt    1260
gcttcaattc aggagctttg aaggaagtcc aaggaaagct ctagaaaaca gtataaactt    1320
tcagaggcaa atccttcac caattttttcc acatactttc atgccttgcc taaaaaaaat    1380
gaaaagagag ttggtatgtc tcatgaatgt tcacacagaa ggagttggtt ttcatgtcat    1440
ctacagcata tgagaaaagc tacctttctt ttgattatgt acacagatat ctaaataagg    1500
aagtatgagt ttcacatgta tatcaaaaat acaacagttg cttgtattca gtagagtttt    1560
cttgcccacc tattttgtgc tgggttctac cttaacccag aagacactat gaaaacaag     1620 acagactcca ctcaaaattt atatgaacac cactagatac ttcctgatca acatcagtc     1680 aacatactct aaagaataac tccaagtctt ggccaggcgc agtggctcac acctgtaatc    1740
```

-continued

```
ccaacacttt gggaggccaa ggtgggtgga tcatctaagg ccgggagttc aagaccagcc    1800
tgaccaacgt ggagaaaccc catctctact aaaaatacaa aattagccgg gcgtggtagc    1860
gcatggctgt aatcctggct actcaggagg ccgaggcaga agaattgctt gaactgggga    1920
ggcagaggtt gcggtgagcc cagatcgcgc cattgcactc cagcctgggt aacaagagca    1980
aaactctgtc caaaaaaaaa aaaataaaat aataactcca agcctttaaa aatatcatc    2040
tgaaactgtt acatcagatt tctggcactc tactgactgt ggaagatagc cagctgactg    2100
gaagatagcc agctgattag ttccctgaag aaacctgaag acagatacct ggttaactag    2160
atcaactaca ctgccaactt gtttgatgct gagagacaat ggacttattc catgggggaa    2220
gggaaaaaag aagtcaatca ccaaatctga agaagttaac ctagatcttt gaggtttgat    2280
ttgcaacttt atatgcagag tattatgtgg gtattttccc ttaaaatatt caagggatt    2340
tacatatggg attagctaat gagcctagcc aagaccttcc ctggaggaca ggctggtcat    2400
tgcggaggtc ccttctgtgc ttcagtgggt tcatatcctc tagtccgtat gattttccta    2460
cgctaatatg tcaagggcag gagaggcagc tctgttctcc tagcctttgt tgacttgtct    2520
gcaaagcagg aatctgccca tttgtttcca aggagcaaat gagctcatga gaatgaaaga    2580
tgttaacttc atgcattctg tgccatctga gcatttcggt attatatgac tggtgaccct    2640
tggcccgtat tataaatgct tcctatcctg ggagacctca tggatgagtc tgagaggaaa    2700
tttggcacca aaatcactct cactctggtt tccagtagac tatagaggca gagaggcatt    2760
tgagaggctc ctgagcaaag tgtccagtgt agcaggagca cttcattaat atttattgag    2820
ttataattaa ataaaaatta atttctgatt tctcagtttg gaggttaagg ctctaaatat    2880
attttctaac ctctgctagg ctaacttaag ccaggccttt ttcttgcctt ccctttctca    2940
aaacagtcag cacagactca gtgggagcac agaggagtgt ggtcacctcc acctggctca    3000
ccagagtctt catagaggaa gtgaagcctg gaagaaactg ggcgggcccc agatgaccac    3060
agggaagg catctcagat ggaggaatta cccttgactt aaagcagaaa agaaagattt    3120
ctcagtaact ccaaaacttg cttgatagga gaatattccc tcaaccaatt cctaggacaa    3180
tatttattgg tagatcaaga atgtttcctc aataactcta gtctagctcc atgatcagaa    3240
ctaacaccca ttaaaaacat aaaatgttct ttctgaaccg gtcttcatgg tgcgtgagag    3300
caccaagcag cttttggtatg caggaggagt tttgcacaga agagtggcct gctcaaacct    3360
gcccactgtt ctgtaggtga tctggtggat ctggaaattt atcccaagac aggaatttcc    3420
taatattcga agacatttga ggctttggga aattctctgc tgtgcattta tttggctcct    3480
gtcataagct tgttttttaa agaatgtatc atagctcaag tttttactgc tgattttgtt    3540
aaattctgta tagtatattt tttacggaaa ggcacagtca gacattccta ataggctca    3600
tgtcagaact tctgttccca aggcattatc tccatagcaa aaattagtgc actgttttca    3660
aaagtgaggt gggaaaatgc ttttaagatc atgtgatgtt cccctaaaag gggttaatgg    3720
ggtgtattca gggtttggga gggaggaaga agcatgcttt agaaaacagt aaatttaggg    3780
agaaaatgct ttgttggtta aatgtcactc aaaaggctga attcaaatca attccacaaa    3840
catttactga gtacctactg cccctgggga cacagagata aattatttag tctcagacac    3900
actcattcta acttcccagc acctctactg tctgcagatt cttttaattta ttttggttgt    3960
attagctaat taattcgtaa actttaggca catggatcta ttctcattat gaaaatggat    4020
gccatttgat taaggctgat gactaacaaa atgatttgtg tttactcgaa gtgttttttt    4080
aaaaatagct actcaaggat agttttccat aaatcaagaa ggtaaaaaag ttcccatttt    4140
```

```
ttattgtaga atccattatt taaactacat gtagagacag gttattattt gctatattca      4200
agtttggtca tcaatacccct taaaaatatt agaattttat ggatgaccca gaaatgcttt      4260
gaaaatctgt gttcctcagc aaatacagag accatgatca aaatgcacag aatcactaac      4320
attttgatgc tagcatggtt tcagtctatt tggcagaaca gaattgatta tgctactaaa      4380
attctttttt cttttttttt tttttttttt ttgagacaga gtcttgcttt gtcacccagg      4440
ctgaagtgca gtggcaggat ctcagttcac tgcaacctct gcctcccagg ttcacgccat      4500
tctcctgctt cagcctcccg agtagctggg actacaggct cccaccacca tgcccggcta      4560 atttttttgca ttttagtag agacggggtt tcaccgtgtt agccaggatg gtctcgatct      4620
cctgacctcg tgatccgccc gcctcagcct tccaaagtgc tgggattaca ggcgtgagcc      4680
actgtgcccg gactctgatt tttttttac taaggtacag taagaaaagg gaaagtgta      4740 cgttttcact tcctgaaata tgtcaggttg aatcaataat agagcacacc agaactcttg      4800
gctccatttc aacctaaact attcagttct catcacccca gaggaaattc cgcctctgtg      4860
ctggtcagta atcccctgg attataaaag tttaactaac tcactgtgca caaggcacgg      4920
ccattgccaa cattctcttg caaggtattt tcccaagccc ttacccaatt ctgttccat      4980 gattgtgaca ttggggatta attctgcaag acagaactgt ttatattctg taccttaaaa      5040
acacatgcaa acatctcttg ccttaagatt tctggctttc ctatggccca gagtcctaga      5100
agtgttttga tatttgtagc agaattttca agtgtacatc cttatcctgg atattaacat      5160
ttttgcatca tattggcagc tggacctaca gagaatttag tagactgtta acctaataag      5220
ccttgaatcc ttttgcacca gtggtgagag aatgtggatc agagccatca cctccatgcc      5280
ccgtcaccct ctaacaacca catttacaac ttccccagct ctgagacaca cttgcctcca      5340 cccttccat caccccattt taagatgaaa ataccacacc agcctggaag gaagaagtta      5400
cttgcccagg gccacatagt gagttaaggg ctgatctaga gctaggaagc tgtcttcctg      5460
aaccataatc ctggactctt ctaacctctc tactcatcgc aaatagagtt cattttagtg      5520
atttgaagga agatgggaca agtattttca aacacctgta ggacaacatg gaagtgggag      5580
gagacttcta ctgtagctcc ccagagaaga gagctagggc tacagagttg cagttacaag      5640
gttgccctct ctggcttgat ccccaaagga attttctact ccaaaataga atttttctag      5700
gatgctattt ctcagtccct ggagatactc aaacaaaggg cttgtcacaa gggttttgt      5760 agaagctatt cttcacagag gttggggag agattaagcc aaaggatctc tgaggtcttt      5820
ttcaaatcta taattatgtg gccttttgtt cattgacttc catgtgttct agttgatcat      5880
tacaaacctg gcaggccttc tcaagggttc agtaattagc tgtcatttcc catttgtcca      5940
gagagtgtcc aacacaaaat acccctaaga tcttggccaa tagagaaatg tcatggaatt      6000
ttagaaatga cagtatctgc ggagtttatt ccaagttata tcatttcaaa gatgaagaaa      6060
cccaggctca gagggagcca tcacatccac accctgtcac ccttcgtggc cagtgccaga      6120
cagtagctag ttggatgcta aaagtagaat ttagatatct taacaataag cccagcagtc      6180
tttcaacttc attcgtaaat cattttttgtt ttgagcatct gtcacgtggc agcacttgcc      6240
tggatactgg agagctgaga aggaatgcga caggcaagtc ctactctcac agtgtataca      6300
ttcaggagga acaagacaca cagtgccaag taaataaagt agctgaactt catcaaatga      6360
ttttattctt aaagtcatta aagcatgtaa tgttcccctt ttttttgtttc aggggtgtac      6420 agattgaaga agtgtaggtg tttatgtggt tttagtgaca aaccccatgt gctttcattg      6480
attttatgtt ttatgttaaa acatcaaccg caaggtaaaa tgcatattgt atgttgttgg      6540
```

| | |
|---|---|
| atacgtactt aactggtatg catcccatgt ctttgggtac tagtgtatga attctaatct | 6600 |
| ctgtaaatga aatgttgtat gtgttaatat atttaataga tgtaacttaa taaactggca | 6660 |
| ttgaagactg aagaatttc acactgtcaa aaaaaaaaaa aaaaa | 6705 |

<210> SEQ ID NO 9
<211> LENGTH: 6412
<212> TYPE: DNA
<213> ORGANISM: Homo sapiens

<400> SEQUENCE: 9

| | |
|---|---|
| atgcaactca caaagggccg tcttcatttc agtcaccctt tgtctcatac aaagcacatt | 60 |
| tctcctttg ttacagatgc acctcttaga gcagacggag ataagccaag gcacacctg | 120 |
| acagttgtga gacaaactcc cacacagcac tttaaaaatc agttcccagc tctgcactgg | 180 |
| gaacatgaac taggcctggc cttcaccaag aaccgaatga actataccaa caaattcctg | 240 |
| ctgatcccag agtcgggaga ctacttcatt tactcccagg tcacattccg tgggatgacc | 300 |
| tctgagtgca gtgaaatcag acaagcaggc cgaccaaaca agccagactc catcactgtg | 360 |
| gtcatcacca aggtaacaga cagctaccct gagccaaccc agctcctcat ggggaccaag | 420 |
| tctgtatgcg aagtaggtag caactggttc cagcccatct acctcggagc catgttctcc | 480 |
| ttgcaagaag gggacaagct aatggtgaac gtcagtgaca tctctttggt ggattacaca | 540 |
| aaagaagata aaaccttctt tggagccttc ttactatagg aggagagcaa atatcattat | 600 |
| atgaaagtcc tctgccaccg agttcctaat tttctttgtt caaatgtaat tataaccagg | 660 |
| ggttttcttg gggccgggag taggggcat tccacaggga caacggttta gctatgaaat | 720 |
| ttggggccca aaatttcaca cttcatgtgc cttactgatg agagtactaa ctggaaaaag | 780 |
| gctgaagaga gcaaatatat tattaagatg ggttggagga ttggcgagtt tctaaatatt | 840 |
| aagcacactga tcactaaatg aatggatgat ctactcgggt caggattgaa agagaaatat | 900 |
| ttcaacacct tcctgctata caatggtcac cagtggtcca gttattgttc aatttgatca | 960 |
| taaatttgct tcaattcagg agctttgaag gaagtccaag gaaagctcta gaaaacagta | 1020 |
| taaactttca gaggcaaaat ccttcaccaa tttttccaca tactttcatg ccttgcctaa | 1080 |
| aaaaaatgaa agagagttg gtatgtctca tgaatgttca cacagaagga gttggttttc | 1140 |
| atgtcatcta cagcatatga gaaaagctac ctttctttg attatgtaca cagatatcta | 1200 |
| aataaggaag tatgagtttc acatgtatat caaaaataca acagttgctt gtattcagta | 1260 |
| gagttttctt gcccacctat tttgtgctgg gttctacctt aacccagaag acactatgaa | 1320 |
| aaacaagaca gactccactc aaaatttata tgaacaccac tagatacttc ctgatcaaac | 1380 |
| atcagtcaac atactctaaa gaataactcc aagtcttggc caggcgcagt ggctcacacc | 1440 |
| tgtaatccca cactttggg aggccaaggt gggtggatca tctaaggccg ggagttcaag | 1500 |
| accagcctga ccaacgtgga gaacccccat ctctactaaa aatacaaaat tagccgggcg | 1560 |
| tggtagcgca tggctgtaat cctggctact caggaggccg aggcagaaga attgcttgaa | 1620 |
| ctggggaggc agaggttgcg gtgagcccag atcgcgccat tgcactccag cctgggtaac | 1680 |
| aagagcaaaa ctctgtccaa aaaaaaaaaa ataaaataat aactccaagc ctttaaaaaa | 1740 |
| tatcatctga aactgttaca tcagatttct ggcactctac tgactgtgga agatagccag | 1800 |
| ctgactggaa gatagccagc tgattagttc cctgaagaaa cctgaagaca gatacctggt | 1860 |
| taactagatc aactacactg ccaacttgtt tgatgctgag agacaatgga cttattccat | 1920 |
| gggggaaggg aaaaaagaag tcaatcacca aatctgaaga agttaaccta gatctttgag | 1980 |

```
gtttgatttg caactttata tgcagagtat tatgtgggta ttttccctta aaatattcaa    2040
agggatttac atatgggatt agctaatgag cctagccaag accttccctg gaggacaggc    2100
tggtcattgc ggaggtccct tctgtgcttc agtgggttca tatcctctag tccgtatgat    2160
tttcctacgc taatatgtca agggcaggag aggcagctct gttctcctag cctttgttga    2220
cttgtctgca aagcaggaat ctgcccattt gtttccaagg agcaaatgag ctcatgagaa    2280
tgaaagatgt taacttcatg cattctgtgc catctgagca tttcggtatt atatgactgg    2340
tgacccttgg cccgtattat aaatgcttcc tatcctggga gacctcatgg atgagtctga    2400
gaggaaattt ggcaccaaaa tcactctcac tctggtttcc agtagactat agaggcagag    2460
aggcatttga gaggctcctg agcaaagtgt ccagtgtagc aggagcactt cattaatatt    2520
tattgagtta taattaaata aaaattaatt tctgatttct cagtttggag gttaaggctc    2580
taaatatatt ttctaacctc tgctaggcta acttaagcca ggccttttc ttgccttccc    2640 tttctcaaaa cagtcagcac agactcagtg ggagcacaga ggagtgtggt cacctccacc    2700
tggctcacca gagtcttcat agaggaagtg aagcctggaa gaaactgggc gggccccaga    2760
tgaccacagg gaaagggcat ctcagatgga ggaattaccc ttgacttaaa gcagaaaaga    2820
aagatttctc agtaactcca aaacttgctt gataggagaa tattccctca accaattcct    2880
aggacaatat ttattggtag atcaagaatg tttcctcaat aactctagtc tagctccatg    2940
atcagaacta acacccatta aaaacataaa atgttctttc tgaaccggtc ttcatggtgc    3000
gtgagagcac caagcagctt tggtatgcag gaggagtttt gcacagaaga gtggcctgct    3060
caaacctgcc cactgttctg taggtgatct ggtggatctg gaaatttatc ccaagacagg    3120
aatttcctaa tattcgaaga catttgaggc tttgggaaat tctctgctgt gcatttattt    3180
ggctcctgtc ataagcttgt tttttaaaga atgtatcata gctcaagttt ttactgctga    3240
ttttgttaaa ttctgtatag tatatttttt acggaaaggc acagtcagac attcctaata    3300
gggctcatgt cagaacttct gttcccaagg cattatctcc atagcaaaaa ttagtgcact    3360
gttttcaaaa gtgaggtggg aaaatgcttt taagatcatg tgatgttccc ctaaaagggg    3420
ttaatggggt gtattcaggg tttgggaggg aggaagaagc atgctttaga aaacagtaaa    3480
tttagggaga aaatgctttg ttggttaaat gtcactcaaa aggctgaatt caaatcaatt    3540
ccacaaacat ttactgagta cctactgccc ctggggacac agagataaat tatttagtct    3600
cagacacact cattctaact tcccagcacc tctactgtct gcagattctt taatttattt    3660
tggttgtatt agctaattaa ttcgtaaact ttaggcacat ggatctattc tcattatgaa    3720
aatggatgcc atttgattaa ggctgatgac taacaaaatg atttgtgttt actcgaagtg    3780
tttttttaaa aatagctact caaggatagt tttccataaa tcaagaaggt aaaaaagttc    3840 ccattttta ttgtagaatc cattatttaa actacatgta gagacaggtt attatttgct    3900
atattcaagt ttggtcatca atacccttaa aaatattaga attttatgga tgacccagaa    3960
atgctttgaa aatctgtgtt cctcagcaaa tacagagacc atgatcaaaa tgcacagaat    4020
cactaacatt ttgatgctag catggtttca gtctatttgg cagaacagaa ttgattatgc    4080
tactaaaatt tctttttctt ttttttttttt ttttttttg agacagagtc ttgctttgtc    4140
acccaggctg aagtgcagtg gcaggatctc agttcactgc aacctctgcc tcccaggttc    4200
acgccattct cctgcttcag cctcccgagt agctgggact acaggctccc accaccatgc    4260
ccggctaatt ttttgcattt ttagtagaga cggggtttca ccgtgttagc caggatggtc    4320
tcgatctcct gacctcgtga tccgcccgcc tcagccttcc aaagtgctgg gattacaggc    4380
```

```
gtgagccact gtgcccggac tctgattttt tttttactaa ggtacagtaa gaaaagggaa    4440
aagtgtacgt tttcacttcc tgaaatatgt caggttgaat caataataga gcacaccaga    4500
actcttggct ccatttcaac ctaaactatt cagttctcat caccccagag gaaattccgc    4560
ctctgtgctg gtcagtaatc cccctggatt ataaaagttt aactaactca ctgtgcacaa    4620
ggcacggcca ttgccaacat tctcttgcaa ggtattttcc caagccctta cccaattctg    4680
tttccatgat tgtgacattg gggattaatt ctgcaagaca gaactgttta tattctgtac    4740
cttaaaaaca catgcaaaca tctcttgcct taagatttct ggctttccta tggcccagag    4800
tcctagaagt gttttgatat ttgtagcaga attttcaagt gtacatcctt atcctggata    4860
ttaacatttt tgcatcatat tggcagctgg acctacagag aatttagtag actgttaacc    4920
taataagcct tgaatccttt tgcaccagtg gtgagagaat gtggatcaga gccatcacct    4980
ccatgccccg tcaccctcta acaaccacat ttacaacttc cccagctctg agacacactt    5040
gcctccaccc cttccatcac cccatttttaa gatgaaaata ccacaccagc ctggaaggaa    5100
gaagttactt gcccagggcc acatagtgag ttaagggctg atctagagct aggaagctgt    5160
cttcctgaac cataatcctg gactcttcta acctctctac tcatcgcaaa tagagttcat    5220
tttagtgatt tgaaggaaga tgggacaagt attttcaaac acctgtagga caacatggaa    5280
gtgggaggag acttctactg tagctcccca gagaagagag ctagggctac agagttgcag    5340
ttacaaggtt gccctctctg gcttgatccc caaaggaatt ttctactcca aaatagaatt    5400
tttctaggat gctatttctc agtccctgga gatactcaaa caaagggctt gtcacaaggg    5460 ttttttgtaga agctattctt cacagaggtt gggggagaga ttaagccaaa ggatctctga    5520 ggtcttttte aaatctataa ttatgtggcc ttttgttcat tgacttccat gtgttctagt    5580
tgatcattac aaacctggca ggccttctca agggttcagt aattagctgt catttcccat    5640
ttgtccagag agtgtccaac acaaaatacc cctaagatct tggccaatag agaaatgtca    5700
tggaatttta gaaatgacag tatctgcgga gtttattcca agttatatca tttcaaagat    5760
gaagaaaccc aggctcagag ggagccatca catccacacc ctgtcaccct tcgtggccag    5820
tgccagacag tagctagttg gatgctaaaa gtagaattta gatatcttaa caataagccc    5880
agcagtcttt caacttcatt cgtaaatcat tttttgttttg agcatctgtc acgtggcagc    5940
acttgcctgg atactggaga gctgagaagg aatgcgacag gcaagtccta ctctcacagt    6000
gtatacattc aggaggaaca agacacacag tgccaagtaa ataaagtagc tgaacttcat    6060
caaatgattt tattcttaaa gtcattaaag catgtaatgt tccccttttt ttgtttcagg    6120
ggtgtacaga ttgaagaagt gtaggtgttt atgtggtttt agtgacaaac cccatgtgct    6180
ttcattgatt ttatgtttta tgttaaaaca tcaaccgcaa ggtaaaatgc atattgtatg    6240
ttgttggata cgtacttaac tggtatgcat cccatgtctt tgggtactag tgtatgaatt    6300
ctaatctctg taaatgaaat gttgtatgtg ttaatatatt taatagatgt aacttaataa    6360
actggcattg aagactgaag aattttcaca ctgtcaaaaa aaaaaaaaaa aa            6412
```

<210> SEQ ID NO 10
<211> LENGTH: 5828
<212> TYPE: DNA
<213> ORGANISM: Mus musculus

<400> SEQUENCE: 10

```
actcagtgtg acagctgctc tcttatttaa tgggggggctc tctggtcaga agggatcaga     60
agtctctcca agacagcaga aggatggcag aggagctggg gttgggcttc ggagaaggag    120
```

-continued

| | |
|---|---|
| tcccagtgga agtgctgccg gaaggctgta gacacaggcc agaggccagg gccgggctag | 180 |
| ctgccaggag caaagcctgc ctggctctca cctgctgcct gttgtcattt cccatcctcg | 240 |
| caggacttag caccctccta atggctggcc agctccgggt ccccggaaaa gactgtatgc | 300 |
| ttcgggccat aacagaagag agatctgagc cttcaccaca gcaagtttac tcacctccca | 360 |
| gaggcaagcc gagagcacac ctgacaatta agaaacaaac cccagcacca catctgaaaa | 420 |
| atcagctctc tgctctacac tgggaacatg acctagggat ggccttcacc aagaacggga | 480 |
| tgaagtacat caacaaatcc ctggtgatcc cagagtcagg agactatttc atctactccc | 540 |
| agatcacatt ccgagggacc acatctgtgt gtggtgacat cagtcggggg agacgaccaa | 600 |
| acaagccaga ctccatcacc atggttatca ccaaggtagc agacagctac cctgagcctg | 660 |
| cccgcctact aacagggtcc aagtctgtgt gtgaaataag caacaactgg ttccagtccc | 720 |
| tctaccttgg ggccacgttc tccttggaag aaggagacag actaatggta aacgtcagtg | 780 |
| acatctcctt ggtggattac acaaaagaag ataaaacttt ctttggagct ttcttgctat | 840 |
| aaggaggaga aaccatcat tccaaggggc tccctgcct cctactttcc aatttccttt | 900 |
| tctcatatgg atctataaac agggcttta gagggatcag ggaaggggac agtggtttag | 960 |
| ctatataatt taggaaccca atattgatcc gtatatgcct tatggactaa aatagtaaat | 1020 |
| ggaaaaccca gtacagctca tgtttgatag agacctgctg ggttttaaaa attgaaacac | 1080 |
| gcctcatcca atggcacaat ctactgattt caggacagaa cctttccaca gtgccctctg | 1140 |
| tccaagtcct ttctgaattc agcagttcag ttagagctga attcgacaat gaacttactc | 1200 |
| cagatcaaga gctaaagaca gaatccaaag aaagactgag aaaatgatgt tatttctcca | 1260 |
| agaggcaatg catttccaca ttcttttgtg cctaacctaa aaaataagaa agaagaaagg | 1320 |
| aaggaaggaa ggaaggaagg aaggaaggaa ggaaggaagg aaggaaggaa ggaaggaagg | 1380 |
| aaggaaggga caagaaaaga caagacaaga caagaaaaaa gaaaaatgg tatttctcgt | 1440 |
| gaatattccc taaaaggaat tggttttctg ctgtgaagga gaaacctcac ctttcttctg | 1500 |
| attgcatcct ttagtatcca aacatacaag tgggaattcc aaatgcacat ggaacataga | 1560 |
| acactttat tattgtgaga acatgtttat tgagtaccta ctatgctctg ggcactcagc | 1620 |
| ccacaggacc atgaagagaa agtcaaattt tcttaaaaac taaatgaatc ctcaatacat | 1680 |
| acttcctgat caactaccac tcaaaatgta taacttccaa agtataactt caagtcagcc | 1740 |
| atctaggtgg tttcttgggt aaaggtgctt gtcattaagc ctgacacctg ggtttgacct | 1800 |
| cccagaaccc aaaagctgga aggagagaat tggttcccac aaattatcct caaaccccca | 1860 |
| tacaaatgat gtggcatgca cacatgtaac taaataaata agtgtaaaac aaaaacaaaa | 1920 |
| acaaaatttt aaagaaaaat ttcaagtcct gaaagacagc attcctgaga atgttgtctc | 1980 |
| catcgttgtc cagtataggc taaccagctg atagagacac tgaaggaatt taaagacaga | 2040 |
| catcaagtga aatggagcac tgtagaaaca cttgattcat gccaggagtc aatgtactat | 2100 |
| gaagaccaac aacaaagtgt cagtcatcaa atccagaggt gtttatctag atctgctttc | 2160 |
| aagtttggtt tgcagccttt atatagtctc tattacaaat gctcgtgtca tggtagatgc | 2220 |
| cacaaggagt cagagggtaa acttagcccc aaaccactgc tgagccatct tctaggaaac | 2280 |
| cttcgaagca gagctgggca gcgtgactcc cacacaatga ctgggaaagt agtagctgat | 2340 |
| caaaatttgt tgagtaataa tttgttagaa aattcatctc cactgcctac taaacctaag | 2400 |
| ttgtatacta tctagcttct gctaagccaa cttacattgg ccactttttc tgtcttcaac | 2460 |
| ttcttgaagt atcacaggtc tcagtgagaa cacagggaaa ggtgaggtcg ccttcccctg | 2520 |

```
gttcttcata ggggaaacca cacctgaaag aagatgagca gcctgaggtg acctggagga    2580
agggctgtct cagaagaagg acttatttt tggcttaggt ctaaaacctt gagagtaatg    2640
ctcactggtc aattgaggat gctttatcaa tgactccagt ctgactccaa ggtcagaaag    2700
gagagtgaga tgctctctct gcctgcatat atcttcatgg aacatgagaa tattgagcaa    2760
catagactta taggaaaaca cttgcccaaa agtagccaga gtgacctggt catcccctct    2820
actaaaccca agctttgtgt caggggcctt caaagctgcc cagaagtgat ctggatggct    2880
tgggaatttta tccaagacag gaatttcctg acagccaaag atgcttgagt ccttgtgcct    2940
gacatgcatt tattttgccc ctgtttattg aagactgtaa ctgttgattt gtgggtatac    3000
atacatacat acatacatac atacatacat acatacatat gctgtcatga aggcagcatc    3060
aaacattact aattggactc aaaccagcat ttctgtttcc aagatactaa gtattcccat    3120
gcaaacagga gcatgctatt tttctaaagc aaaatgaaaa aaatagtttt gaaagtatat    3180
atatgatgga gtcaagtgta atggcataca tctgtaaacc cagcacatgg gatgctgagc    3240
caggaggatt gccgtgagtt tgaggagaac aggggctaaa tagtaatttt caggaaagcc    3300
ttgcctatat aacaagacct tgtctcaaat gaaaaaaaa aaaaaaatag accccaggct    3360
ggtccttgga gataaggtaa tatattcatt gggtgagggg gtgtgtgttt tggaaaaatag    3420
ttaatttagt gagaaatgct tttcggtcaa atgcatctca aaggctgctg aattcaaatc    3480
gggtctgtaa atgcttacct agtgcttgct tgccctgggg acagagacat aaattacttt    3540
agtctcagat ccactcgttc taacagattg gcatctccat cgtctgtgga gcttttaatc    3600
actctgtttg tattagctaa ttaattagct aacttgagac acactgatat tttcttatta    3660
taaacatggg tgccatttga taaaagacaa tcattaacaa aatggttcga atttccgctt    3720
aagtgatctt cttttttcct tttcatttt tttaactagc taatcaaagg tagtttccca    3780
aaaataaatg caagggagt ataagaaaa aattccctgt ggtgggagct agtattgaaa    3840
caacagtatc aaagaggctg ttacctactg gcctcaaatt ttggcaggaa cgcctttgaa    3900
aatgttagaa ctttacggac agcctagagg tgctttgaaa agtctctgtt gccaacaaaa    3960
gccattaatc agcatgcggc acaggttact caaattttga ccttgactgt tttttagatc    4020
tgttacacag aacacaactt ctgggctgta atctctgatg tggatttggt gatttactaa    4080
ggtaccgtgg gaaacaagga aagtgtactt gtaccacatc gtttctcagt gcatgtcaga    4140
gtctactcaa cagcagggca tgccagagcc ttggatacat tccgggacaa actatgtcac    4200
tcctaaggaa attccaagtg tgtgcctgtc aagcactctg gatcatagaa gcccacgagt    4260
tcactgtgca caaggcacag ccatggccag cactctcttg catggtattt ctcttaagct    4320
cttactcaat cacggtccca tgattgtgac attggggatt aattgcttga gcaggtttat    4380
ttacagtctg ttccttgcaa aatacatgca gatatgtctg gcctcaaaat cccctgattg    4440
ttttagggct tagagaatac tggggatgtt tttgctgttt tcagatgtac tttatttaag    4500
cttgcagaat taccctgaat attaacagtg ttctaagata ttgcctgcta gcttctggct    4560
aatttactag tggtgacagt atcagatcag agtatctata tttatgtctt gctattatag    4620
ttaaaacttc ctgatctctg taacacactc accctacct catctatcta cccatcttgt    4680
ggatgtagct gtgagaagac tcacaagccc gagttgcagt tacttttctg aagcaacata    4740
gtatgttaat ggaatggcca gaactctact cttggcacat ggcactgaat tgatgccac    4800
taaaagaaaa attgaaggca gaaatatttt ttactatgca tgggacaacg tagaagagca    4860
aggagactgc ttacacatgg tggtcacatc tctggcttca tccctaaacc aatttttctga    4920
```

```
cccaagtcg atttttttc atgtagttat tgttcattt ctggaaagag tcaagcaaaa      4980
agagagtttt atagaaacca ttgcatcatg gaggtcaggg gagggattaa gccaaagaat   5040
tccttctcca atctatagc catatggcca cccctttggtg tacttctatt tgatcatgac   5100
aaacctgaga gccctgccca gagttcagtg gatcctaatg aactccaaga gtaattcatt   5160
ccctcaccaa ctctaggggc ttggccagtg cagaaaatgt catgggattt taaagttaac   5220
atgagctgct atccaaactt atgtctcttt aagaatggag agacacaggc caggagaggt   5280
aacatatgaa gcctggtatt gggcagtagc ttgatggagt attgaggcta aaagtagact   5340
tcctgcccct gaccatacac aacacccttt cagtttgatc catggtggtc ttattctact   5400
ttattttgag cacctgtcac acctagttac tgtcatgcca agaaggtcca taacaggcaa   5460
atcctactct gctgtgtgca cacaagagga aggaggctca cagtagcaag taaacagata   5520
agcaaacgta cacgattttc gtcttaaagt cattaagaca cacgcgtacc cctcttttgt   5580
ttcagagggt atacaggctg aacagatgtc agtgttcacc tattcttatt gataagcccc   5640
atgtgctttc attggttgaa tgttttatgt taaaacgtca tattgccatc gtaaaatgca   5700
tattgtatgt tgttgggtat ataattaact aatatgcatc gcatgtatga attctaatct   5760
ctgtaaatga aaacttatat atgttaacat atgtaatagt tataatttaa taaactgaca   5820
ctggagac                                                            5828

<210> SEQ ID NO 11
<211> LENGTH: 759
<212> TYPE: DNA
<213> ORGANISM: Rattus norvegicus

<400> SEQUENCE: 11
atggcagagg agctggggct gggctttggg gaagcagtcc cagtggaaat gctgccggaa     60
ggctgccggc acaggcgaga ggccaggacc gggctagcag ccaggagcaa agcctgtttg    120
gctctcacct gctgcctgtt atcatttccc atcctcgcag gacttagcac cctcctgatg    180
actggccagc tccggatccc cggaaaagac tgtatgtttc cgactgtgac agaagagagg    240
tctgcccctt cagcacaacc agtttacaca ccttccagag acaagccaaa agcccacctg    300
acaattatga gacaaactcc tgtaccacat ctgaaaaatg aactggctgc tctacactgg    360
gagaataacc tagggatggc cttcaccaag aaccgaatga actacaccaa caaattcctg    420
gtgatcccag agtcaggaga ctatttcatc tactcccaga tcacattccg aggaaccaca    480
tctgagtgtg gtgacatcag cagggtgaga cggccaaaaa agccagactc catcactgtg    540
gttatcacca aggtagcaga cagctaccct gagcctgccc acctccttac agggaccaag    600
tctgtgtgtg aaataagcag caactggttt cagcccatct accttggggc catgttctcc    660
ttggaagaag gggacaggct gatggtaaat gtcagtgaca tctccttggt ggattacaca    720
aaagaagata aactttctt tggagccttc ttgatatga                            759
```

TL1A MODEL OF INFLAMMATION FIBROSIS AND AUTOIMMUNITY

FIELD OF INVENTION

This invention relates to inflammatory bowel disease, such as Crohn's disease and ulcerative colitis, fibrosis, and related inflammatory diseases and conditions.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Inflammatory bowel disease (IBD) includes several forms of inflammatory diseases and conditions affecting various parts of the gastrointestinal (GI) tract, such as the colon and small intestine. The main forms of IBD include Crohn's disease (CD) and ulcerative colitis (UC), among other forms of colitis. Hallmarks of IBD include inflammation of the digestive tract in compartments of the epithelial mucosa or transmural lesions in the bowel watt. The inflammatory state of the GI tract in CD and others forms of IBD are due in part to an autoimmune response, and a particularly serious complication is fibrosis (also known as fibrostenosis), wherein excessive connective tissue is generated as a result of chronic inflammation of intestinal tissue.

For example, CD is a chronic inflammatory disease that can affect any part of the gastrointestinal tract, The incidence of CD is increasing, with an incidence of between 3.1 and 14.6 cases per 100,000 person-years and an overall prevalence between 26.0 and 198.5 cases per 100,000 person years. The mean age at diagnosis of CD is generally in the third decade of life with similar frequency in men and women. This disease has a chronic intermittent course with only 10% of patients experiencing prolonged remission. Therapy for this disorder has progressed from non-specific agents such as glucocorticoids and 5-aminosalicylate compounds to biologic agents that target specific aspects of the immune response such as inhibitors of TNF-α. An improved understanding of the immune defects in CD will improve the spectrum of available therapy.

As TNF-α is well-known to be a pro-inflammatory cytokine, targeting biological factors related to the TNF-α, signaling pathway may lead to diminution of the causative agents which promote IBD pathogenesis. As a leading example, TL1A (TNFSF15) is a member of the TNF superfamily that binds to death domain receptor 3 (DR3, TNFRSF25) (FIG. 1A). The expression of TL1A is increased in inflamed tissue of colon and small bowel of CD patients, co-localizing to macrophages and T-cells. In particular, lamina propria of the epithelial mucosa and peripheral CD4+CCR9+ T-cells constitutively express membrane TL1A and are especially sensitive to TL1A stimulation. The role of TL1A in the pathology of mucosal inflammation has been recently tested by using neutralizing antibodies to TL1A where inactivating the function of TL1A can attenuate inflammation in various murine colitis models. Together, TL1A/DR3 signaling could have a pleiotropic effect and include amplifying the innate immune response, modulating adaptive immunity by augmenting Th1, Th2, and Th17 effector cell function, and T-cell accumulation and immunopathology of inflamed tissue. Given its immune modulatory effects, blocking TL1A-DR3 signaling is a promising therapeutic strategy in a variety of T-cell-dependent autoimmune diseases including forms of IBD, such as CD and UC, and related fibrotic conditions such as liver periportal fibrosis, bile duct fibrosis, primary biliary cirrhosis, livery periportal inflammation and bile duct inflammation.

BRIEF DESCRIPTION OF FIGURES

Exemplary embodiments are illustrated in referenced figures. It is intended that the embodiments and figures disclosed herein are to be considered illustrative rather than restrictive.

FIG. 10 depicts, in accordance with an embodiment herein, transgenic mice are born less than predicted Mendelian rate.

DESCRIPTION OF THE INVENTION

Figure 1:
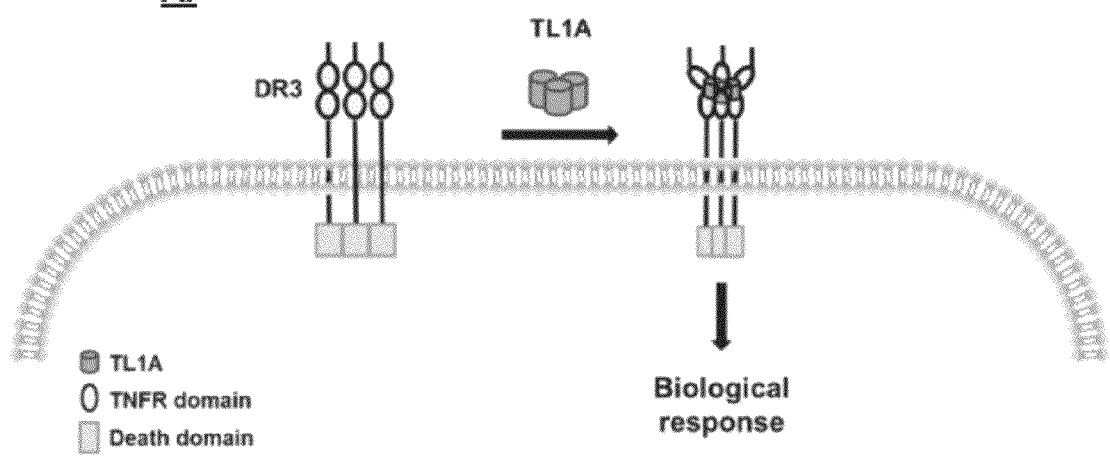
FIG. 1 depicts, in accordance with an embodiment herein, representations depicting the general background of (A) TL1A binding to death domain receptor 3 and (B) potential roles thr TL1A involvement in IBD.

All references cited herein are incorporated by reference in their entirety as though fully set forth. Unless defined otherwise, technical and scientific terms used herein have the same meaning as commonly understood by one of ordinary skill in the art to which this invention belongs. Singleton et at, *Dictionary of Microbiology and Molecular Biology* 3rd ed., J. Wiley & Sons (New York, N.Y. 2001); March, *Advanced Organic Chemistry Reactions, Mechanisms and Structure 5th ed.*, J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below. As used herein, the term "IBD" as used herein is an abbreviation of inflammatory bowel disease. Examples of IBD include several diseases such as Crohn's disease, ulcerative colitis, other forms of colitis such as collagenous colitis, lymphocytic colitis, ischaemic colitis, diversion colitis, Behçet's disease, and indeterminate colitis, among others.

As used herein, the term "CD" is an abbreviation of Crohn's disease.

As used herein, the term "GWAS" is an abbreviation for genome wide association study.

As used herein, the term "PBC" means primary biliary cirrhosis.

As used herein, the term "PSC" means primary sclerosing cholangitis.

As used herein, the term "TL1A" is a TNF-like cytokine factor encoded by the gene TNFSF15. Examples of TL1A include mouse TL1A, such as NCBI reference sequence NM_177371.3, rat TL1A such as NCBI ref. seq. AF520787.1, and human TL1A, such as NCBI ref. seq. NM_005118, NM_001204344.1, among others.

As used herein, the term "UC" means ulcerative colitis.

As used herein, the term "WT" means wild type.

As used herein, the term "biological sample" means any biological material from which nucleic acid molecules can be obtained. As non-limiting examples, the term encompasses whole blood, plasma, saliva, cheek swab, or other bodily fluid or tissue that contains nucleic acid molecules.

As described herein, IBD includes several forms of disease characterized by inflammation of the GI tract. For example, CD is a chronic inflammatory condition with pathological features such as patchy transmural gut inflammation and fibrostenosis with relative sparing of the rectum. [2,53] A serious complication of chronic inflammation is fibrostenosis, which describes severe, often treatment-resistant, disease, that is a source of significant morbidity and in nearly every case requires surgical intervention.

A role for TL1A in gut mucosal inflammation is highlighted by the finding that neutralizing TL1A antibody prevented and treated chronic colitis in mice. However, the contribution of either lymphoid or myeloid derived TL1A to the development of gut inflammation is not fully known. TL1A is the product of the TATESF15 gene that is expressed by both lymphoid and myeloid derived cells. Variants in the TNFSF15 gene have been found to be associated with IBD. The protein product of TNFSF15, TL1A, is elevated in the intestinal mucosa of IBD patients. Certain TATSF15 haplotypes are associated with susceptibility in non-Jewish Caucasian CD and UC. In addition, TNFSF15 haplotype B is not only associated with risk, but also with severity in Jewish CD patients. [23,54] Moreover, monocytes from Jewish patients carrying the risk haplotype B express higher levels of TL1A in response to FcγR stimulation. [24] These results show that CD associated TATSF15 genetic variations contribute to enhanced induction of TL1A, resulting in severe, chronic mucosal inflammation and that modulation of TL1A may be a potential target for therapeutic development.

TL1A signals via death domain receptor 3 (DR3) and several studies implicate the TL1A/DR3 signaling pathway in mucosal inflammation. [55, 56] Neutralizing TL1A-antibody ameliorates inflammation in DSS and Gai2−/− T cell transfer chronic colitis models. [9] Constitutive TL1A expression in mice leads to mild spontaneous ileitis and increased collagen deposition. [16, 117, 57]

TL1A modulates the adaptive immune response in the T-helper (Th)-1 effector arm, as shown by TL1A enhanced interferon (IFN)-γ production from peripheral and mucosal T-cells. [4,5] In addition to mediating the Th1 response, TL1A also plays a role in augmenting Th-2 and -17 effector cell function. [9, 11-13] A differential effect of TL1A on Th-17 cells was recently shown by results demonstrating that TL1A is capable of inhibiting Th-17 development in naïve T-cells, but maintains the effector characteristics of committed Th-17 cells. [58]

As disclosed herein, the inventors investigated the in vivo role of TL1A in myeloid and lymphoid cells by establishing a new set of TL1A transgenic animal models. Transgenic (Tg) mice were established with constitutive TL1A expression in myeloid or lymphoid cells, specifically in T-cells and antigen presenting cells (APCs), using tissue specific promoters. For myeloid cells, FMS promoter was used. For lymphoid cells, LCK promoter with a CD2 enhancer was used. In each case, TL1A expressing cells were marked by GFP using an IRES element in the Tg construct. These two sets of novel TL1A transgenic mice, myeloid ("FM-TL1A-GFP", also described as "M-Tg") mice, and lymphoid ("LCK-CD2-TL1A-GFP Tg", also described as "L-Tg") mice were characterized using cell sorting (FACS), histology, gene expression, surface marker expression, standardized disease assessment, among others, As further disclosed herein, the inventors discovered that mild small bowel inflammation was induced by constitutive TL1A expression in either myeloid or lymphoid cells. More extensive small bowel inflammation observed in L-Tg mice was the result of induction of pro-inflammatory cytokines at an earlier age in these mice. Both myeloid M-Tg mice and lymphoid L-Tg mice also developed extensive biliary fibrosis as well as liver fibrosis, resembling human primary sclerosing cholangitis ("PSC"), as well as primary biliary cirrhosis ("PBC"). Further studies using induction models for colitis, dextrose sodium sulfate induction and adoptive transfer, were applied to evaluate in vivo response of myeloid M-Tg mice and lymphoid L-Tg mice to induced colitogenic conditions.

As described herein, the present invention provides an animal model for a disease and/or condition, including a transgenic animal that overexpresses TL1A. In some embodiments, the animal is a rodent. In some embodiments, the animal is a mouse or a rat. In some embodiments, the disease and/or condition is inflammatory bowel disease (IBD). In other embodiments, the disease and/or condition is Crohn's disease, ulcerative colitis, other forms of colitis such as collagenous colitis, lymphocytic colitis, ischaemic colitis, diversion colitis, Behçet's disease, or indeterminate colitis. In some embodiments, the disease and/or condition is fibrosis and/or inflammatory condition is indicative of biliary fibrosis, liver fibrosis, liver periportal fibrosis, bile duct fibrosis, primary biliary cirrhosis (PBC), human primary sclerosing cholangitis (PSC), liver periportal inflammation, and/or bile duct inflammation.

In other embodiments, the TL1A overexpression is specific to a cell type. In some embodiments, the cell type is a myeloid cell. in sonic embodiments, the myeloid cell is an antigen presenting cell (APC) or dendritic cell (DC). In other embodiments, the myeloid cell is a neutrophil, eosinophil, basophil, monocyte, and/or macrophage. In other embodiments, the cell type is a cell found in the bone marrow or spinal cord. in other embodiments, the cell type is a lymphoid cell. In some embodiments, the lymphoid cell is a T-cell. In other embodiments, the lymphoid cell is natural killer (NK) or B-cell. in other embodiments, the lymphoid cell is a cell found in the lymphatic systems, such as lymph nodes, or in peripheral blood. In other embodiments, the cell type also expresses a fluorescent marker. In other embodiments, the marker is green fluorescent protein (GFP), enhanced green fluorescent protein (EGFP), red fluorescent protein (RFP), blue fluorescent protein (BFP) or yellow fluorescent protein (YFP).

In other embodiments, the transgenic rodent has increased T-cell expression of one or more of the markers selected from the group consisting of: CD4, CD8, CD86, CCR9, CCR10, FoxP3, TNF-γ, IFN-γ, IL-10, and/or IL-17. In other embodiments, transgenic rodent has increased expression of IGF-1 or TGF-β. In other embodiments, the transgenic rodent expresses increased levels of pro-inflammatory, gut homing/migration and/or $T_{reg}$ markers in lamina propria mononuclear cells (LPMC), mesenteric lymph node (MLN), and/or splenic In other embodiments, the animal model is a transgenic rodent that expresses TL1A in about 35, 40, 45, 50, or 55% of all myeloid cells in a sample of myeloid cells isolated from the transgenic rodent. in other embodiments, the transgenic rodent expresses TL1A in about 80, 85, 90, 95, or 99% of all T-cells in a sample of T-cells isolated from the transgenic rodent.

In other embodiments, the transgenic rodent exhibits fibrostenosis, inflammation in the gastrointestinal (GI) tract, weight loss, and/or an increase in disease-activity index (DAI). In some embodiments, fibrostenosis may be induced using dextrose sodium sulfate (DSS). In some embodiments, the dextrose sodium is less than 2.5% of the administered solution. In other embodiments, the transgenic rodent displays myeloperoxidase (MPO) or hematoxylin and eosin (H&E) staining characteristic of IBD. In other embodiments, the transgenic rodent displays increased numbers of goblet T-cells, Paneth cells, or LPMC inflammatory infiltrate, myeloperoxidase (MPO) or hematoxylin and eosin (H&E) staining characteristic of IBD. in some embodiments, fibrostenosis may be shown by increased vimention or collagen expression in the GI tract. In other embodiments, the transgenic rodent has an increased histology score in the rectum, cecum, colon, duodenum, jejunum and/or ileum. In other embodiments, the transgenic rodent displays increased colon hyperemia, increased colon thickness, increased colon stiffness, and/or stricture with proximal dilation. In other embodiments, the transgenic rodent displays extra intestional pathology, such as ulcerated skin lesion or arthropathy. In other embodiments, the transgenic rodent exhibits less than expected Mendelian frequency when crossed with wild-type mice. In some embodiments, the expected Mendelian frequency is about 50%.

As further described herein, the present invention provides a method of preparing a transgenic animal with tissue specific constitutive expression of TL1A including providing a transgenic construct containing a tissue specific promoter operatively linked to a TL1A genetic locus, and generating a transgenic animal with tissue specific constitutive expression of TL1A by injecting the transgenic construct into a pronucleus.

In some embodiments, the transgenic construct contains a myeloid specific promoter. In other embodiments, the myeloid specific promoter is FMS. In some embodiments, the transgenic construct contains a lymphoid specific promoter and/or enhancer. In other embodiments, the lymphoid specific promoter is LCK. In other embodiments, the lymphoid specific enhancer is CD2. In other embodiments, the transgenic construct contains a fluorescent marker. In other embodiments, the fluorescent marker is green fluorescent protein (GFP), enhanced green fluorescent protein (EGFP), red fluorescent protein (RFP), blue fluorescent protein (BFP) or yellow fluorescent protein (YFP). In certain embodiments, the transgenic construct is FMS-TL1A-GFP or LCK-CD-TL1A-GFP. In other embodiments, the transgenic construct contains an IRES element. In other embodiments, transgenic construct allows for bi-cistronic expression.

In other embodiments, the transgenic animal may be identified as containing a transgenic construct including a tissue specific promoter operatively linked to a TL1A genetic locus by using one the primers described in SEQ ID NO. 2, SEQ ID NO: 3, SEQ ID NO: 4, SEQ ID NO: 5, SEQ ID NO: 6 or SEQ ID NO: 7.

In other embodiments, the transgenic construct contains a sequence containing about 70%, 75%, 80%, 85%, 90%, 95%, or 99% or more sequence similarity to SEQ ID NO: 1, SEQ ID NO: 8, SEQ ID NO: 9, SEQ ID NO: 10, or SEQ ID NO: 11. In other embodiments, the transgenic construct contains a sequence containing about 70%, 75%, 80%, 85%, 90%, 95%, or 99% or more sequence similarity to a nucleotide sequence encoded by TNFSF15. In other embodiments, TNFSF15 is mouse, rat, or human TNFSF15.

The present invention also provides a cell culture including an isolated population of cells constitutively expressing TL1A. In some embodiments, the cell culture includes cells that are T-cells, antigen presenting cells (APC), and/or dendritic cells (DC). In some embodiments, the cells also express a fluorescent marker. In other embodiments. the fluorescent marker is green fluorescent protein (GFP), enhanced green fluorescent protein (EGFP), red fluorescent protein (RFP), blue fluorescent protein (BFP) or yellow fluorescent protein (YFP). In some embodiments, the cells contain a FMS-TL1A-GFP or LCK-CD2-TL1A-GFP transgenic construct.

The present invention also provides a method of preparing a rodent model, including providing a quantity of cells constitutively expressing TL1A, and injecting the quantity of cells into a rodent to generate the rodent model. In some embodiments, the mouse is an immunodeficient mouse, In some embodiments, the immunodeficient mouse is a Rag1–/– mouse. in other embodiment, the cells expressing TL1A also express a fluorescent marker. In other embodiments, the fluorescent marker is green fluorescent protein (GFP).

In some embodiments, the quantity of cells is obtained from a transgenic rodent overexpressing TL1A by a process, including, drawing a sample comprising a population of cells from the transgenic rodent; sorting the sample into a first sub-population of cells that constitutively express TL1A and a second sub-population of cells that do not constitutively express TL1A; and separating the first sub-population from the second sub-population, thereby isolating the sub-population of cells that constitutively express TL1A. In some embodiments, the cells expressing TL1A also express a fluorescent marker. In some embodiments, the fluorescent marker is green fluorescent protein (GFP). In some embodiments, the first sub-population of cells that constitutively express TL1A are fluorescent cells and the second sub-population of cells that do not constitutively express TL1A are non-fluorescent cells, and separating the first sub-population of fluorescent cells from the second sub-population of non-fluorescent cells isolates the sub-population of cells that constitutively express TL1A. In some embodiments, the mouse is an immunodeficient mouse. In some embodiments, the immunodeficient mouse is a Rag1–/– mouse.

Also described herein is a method of propagating a cell culture including obtaining a quantity of cells constitutively expressing TL1A and a fluorescent marker, expanding the quantity of cells, and establishing a sub-culture of the expanded quantity of cells, wherein the sub-culturing propagates the cell culture. In other embodiments, the method further includes injection of the sub-culture into a mouse. In some embodiments, the mouse is an immunodeficient mouse, In some embodiments, the immunodeficient mouse is a Rag1–/– mouse.

In some embodiments, the quantity of cells is obtained after isolation from a transgenic rodent that expresses a fluorescent marker and overexpresses TL1A, wherein isolation from the transgenic rodent includes drawing a sample comprising a population of individual cells from the transgenic rodent; sorting the sample comprising a population of individual cells into a first sub-population of individual fluorescent cells and a second sub-population of individual non-fluorescent cells, wherein a fluorescent cell constitutively expresses TL1A and an non-fluorescent cell does not constitutively express TL1A; and separating the first sub-population of individual fluorescent cells from the second sub-population of individual non-fluorescent wherein separating the sub-population of individual fluorescent cells isolates the population of cells that constitutively express TL1A. In some embodiments, the first sub-population of individual fluorescent cells is injected into a mouse. in other embodiments, the mouse is an immunodeficient mouse. In some embodiments, the immunodeficient mouse is a Rag1–/– mouse.

In other embodiments, a transgenic rodent or a culture of cells constitutively expressing TL1A and a fluorescent marker serves as a resource for obtaining T-cells that constitutively express TL1 A. In some embodiments, these T-cells may be obtained or isolated and injected into an immunodeficient mouse, as exemplified using the adoptive-transfer model. In some embodiments, the immunodeficient mouse is a Rag1–/– mouse. In some embodiments, the immunodeficient mouse recipient will exhibit inflammation in the gastroinestional (GI) tract, gross fibrosis or increased inflammatory infiltrate.

The present invention also provides a method of drug screening including providing a model comprising a quantity of cells constitutively expressing TL1A, a transgenic animal that overexpresses TL1A or an immunodeficient mouse that has been injected with an amount of cells that constitutively express TL1A, administering one or more drugs to the model, and detecting a change in the model to determine if the one or more drugs has an effect of interest on the model. In some embodiments, the cells expressing TL1A also express a fluorescent marker. In some embodiments, the fluorescent marker is green fluorescent protein (GFP). The present invention also provides a method of drug screening including providing an animal model as described herein, administering one or more drugs to the animal, and detecting a change in or reaction by the animal to determine if the drug has an effect of interest.

In one embodiment, the present invention provides an animal model for inflammation where TL1A is constitutively expressed. In another embodiment, the TL1A is constitutively expressed in one or more cell types of interest. in another embodiment, the TL1A gene is under the control of a tissue specific promoter. In another embodiment, the cell type of interest comprises T-cells and/or myeloid cells, In another embodiment, the animal is a mouse. In another embodiment, the inflammation is indicative of inflammatory bowel disease. In another embodiment, the inflammation is indicative of Crohn's disease, ulcerative colitis, other forms of colitis such as collagenous colitis, lymphocytic colitis, ischaemic colitis, diversion colitis, Behçet's disease, or indeterminate colitis. in another embodiment, the fibrosis and/or inflammatory condition is indicative of biliary fibrosis, liver fibrosis, liver periportal fibrosis, bile duct fibrosis, primary biliary cirrhosis (PBC), human primary sclerosing cholangitis (PSC), liver periportal inflammation, and/or bile duct inflammation.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

TL1A Generally and Design Study

Emerging evidence reveals that TL1A is an important modulator of the Th1, Th2, and Th17 pathways. In addition, TL1A is also important in innate immune response. To better understand the biology of TL1A, and a role in the adaptive immunity Th1 response, it would be advantageous to study TL1A in a physiological context. Therefore, generation of TL1A transgenic mice over-expressing TL1A (gain-of-function) is important to understand the pathophysiology of IBD and to generate an animal model recapitulating IBD as an in viva model system to study IBD drug targets, generate IBD drugs, and to test current the efficacy of potential IBD therapies.

Transgenic (Tg) mice with constitutive TL1A expression in myeloid or lymphoid cells, such as T-cells and antigen presenting cells (APCs), were generated using tissue specific promoters. For myeloid cells, EMS (also known as "c-fms") promoter was used. For lymphoid cells, LCK promoter was used with a CD2 enhancer. In each case, TL1A expressing cells were marked by GFP using an IRES element in the Tg construct. The resulting TL1A transgenic mouse lines constitutively express TL1A and are tagged with GFP in the cell type of interest. Successful generation of the lymphoid TL1A transgenic mice ("LCK-CD2-TL1A-GFP", also described as "L-Tg") and myeloid TL1A transgenic mice ("FMS-TL1A-GFP", also described as "M-Tg") was followed by characterization using cell sorting (FACS), histology, gene expression, surface marker expression, and standardized disease assessment, among others. Generally, L-Tg mice were found to express TL1A and GFP in 95% of all T-cells, while M-Tg mice express TL1A and GFP in 50% of all myeloid cells.

Example 2

Tissue Specific Expression in Lymphoid L-Tg Mice and Myeloid M-Tg Transgenic Mice Lymphoid L-Tg transgenic mice and myeloid M-Tg transgenic mice specifically overexpress TL1A in specific tissues and cells, such as T-cells and APCs. This was done by cloning the TL1A gene under the control of tissue specific promoters. The promoters used included the lymphoid LCK promoter and CD2 enhancer as related to T-cells, and the myeloid FSM promoter as related to APCs.

Figure 2:
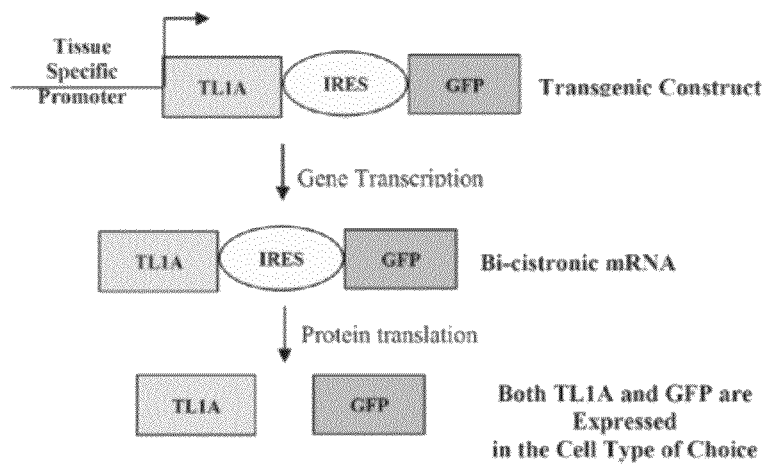
FIG. 2 depicts, in accordance with an embodiment herein (A) a schematic drawing of a transgenic construct used in generation of cell type specific TL1A over-expressing transgenic mice, and (B) a general strategy to generate tissue specific TL1A expression.
Figure 2:
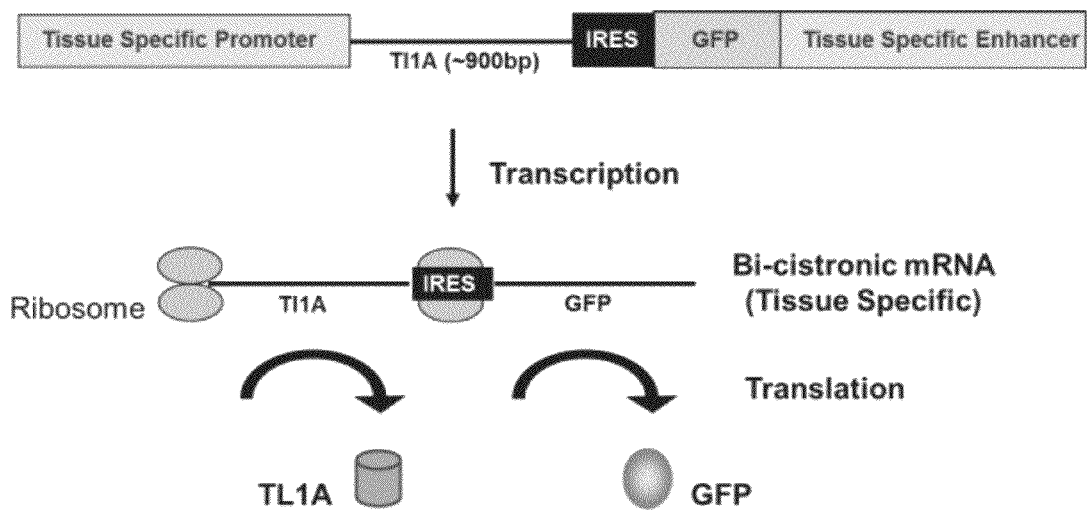

Proximal LCK promoter and CD2 enhancer are known to drive T cell lineage-specific expression, such as CD4-CD8-double negative thymocyte stage T-cell progenitors, and the FMS promoter is known to mediate myeloid specific expression in APC such as macrophages and DC [18,19]. In both cases, the inventors also cloned an IRES-GFP element downstream of the cloned murine TL1A, wherein green fluorescent protein (GFP) is cloned downstream of internal ribosomal entry site (IRES) in the transgenic construct (FIG. 2A). IRES will mediate protein translation from the bi-cistronic mRNA so that cells overexpressing TL1A will also be marked by green fluorescence, thereby allowing convenient identification, isolation and purification of Tg TL1A expressing cells via GFP fluorescence (FIG. 2B).

The cloning strategies and schematic of the Tg construct are further described herein. The Tg constructs were injected into C57BL/6 pronuclei to ensure genetic homogeneity.

Example 3

Generation of TL1A Over-expressing Transgenic Mice

Murine TL1A cDNA (open Biosystems, Clone ID 30740802, SEQ ID NO. 1) was digested by EcoRI/SmaI and inserted into the EcoRI/SmaI site of pIRES2-EGFP (Clontech). To generate lymphoid specific TL1A transgenic mice, DNA fragment containing murine TL1A-IRES2-EGFP was amplified by PCR using:

(SEQ ID NO. 2)
5'-AATGGGGGCGCGCCGGGCTCTCTGGTCAGAAGGGATCAG-3'

(SEQ ID NO. 3)
5'-TTTACGGGCGCGCCCCTTAAGATACATTGATGAGTTTGG-3'

Figure 3:
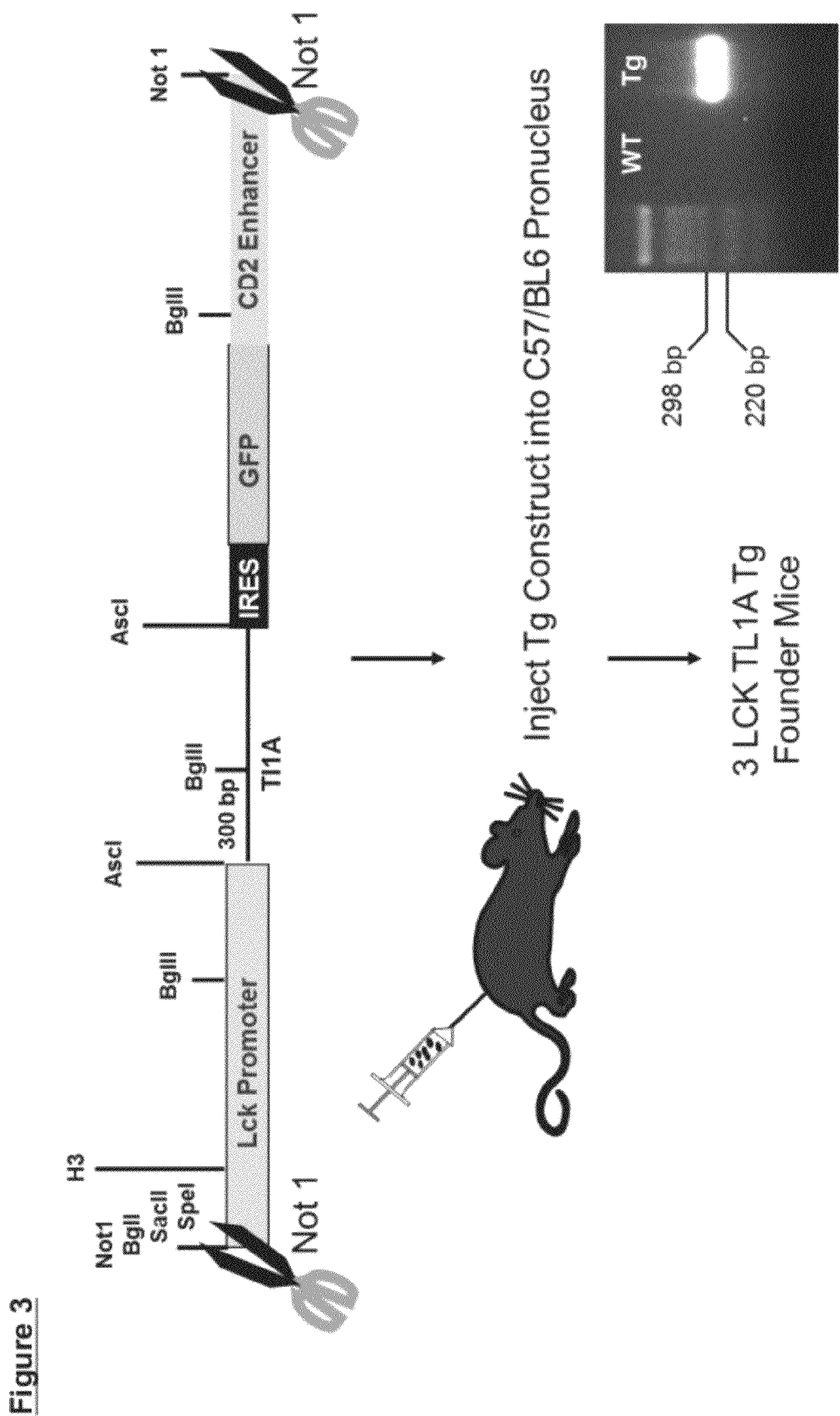
FIG. 3 depicts, in accordance with an embodiment herein, generation of lymphoid specific TL1A transgenic mice ("LCK-CD2-TL1A-GFP Tg", also decribed as "L-Tg" mice).

To generate L-Tg mice, the amplified fragment digested with AscI, and cloned into AscI site of plck.E2 (generous gift from T. Hettmann, The University of Chicago), which contains the proximal lck promoter, human growth hormone gene (polyadenylation site), and locus control region elements from the human CD2 gene to generate plasmid pLCK-TL1A-IRES2-EGFP (FIG. 3). The plck.E2 has been used to mediate T-cell lineage specific expression [19]. The TL1A-IRES2-EGFP fragment was sequenced to confirm that no mutations were generated during the cloning process. A 10-kb fragment was excised by NotI digest and used for microinjection into C57BL/6 pronuclei performed by Caliper Life Sciences. [9] Independent murine lines containing genomic integration of the TL1A transgene were identified by PCR using the following primers:

5'-GACTAACAAAGATGCCTGCCTGTGG-3'  (SEQ ID NO. 4)

5'-GCCATCCTTCTGCTGTCTTGGAGA-3'  (SEQ ID NO. 5)

Only 2 of the 8 lines showed T-cell lineage specific expression of TL1A (95% of T-cells and 34% of T-cells). The inventors used the founder transgenic (Tg) mouse line with TL1A transgene expression in 95% of T-cells and called it LCK-CD2-TL1A-GFP Tg mouse.

Figure 4:
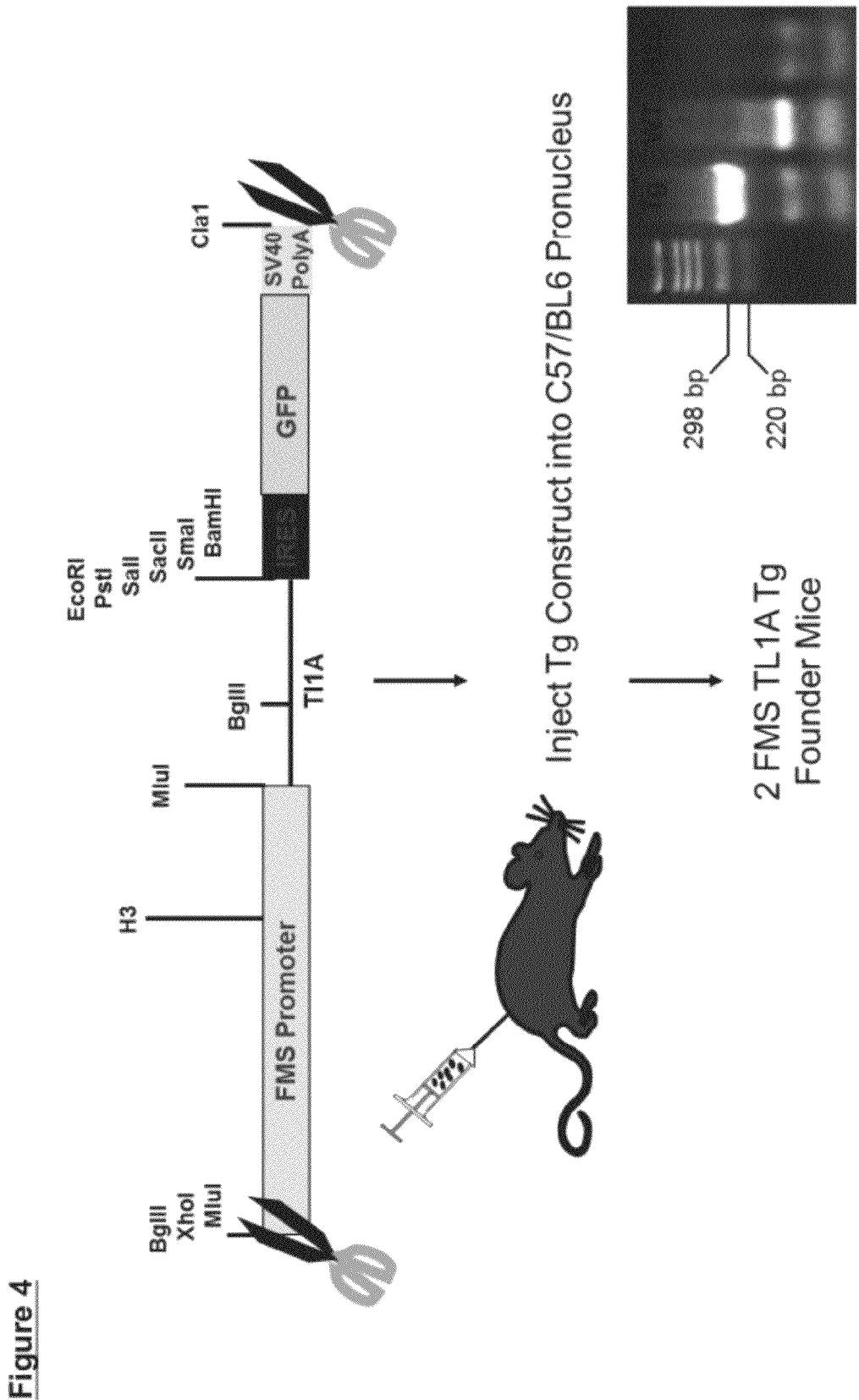
FIG. 4 depicts, in accordance with an embodiment herein, generation of myeloid specific TL1A transgenic mice ("FM-TL1A-GFP Tg", also described as "M-Tg" mice).

To generate myeloid specific M-Tg mice, a XhoI/EcoRI fragment was blunt ended by klenow (NEB) and cloned to blunt ended MluI site of EMS promoter vector (generous gift from D. Underhill, Cedars-Sinai Medical Center) (FIG. 4), TL1A-IRES2-EGFP fragment was sequenced to confirm that no mutations were generated during the cloning process. The FMS promoter vector has been used previously to drive expression in cells of the mononuclear phagocyte lineage including macrophages and dendritic cells. [18] A 10-kb fragment was excised by XhoI/ClaI digest and used for microinjection into C57BL/6 pronuclei performed by Caliper Lite Sciences. 6 independent murine lines containing genomic integration of the TL1A transgene were identified by PCR using the following primers:

5'-TTGGAAGCTGATTGAAGGGTCCA-3'  (SEQ ID NO. 6)

5'-AGCTCCTCTGCCATCCTTCTGCT-3'  (SEQ ID NO. 7)

Two of the six lines showed myeloid specific expression of the transgene in approximately 70% of macrophages and dendritic cells, but one has higher GFP level than the other founder line. The inventors used the founder Tg line with the higher GIP expression, which was named FMS-TL1A-GFP (also described as "M-Tg").

Figure 5:
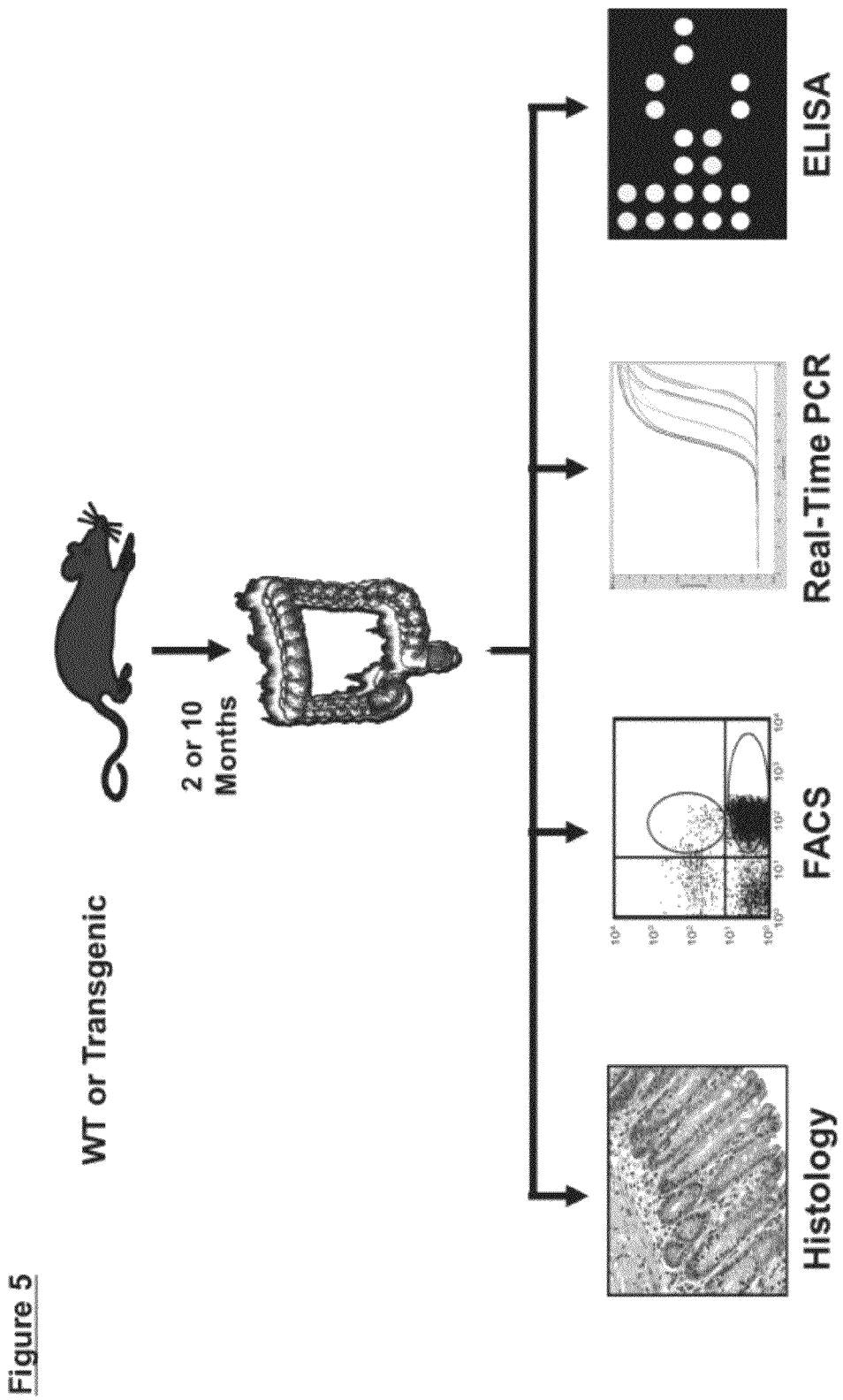
FIG. 5 depicts, in accordance with an embodiment herein, various methods of characterizing transgenic mice, including histology, flow cytometry (FACS), quantitative real-time PCR (qRT-PCR), and immunological ELISA assay.
Figure 6:
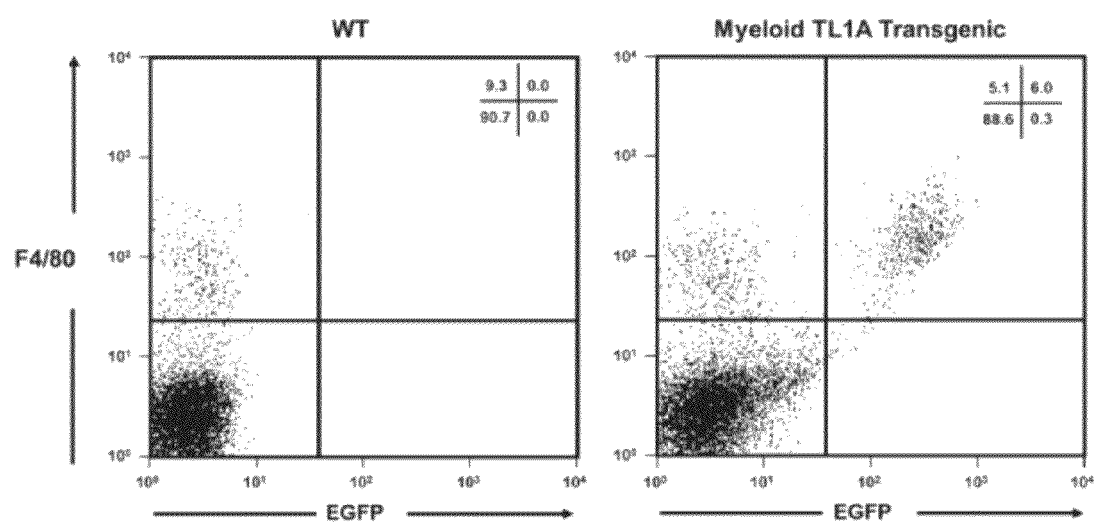
FIG. 6 depicts, in accordance with an embodiment herein, (A) co-localization of GFP with myeloid marker F4/80, and (B) flow cytometric analysis of the transgene marker GFP on either CD11c or F4/80 gated splenocytes from WT (black filled), LCK-CD2-TL1A-GFP Tg mice (L-Tg, dotted line) or FM-TL1A-GFP mice (M-Tg, solid grey line). Representative histograms are shown.
Figure 6:
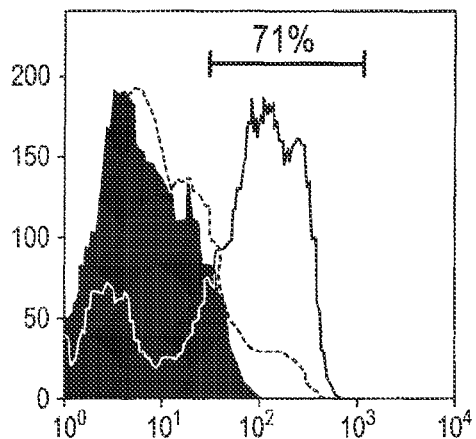
Figure 6:
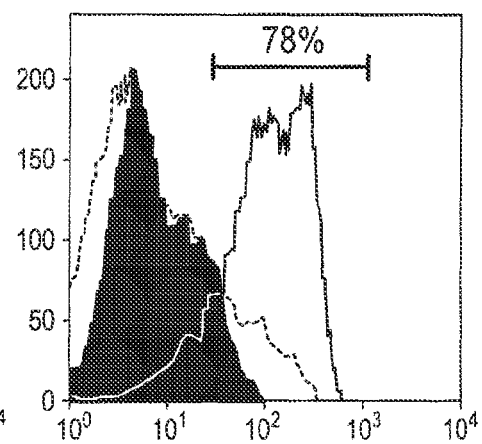
Figure 6:
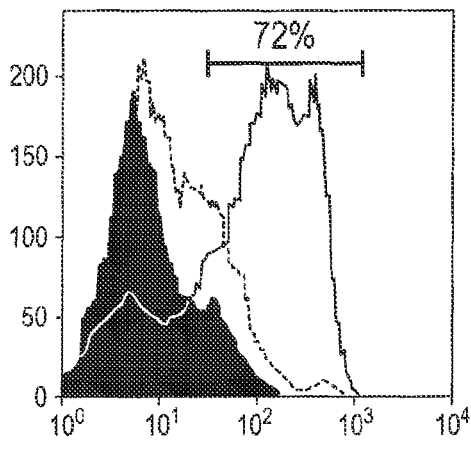
Figure 6:
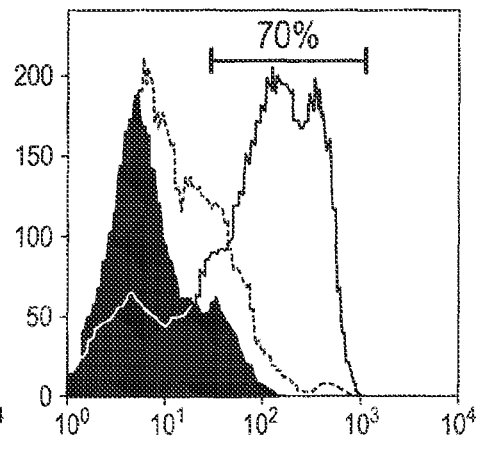
Figure 7:
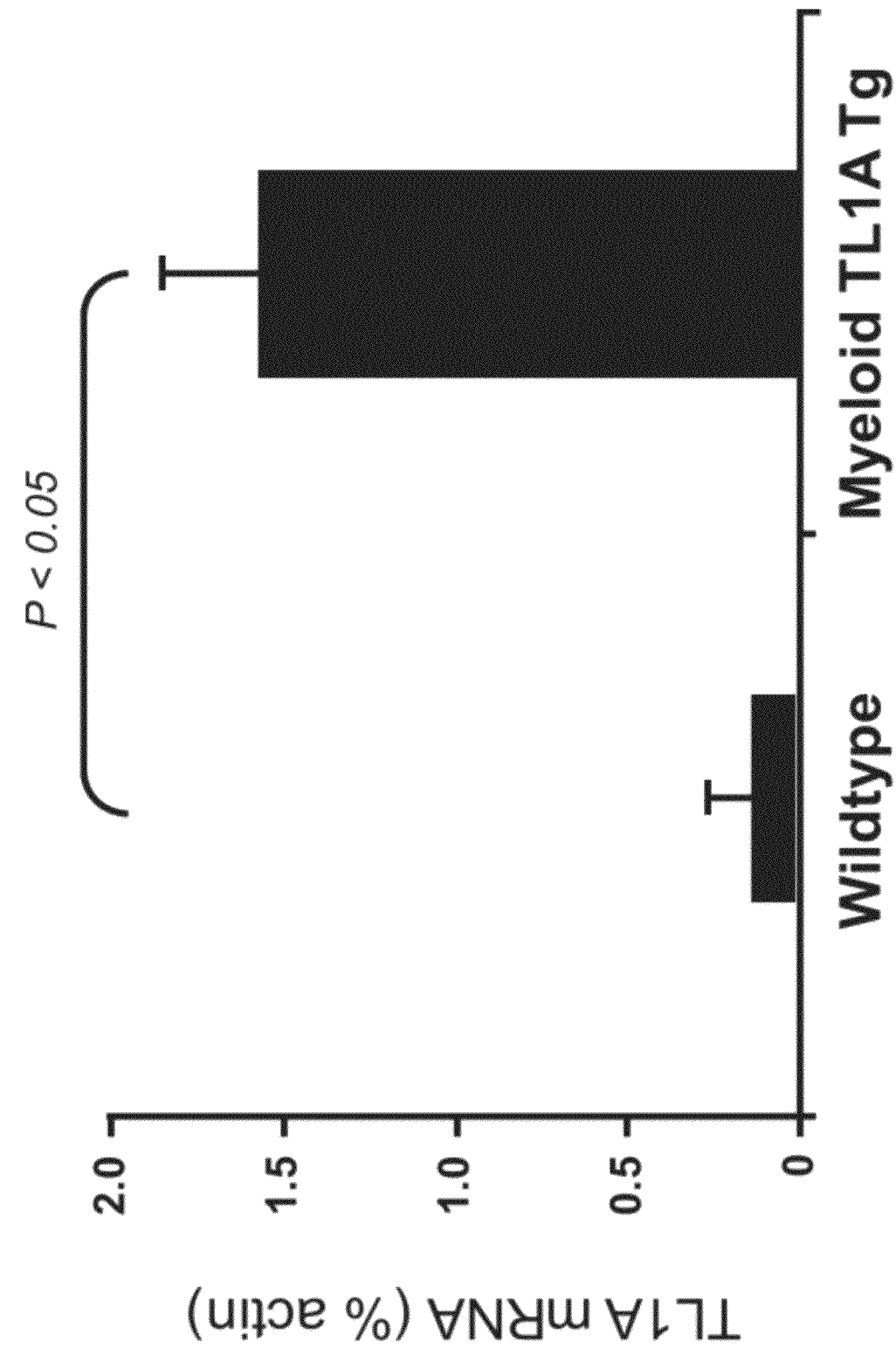
FIG. 7 depicts, in accordance with an embodiment herein, elevated TL1A mRNA in macrophage of myeloid M-Tg mice.

Generally, the resulting transgenic mice which constitutively express TL1A and tagged with GFP in cell type of interest included (a) LCK TL1A GFP Tg Mice (express TL1A and GFP in 95% of all T-cells) (FIG. 8B), and (b) FMS TL1A GFP Tg Mice (express TL1A and GFP in 50% of all myeloid cells) (FIG. 6B). Cell lines were then characterized according to the following described methods (FIG. 5).

Example 4

Expression Analysis

Total RNA was isolated and quantitative reverse-transcription polymerase chain reaction (qRT-PCR) was performed as described. [61] β-actin, Igf-1 and TGF-β mRNA were amplified as described. [9, 60] The amount of transcript was analyzed and expressed as percentage of β-actin. Cytokine concentration was assayed by enzyme-linked immunosorbent assay (ELISA) using kits for IFN-γ, IL-17, IL13, IL-6, and TNF-α (eBioscience, San Diego, Calif.) per manufacturer's protocol.

Example 5

Cell Isolation, Culture, Intracellular Cytokine Expression, and Flow Cytometry

Isolation and culture of lamina propria mononuclear cells (LPMC), mesenteric lymph node (MLN), and splenic cells and their subsequent stimulation by anti-GD28 and anti-CD3 were carried out as reported. [9] The inventors used whole colon samples and the distal 10 cm of the ilea for LPMC isolation. Intracellular staining and antibodies used were described previously. [57] Cells were acquired on a Cyan flow-cytometer (Dako-Cytomation, Carpinteria, Calif.) and analyzed using FlowJo analysis software (Tree Star, Inc, Ashland, Oreg.).

Example 6

Disease Activity Index (DAI), Myeloperoxidase, Macroscopic and Histopathological Analysis Mice were inspected for diarrhea and rectal bleeding once a week for the first 2 months, then once a month thereafter. The disease-activity index (DAI) (combined score of the inventorsight loss, presence of blood in stool, and stool consistency) was determined according to a standard scoring system previously described [20, 75]. Colon and small intestine were scored for macroscopic evidence of inflammation using the established classification [21]. Tissue was fixed in 10% neutral buffered formalin (Sigma). Samples were embedded, sectioned, and stained with hematoxylin and eosin (H&E) by the Histology Core at Cedars-Sinai Medical Center (CSMC). Masson Trichrome staining was performed as described previously [29]. Histopathological scores of colons and small intestine were assigned in a blinded manner by at least 2 trained pathologists (DQS and HWK) using previously established methods [21]. The histologic score is calculated from observation of at least 36 different fields of stained sections at 200× from 6 mice in each group. The numbers of goblet-cells and Paneth cells were determined by examining at least 80 individual villi and crypts from each group.

For inductive colitogenic studies, DAI was determined every other day for the DSS model and twice a week for the adoptive-transfer model according to a standard scoring system. [62] Myeloperoxidase was assessed using the EnzChek Myeloperoxidase Activity Assay Kit according to the manufacturer's protocol (invitrogen, Carlsbad, Calif.). Macroscopic evidence of inflammation was scored using the established classification. [9, 59] Samples were processed and stained with hematoxylin and eosin (H&E) by the CSMC Histology-Core. Masson-Trichrome and vimentin staining were performed as described. [63] Histopathological scores of colons and intestine were assigned in a blinded manner by two trained animal pathologists (DQS and HWK) using established methods. [9, 59] The histologic score, vimentin-positive cells, and collagen thickness were calculated from observation of ≥10 different fields per gut region at 200× magnification from ≥10 mice in each group.

Example 7

Characterization of in vivo Constitutive TL1A Expression in the Myeloid APC and Lymphoid T Cell Lineages Expression of the transgene was determined in myeloid APC M-Tg mice and lymphoid T-cell L-Tg mice by the expression of GET using FACS sorting.

In the M-Tg mice, GFP was present in over 70% of CD11c and F4/80 positive cells (FIGS. 6A, 6B), and the expression of the TL1A transgene mRNA persisted as the mice aged. (FIG.

7). The specificity of the c-fms promoter was illustrated by the fact that the inventors did not detect GFP expression in CD3, CD4 or CD8 positive T-cells.

Figure 8:
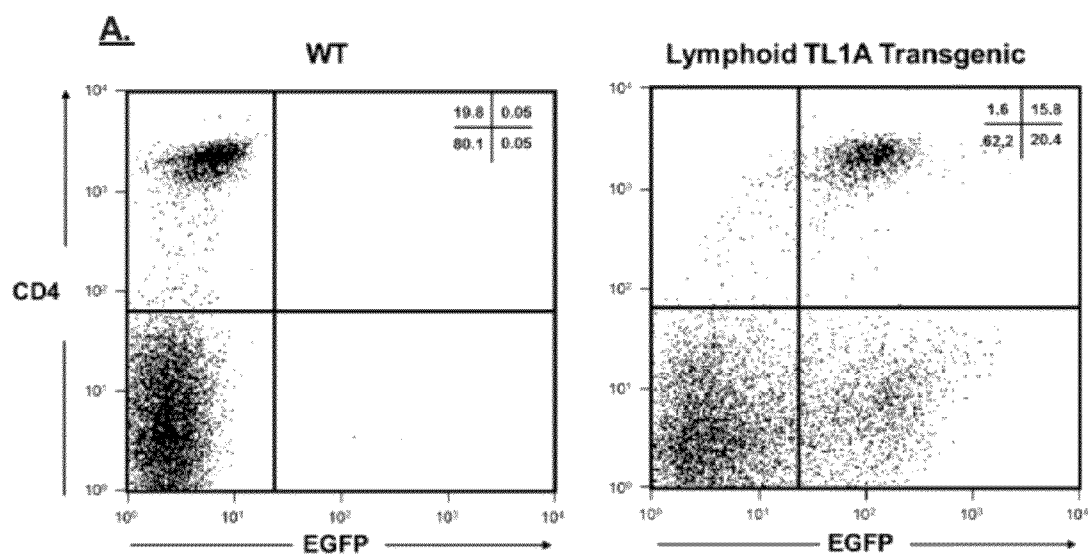
FIG. 8 depicts, in accordance with an embodiment herein, (A) co-localization of GFP with CD4 in peripheral blood, and (B) representative analysis of the transgene marker GFP on either CD3, CD4 or CD8 gated splenocytes from WT (black filled), LCK-CD2-TL1A-GFP Tg mice (L-Tg, dotted line) or FM-TL1A-GFP mice (M-Tg, solid grey line).
Figure 8:
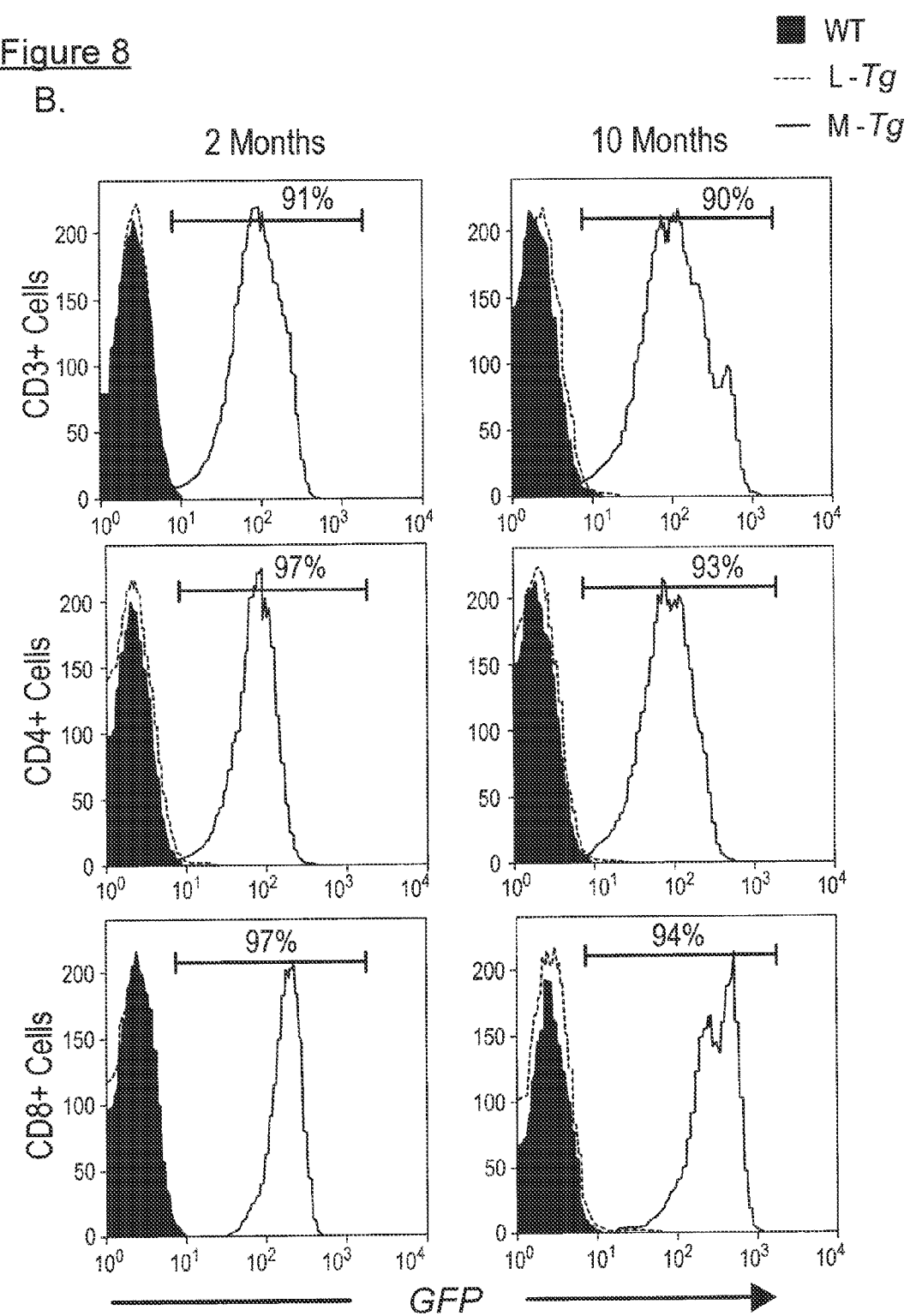
Figure 9:
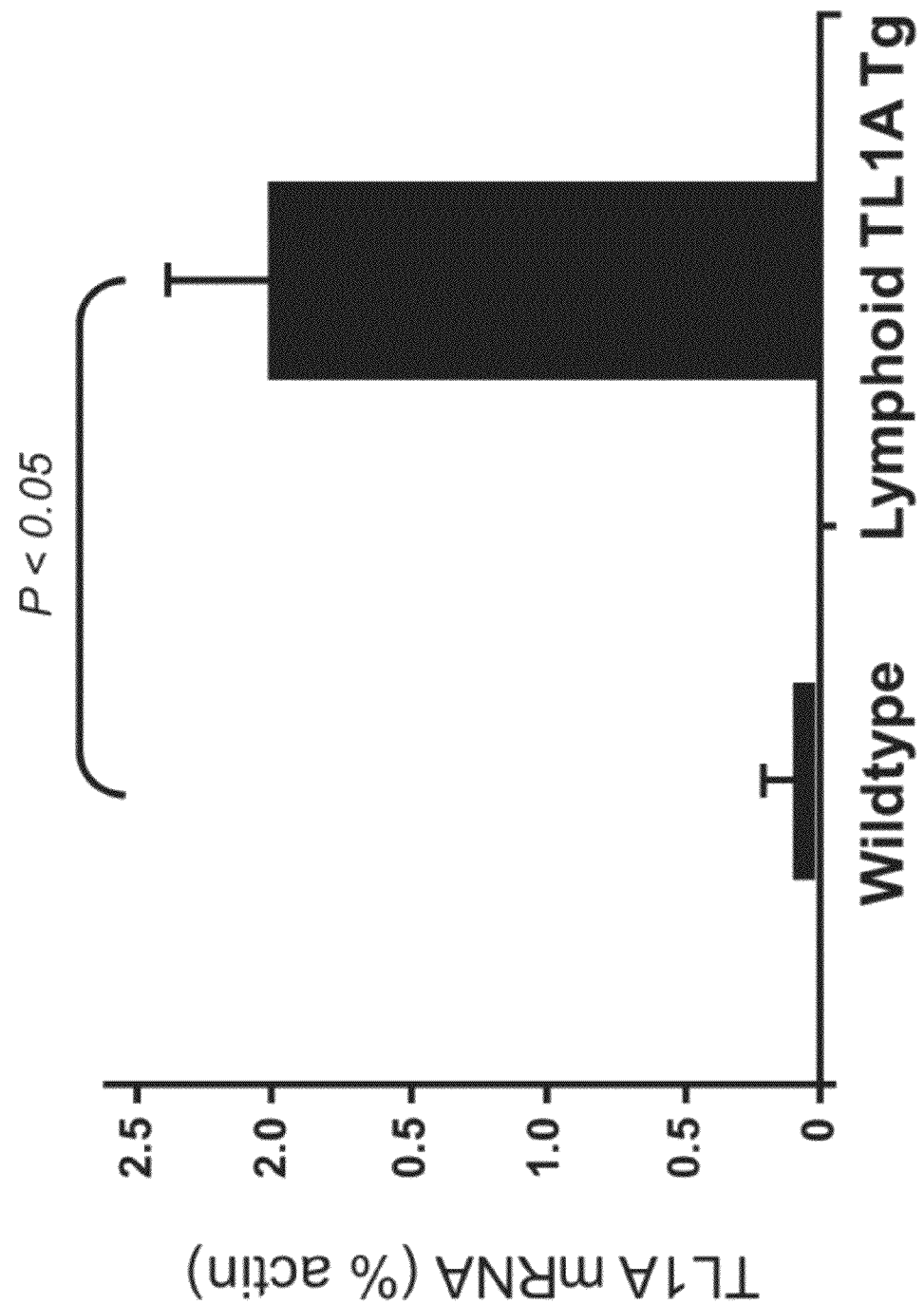
FIG. 9 depicts, in accordance with an embodiment herein, elevated TL1A mRNA in spleen of lymphoid L-Tg mice.

In the L-Tg mice, GFP was present in over 90% of CD3, CD4 and CD8 positive cells (FIGS. 8A, 8B). Similar to the M-Tg mice, the expression of the transgene in the lymphoid. TL1A Tg mice also persisted as the mice got older (FIG. 9), Less than 10% GFP expression was detected in F4/80 or CD11c positive cells (FIG. 6B), indicating that the Lck promoter and Cd2 enhancer element drives T cell lineage-specific expression.

Figure 13:
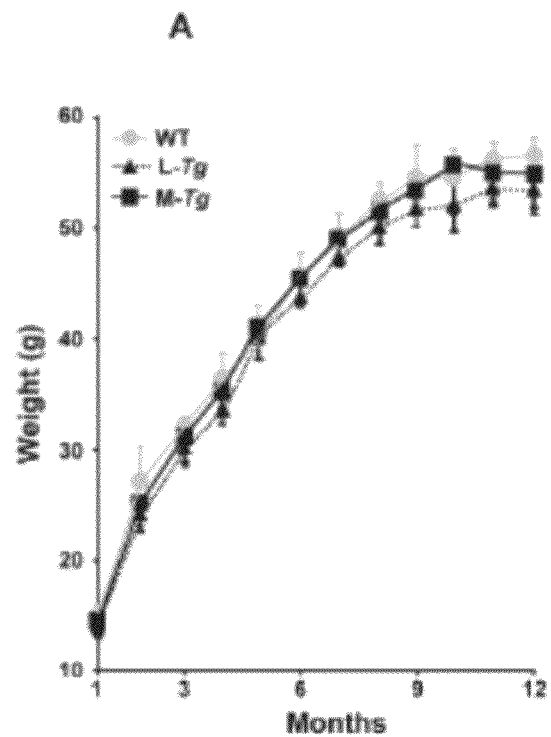
FIG. 13 depicts, in accordance with an embodiment herein, phenotypic characterization of TL1A Tg mice, (A) WT (grey circle), LCK-CD2-TL1A-GFP Tg mice ("L-Tg", black filled triangle) or FM-TL1A-GFP mice ("M-Tg", black filled square) are shown n=2.0 per group. Data are expressed as mean in grams (g) 6 SD, (B) TL1A mRNA expression was determined in the spleen, MLN, ileum or colon by real-time polymerase chain reaction. Data are expressed as mean percent of b-actin 6 standard deviation (SD). *p<0.05, **p<0.01. n=6 independent littermate mice per group were used.
Figure 13:
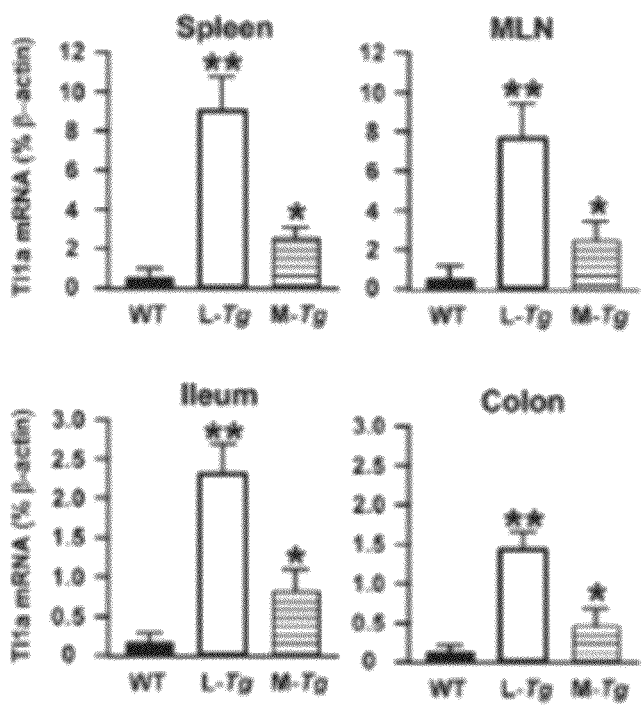

For both Tg cells, the inventors directly showed that TL1A mRNA is higher in the spleen, mesenteric lymph nodes (MLN), colon and ileum of both Tg mice compared to WT mice (FIG. 13B). Together, these data demonstrate that the inventors generated tissue specific constitutive in vivo expression of TL1A in APC and T-cells.

As described, he resulting transgenic mice which constitutively express TL1A and tagged with GFP in cell type of interest included (a) LCK-C2-TL1A-GFP Tg Mice (express TL1A and GFP in 95% of all T-cells), and (b) FMS-TL1A-GFP Tg Mice (express TL1A and GFP in 50% of all myeloid cells). This further enables purification of TL1A constitutively expressing cells to over 99% purity using Tg mice. This has several uses including studying the biology of various immune cell type, mixing cell types in a defined amount and number. All of this can be done using pure cell populations because the Tg cells are tagged with GFP.

Example 8

Mice with Constitutive TL1A Expression

Both M-Tg and L-Tg mice are fertile, but are born at less than Mendelian frequency when Tg were crossed to WT mice (FIG. 10). Mendelian expectation is expected to be 50% transmission of the transgene. When Tg hemizygous mice are mated to WT mice, the frequency of FMSTL1A-GFP Tg mice born is 42% (58/138) and in LCK-CD2-TL1ATg mice, the frequency is 40% (51/126). The M-Tg and IL-Tg mice appeared healthy and gained at similar rates.

Figure 11:
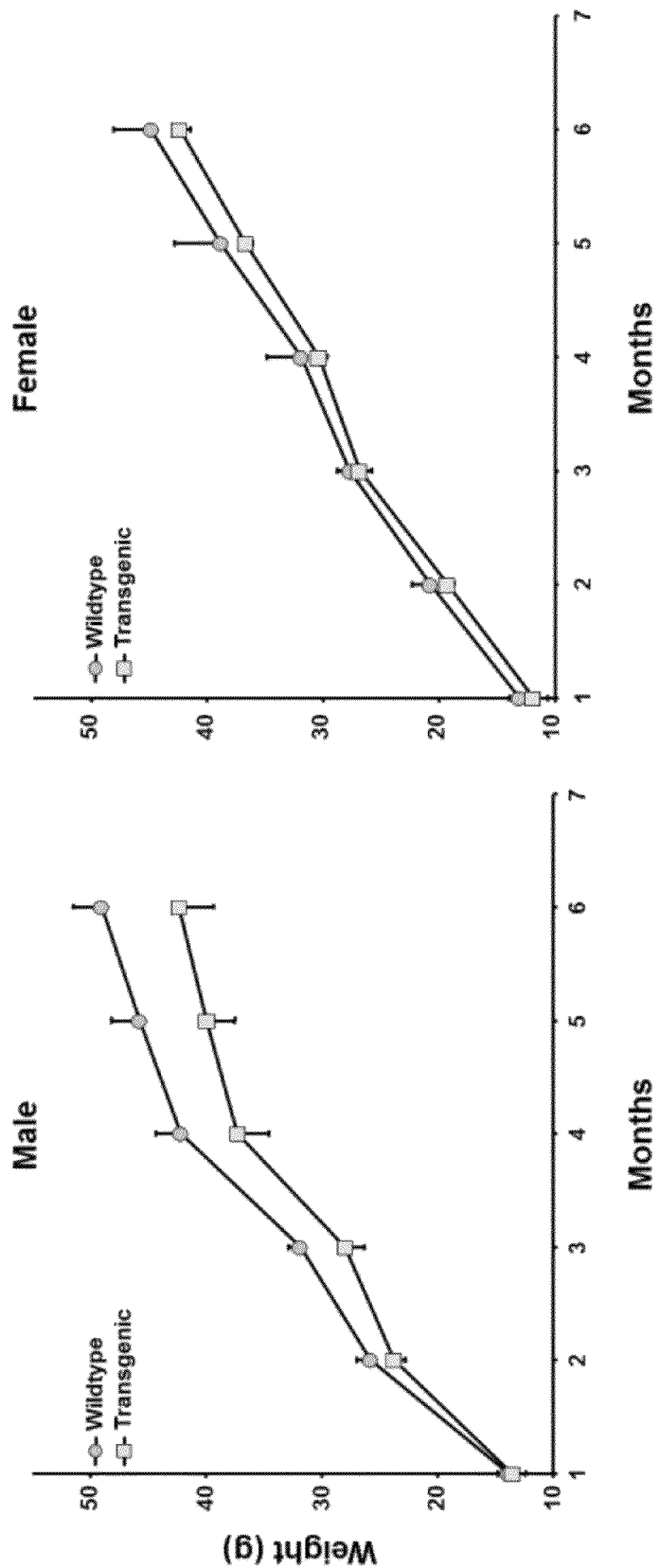
FIG. 11 depicts, in accordance with an embodiment herein, lymphoid transgenic weigh less than littermate WT mice.
Figure 12:
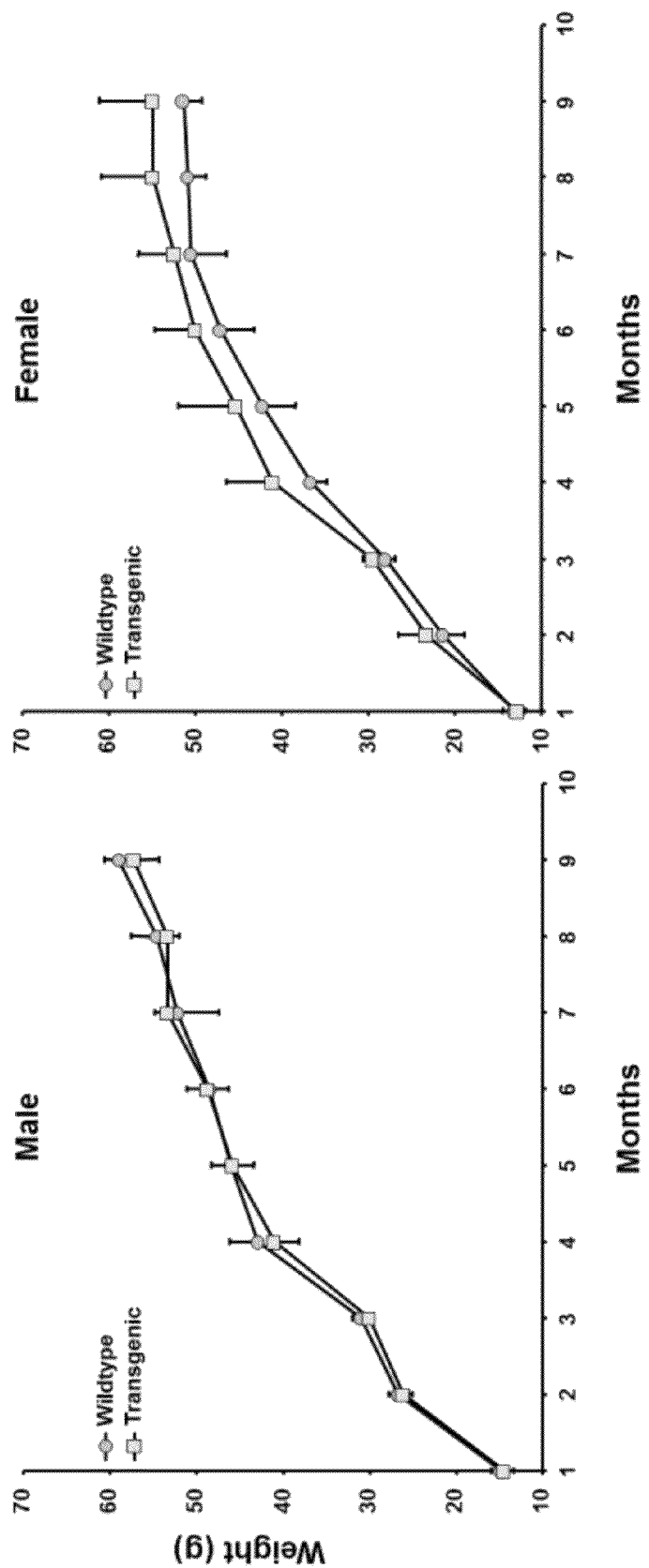
FIG. 12 depicts, in accordance with an embodiment herein, similar weight between WT and myeloid transgenic mice.
Figure 14:
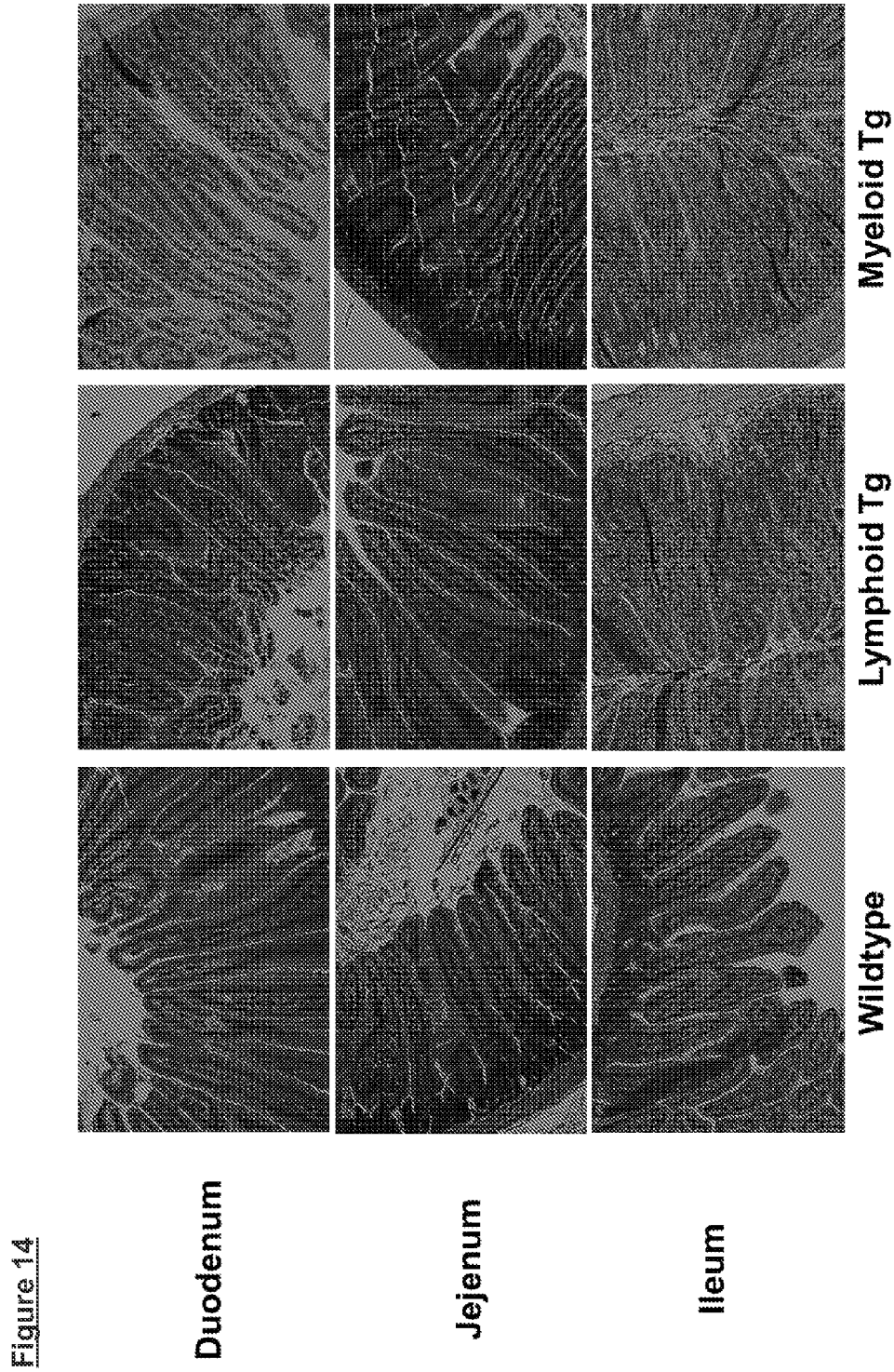
FIG. 14 depicts, in accordance with an embodiment herein, M-Tg and L-Tg transgenic mice have increased inflammatory infiltrate.
Figure 15:
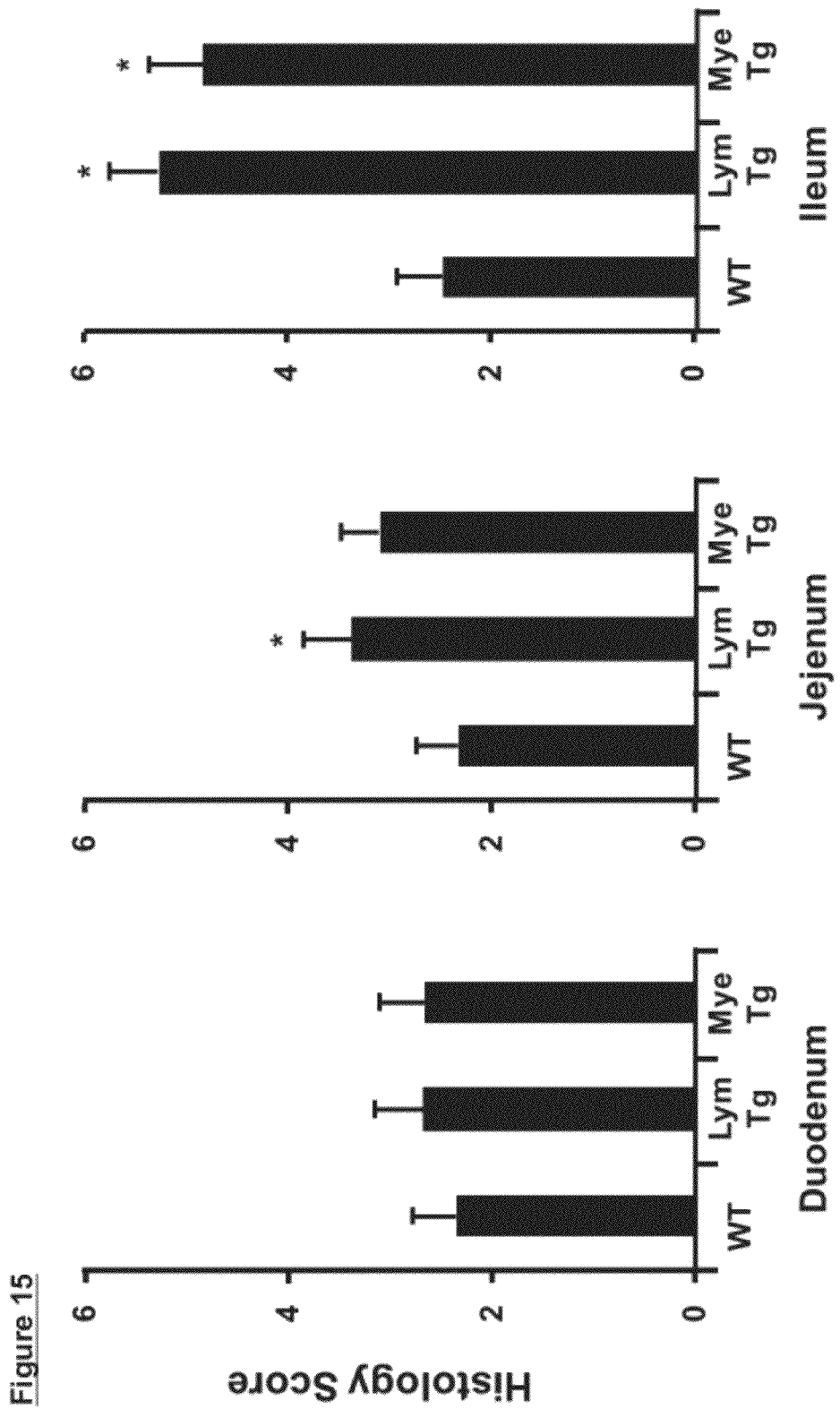
FIG. 15 depicts, in accordance with an embodiment herein, increased small bowel histology score in TL1A transgenic mice.

Lymphoid (FIG. 11), but not myeloid (FIG. 12), Tg mice are approximately 10% lighter in weight compared to WT littermates (FIGS. 11-13A), Overexpression of TL1A in lymphoid or myeloid cells did not alter the proportion of macrophages, dendritic cells, CD4+ or CD8+ T-cells. Compared to WT mice, lymphoid Tg mice showed increased chronic inflammation in the jejunum (score of 2.3 vs. 1.7) and ileum (score of 3.0 vs. 1.1) (FIGS. 14, 15). In myeloid Tg mice, increased chronic inflammation were observed only in the ileum compared to WT (2.3 vs. 1.1) (FIGS. 14, 15). The inventors did not observe any acute or chronic inflammation in the colon of Tg mice.

Figure 16:
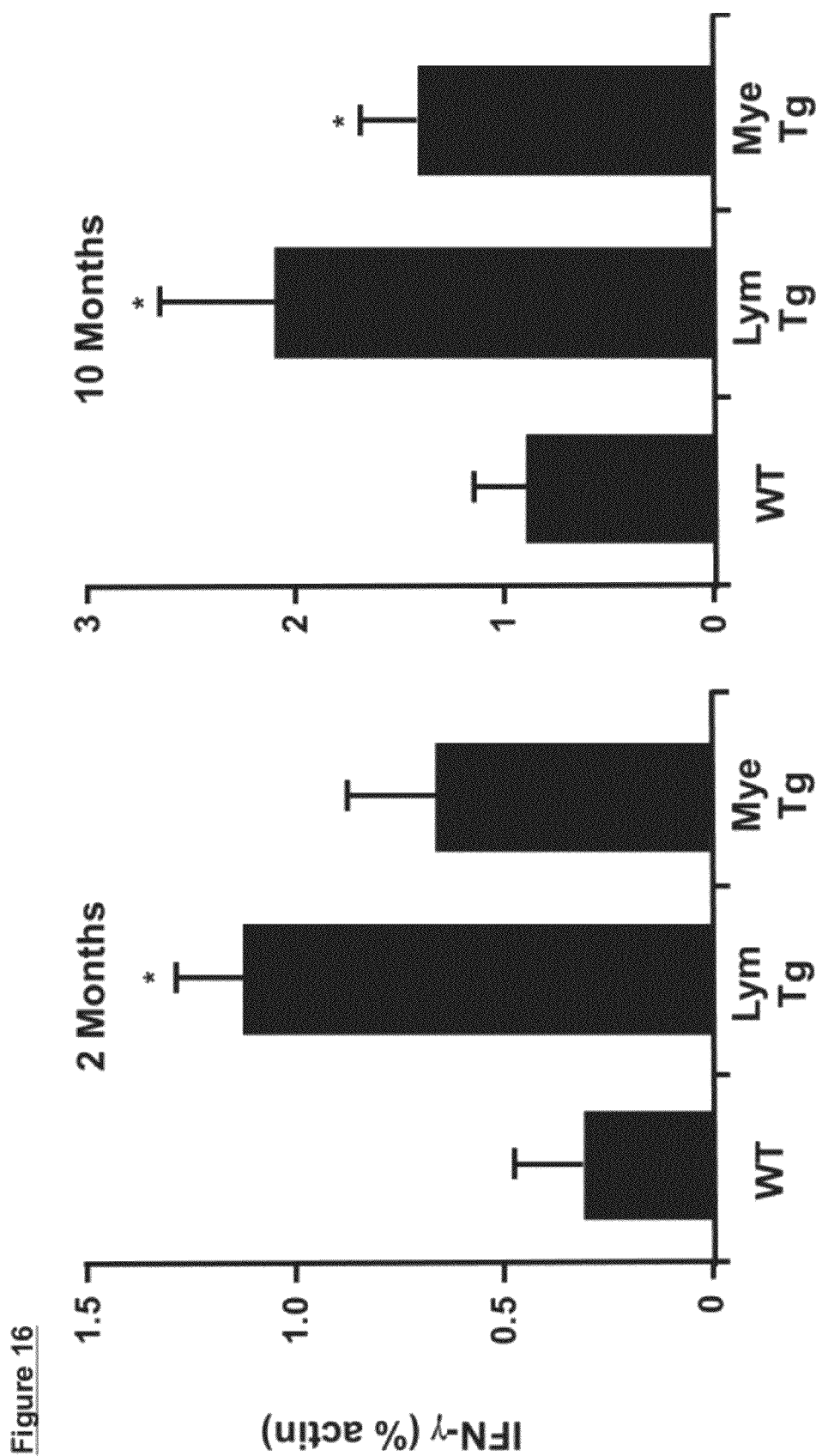
FIG. 16 depicts, in accordance with an embodiment herein, elevated IFN-γ expression in the ileum of TL1A transgenic mice.
Figure 17:
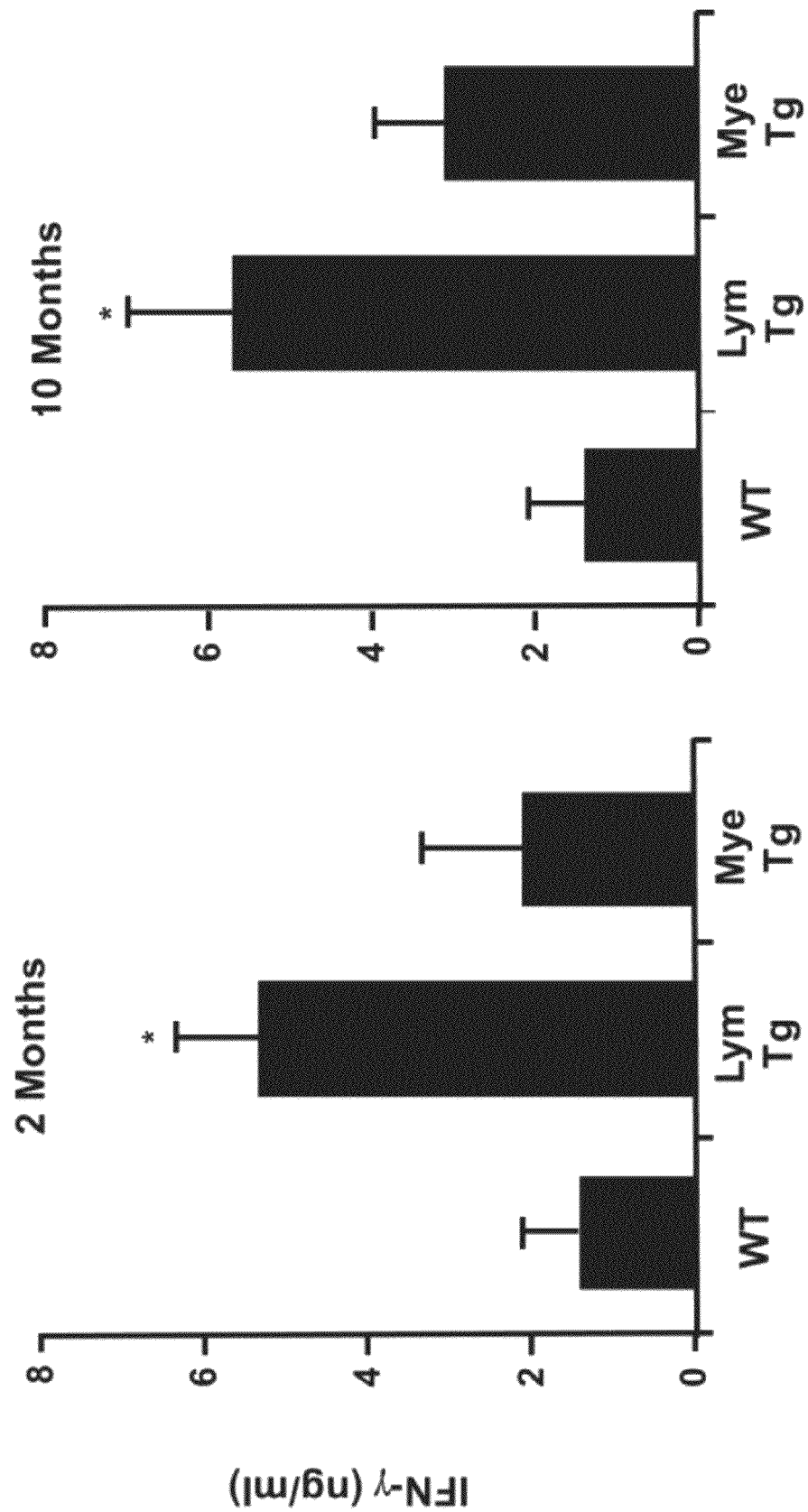
FIG. 17 depicts, in accordance with an embodiment herein, enhanced IFN-γ secretion in the MLN of TL1A. transgenic mice.

Using ELISA immunoassay to measure cytokine expression, the inventors observed increased expression of IFNγ, TNFα, IL17A and IL17F in the lymphoid L-Tg compared to WT mice at 2 and 10 months of age (3, 3, 15 fold increase in small bowel respectively at both time points) (FIGS. 16, 17).

In contrast, myeloid M-Tg mice exhibited increased IFN-γ, TNF-α, and IL-13 expression (approximately 7 fold increase for all cytokines) at 10 months; No elevation in these pro-inflammatory cytokines were observed at 2 months of age (FIGS. 16, 17).

Example 9

Figure 18:
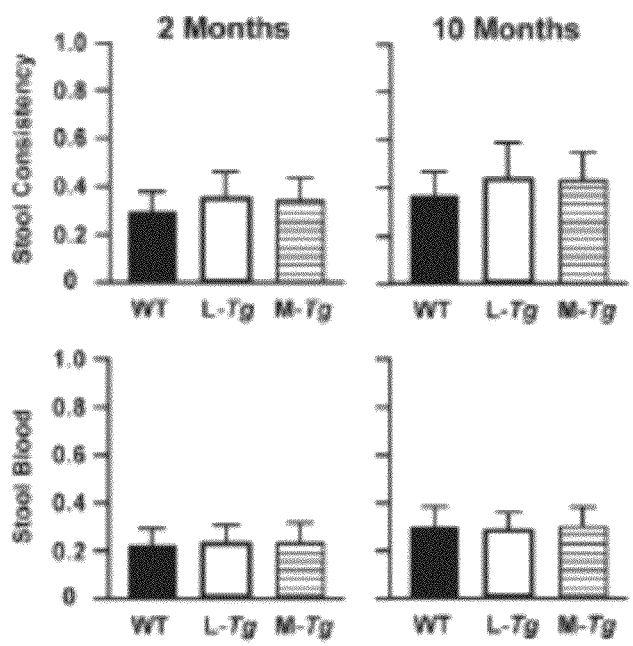
FIG. 18 depicts, in accordance with an embodiment herein, phenotypic characterization of TL1A Tg mice, (A) Stool consistency (top panels) and fecal blood (bottom panels) determined using standard methods from WT, L-Tg or M-Tg mice. [20] Data are expressed as mean±SD. N=20 per group, (B) Total number of cells isolated from spleen, MLN and lamina propria mononuclear cells (LPMC) from the colon and distal 10 cm of small intestine isolated from 10 months old WT (grey circle), L-Tg (black triangle) or M-Tg mice (open square) and represented as absolute cell number×$10^6$. Each data point represents an independent mouse.
Figure 18:
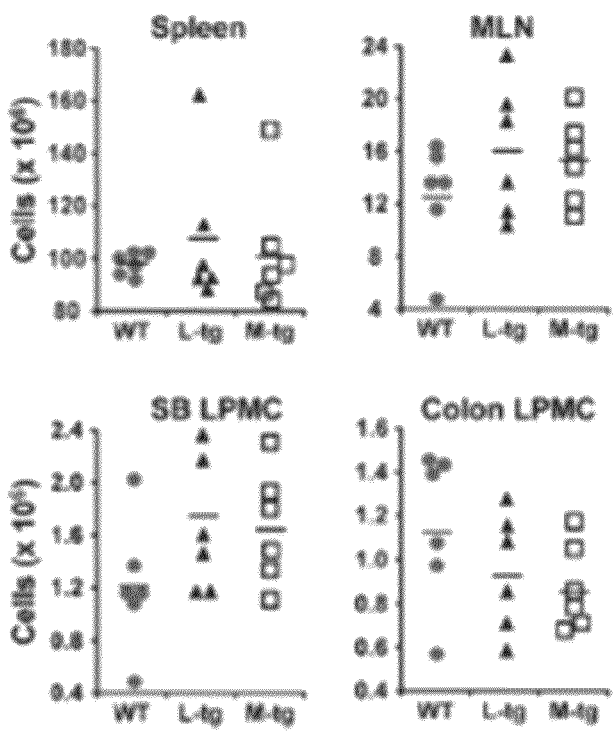

Disease Activity Index (DAI), Macroscopic and Histopathological Analysis Results There were no differences in the disease activity index (DAI) [20] between Tg and WT for up to 10 months. The inventors also did not observe differences in the splenic cell number. MLN cell number, lamina propria mononuclear cell (LPMC) number in the small bowel or colon, colon length, small bowel (SB) length or spleen size between WT and TL1A Tg mice at 2 or 10 months (FIG. 18B). There was a trend toward higher cell numbers in the MLN and SB LPMC in both sets of Tg mice. Stool consistency (top panels' and fecal blood (bottom panels) was determined using standard methods from WT, LCK-CD2-TL1A-GFP Tg (L-Tg) or FMS-TL1A-GFP Tg mice (M-Tg) mice [20] (FIG. 18A).

Example 10

Figure 19:
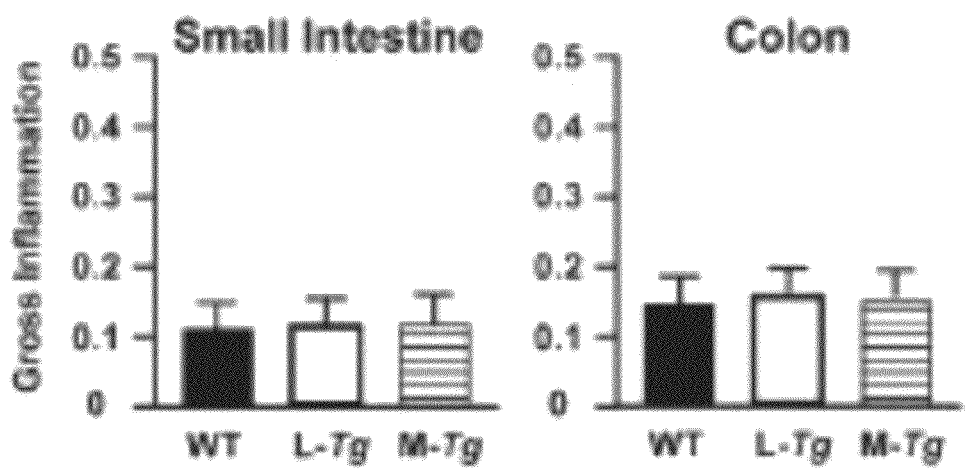
FIG. 19 depicts, in accordance with an embodiment herein, TL1A Tg mice do not develop gross intestinal inflammation but exhibit enhanced colonic fibrosis. (A) Gross appearance (wall thickening, hyperemia, rigidity or adhesions) of small intestine and colon are measured from 10 months old WT, L-Tg or M-Tg mice using a standard scoring system, [21] Data are expressed as mean±SD. (B) Myeloperoxidase (MPO) activity is measured on the distal 3 cm of ilea and mid-colon and data are expressed as arbitrary unit (U) per gram (g) of protein. *$p<0.05$ (C) Representative hematoxylin and eosin (H&E) stained colon section obtained from mid-colon of 10 month old WT, L-Tg or M-Tg mice are shown. (D) Masson Trichrome staining of collagen deposition in tissue sections of mouse mid-colon. Collagen is stained blue versus red background. There is increased blue collagen stain in L-Tg and M-Tg compared to WT littermate mice. Magnification 200×, Results are representative of six mice per group for A-D.
Figure 19:
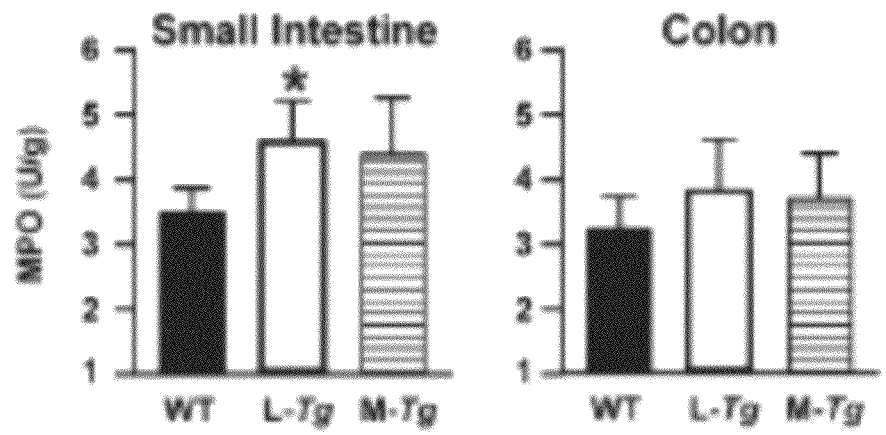
Figure 19:
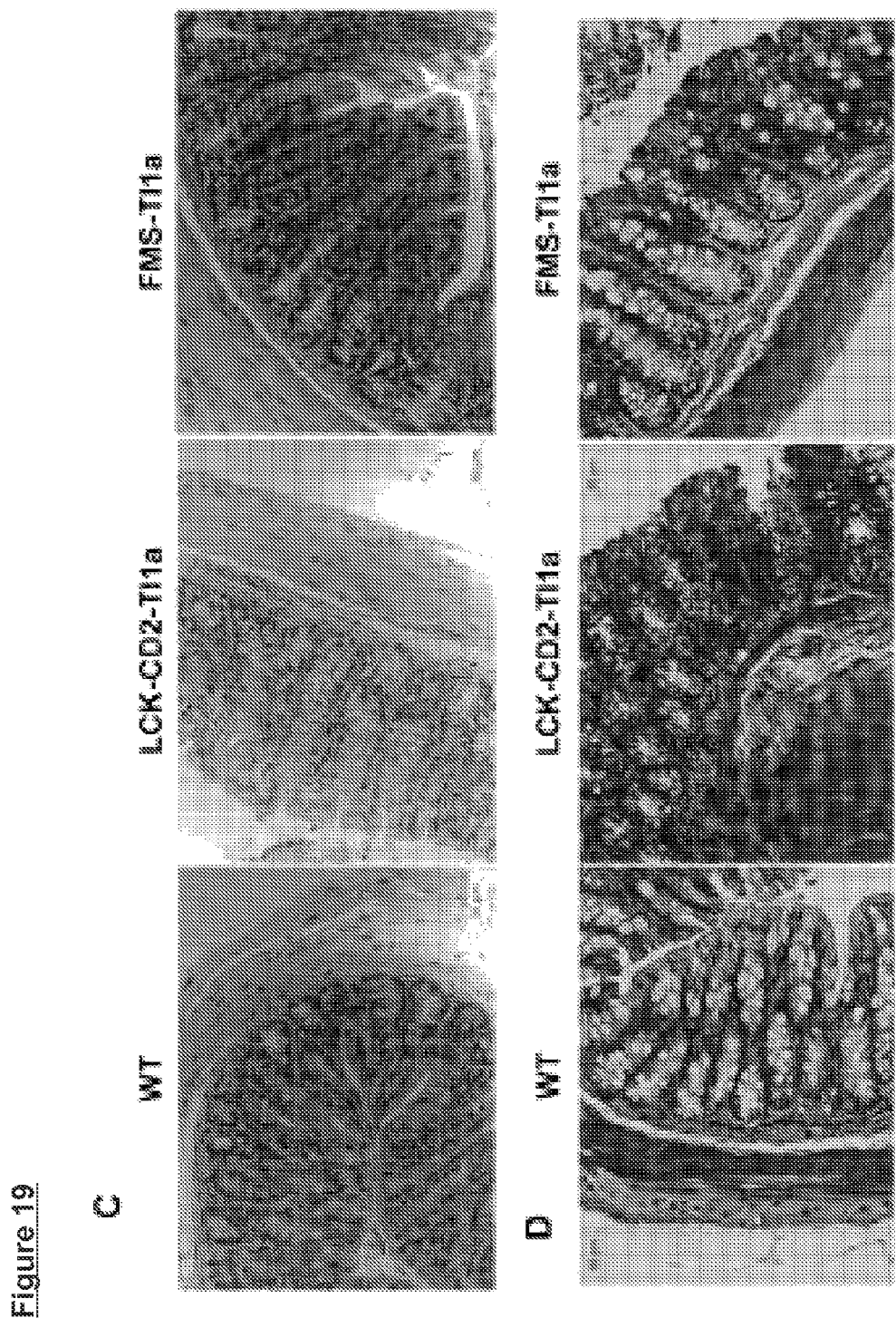

TL1A Expression in APC and T-Cells do not Develop Gross Tissue Inflammation, but Induce Mild Histologic Small Bowel Inflammation As elevated TL1A expression is implicated in gut mucosal inflammation and fibrosis, the inventors therefore investigated whether mice with elevated TL1A expression develop spontaneous colitis at 2 months and 10 months of age. The colon and small intestine did not show gross inflammation WT and Tg mice using a standard macroscopic scoring system [21] (FIG. 19 A).

However, another measure for gut inflammation is to determine myeloperoxidase (MPO) activity [22]. The inventors found significantly increased MPO activity in the small intestine of L-Tg mice than WT mice (FIG. 19B). By contrast, MPO activity was similar in the colon of WT and both M-Tg and L-Tg mice. Histological examination of the colon did not reveal increased inflammatory infiltrates (FIG. 19C), mucin depletion, epithelial cell hyperplasia, abnormal crypt architecture, crypt abscess or erosions in either WT or Tg mice at 2 or 10 months of age.

As elevated TL1A production in IBD patients is associated with fibrostenotic disease [23,24], the inventors assessed whether the TL1A Tg mice had increased histologic fibrosis. Notably, the inventors observed increased fibrosis in the colonic mucosa and submucosa of both LCK-CD2- and FMS-TL1A Tg mice as compared to WT littermate mice by 10 months of age using the Masson Trichrome stain (FIG. 19D).

Figure 20:
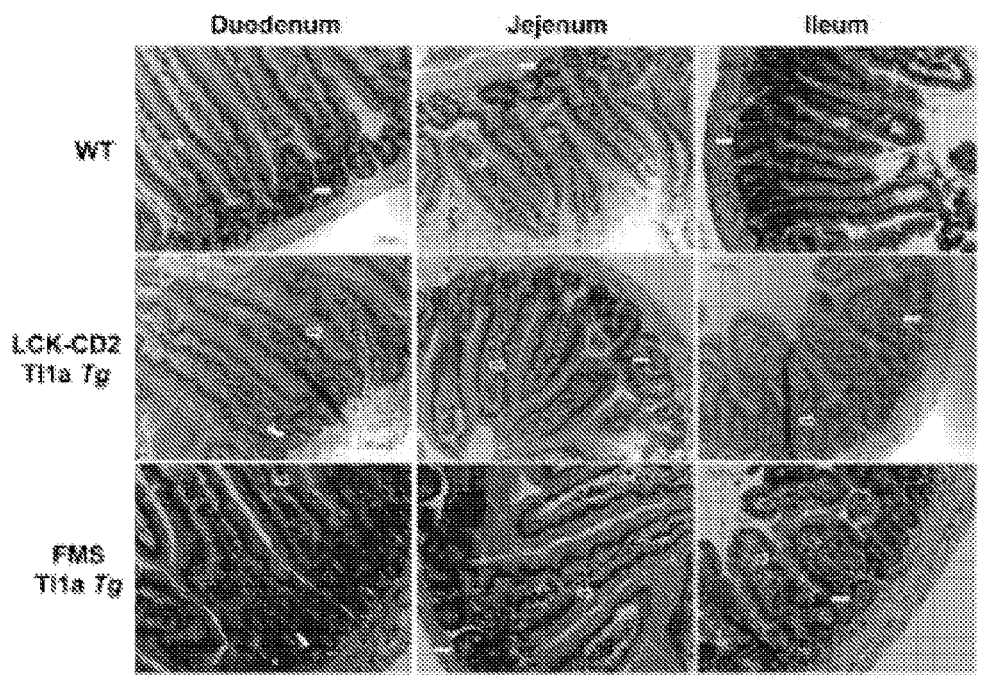
FIG. 20 depicts, in accordance with an embodiment herein, constitutive TL1A expression leads to increased numbers of goblet and Paneth cells in the small intestine and ileal histological inflammation. (A) Representative H&E stained sections obtained from the indicated portions of small intestine from 2 month old WT, L-Tg or M-Tg mice are shown. Goblet-cells are denoted by an open arrow, Paneth cells are denoted by a filled arrow. Results are representative of six mice per group. Magnification 200×. (B) The numbers of goblet (top panel) and Paneth cells (middle panel) determined by examining at least 80 individual villi at the indicated portions of the small intestine from six mice (2 months old) per group by 2 observers blinded to mouse genotype. Data are expressed as mean±SD. Histologic scores (bottom panel) determined by 2 observers blinded to mice using standard methods. [21] Data are expressed as mean±SD. At least 36 fields from 6 mice per group at 200× magnification were scored. *$p<0.05$, **$p<0.01$.
Figure 20:
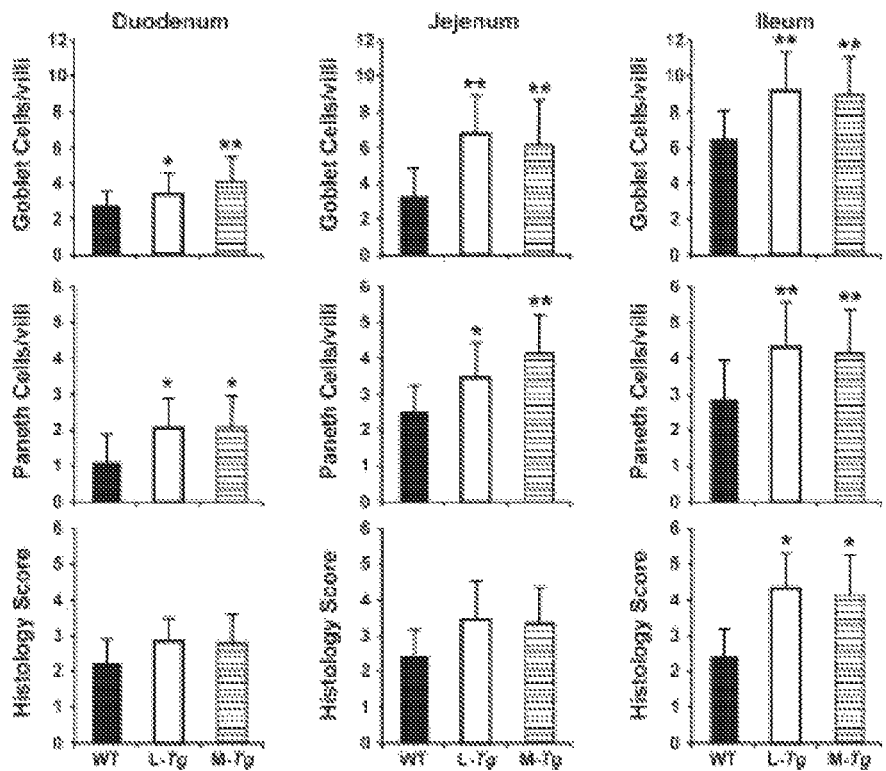

At 2 months of age, histological examination of the small intestine revealed a significant increase in the number of goblet-cells and Paneth cells (FIG. 20A), There was blunting of the villi and increased LPMC in the ileum of both the M-Tg and L-Tg mice compared to WI mice. These histological changes reflected by a significant increase in the inflammatory score in the ileum of TL1A Tg mice using a standard quantitative scoring system (FIG. 20B). [21] The inventors did not observe villus blunting nor increased mononuclear cells in the LP of the duodenum and jejunum between WT and TL1A Tg mice at 2 months of age.

Figure 21:
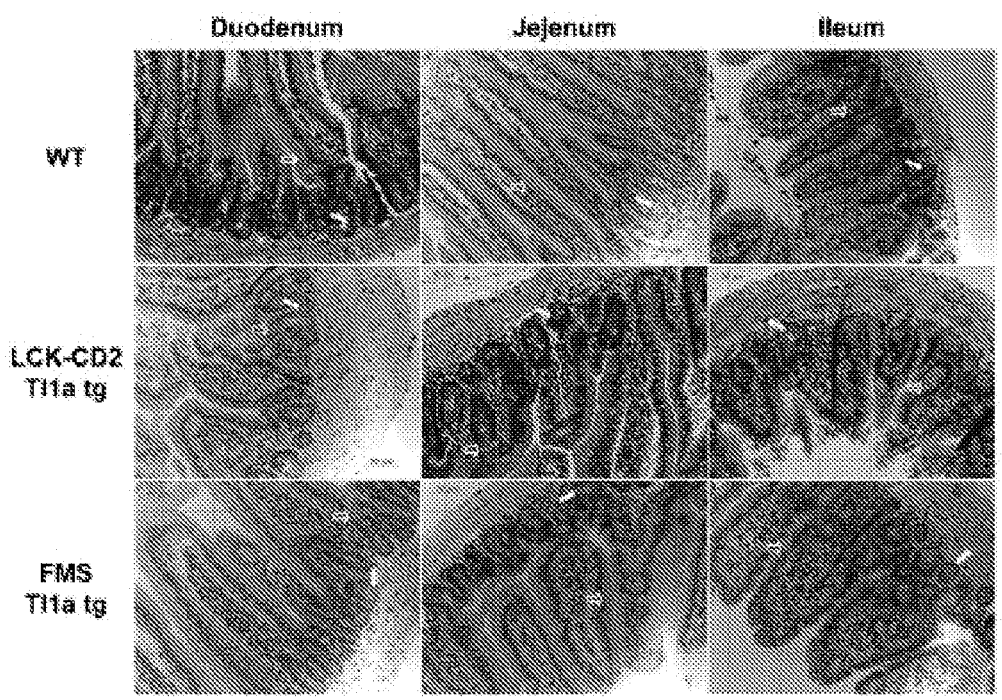
FIG. 21 depicts, in accordance with an embodiment herein, persistent Paneth cell hyperplasia and worsened small intestinal inflammation as the TL1A Tg mice aged. (A) Representative H&E stained section Obtained from the indicated portions of small intestine from 10 month old WT, L-Tg or M-Tg mice are shown. Goblet-cells are denoted by an open arrow, Paneth cells are denoted by a filled arrow. Results are representative of six mice per group. Magnification 200×. (B) The numbers of goblet (top panel) and Paneth cells (middle panel) determined by 2 observers blinded to mice genotype. Histologic scores (bottom panel) determined from 10 month old WT, L-Tg, or M-Tg mice using standard methods. [21] Quantification of goblet and Paneth cells was determined by examining at least 80 individual villi and histological scores determined by examining at least 36 fields at 200× magnification. Six independent mice per group used (A-B). Data are expressed as mean±SD. *$p<0.05$, **$p<0.01$.
Figure 21:
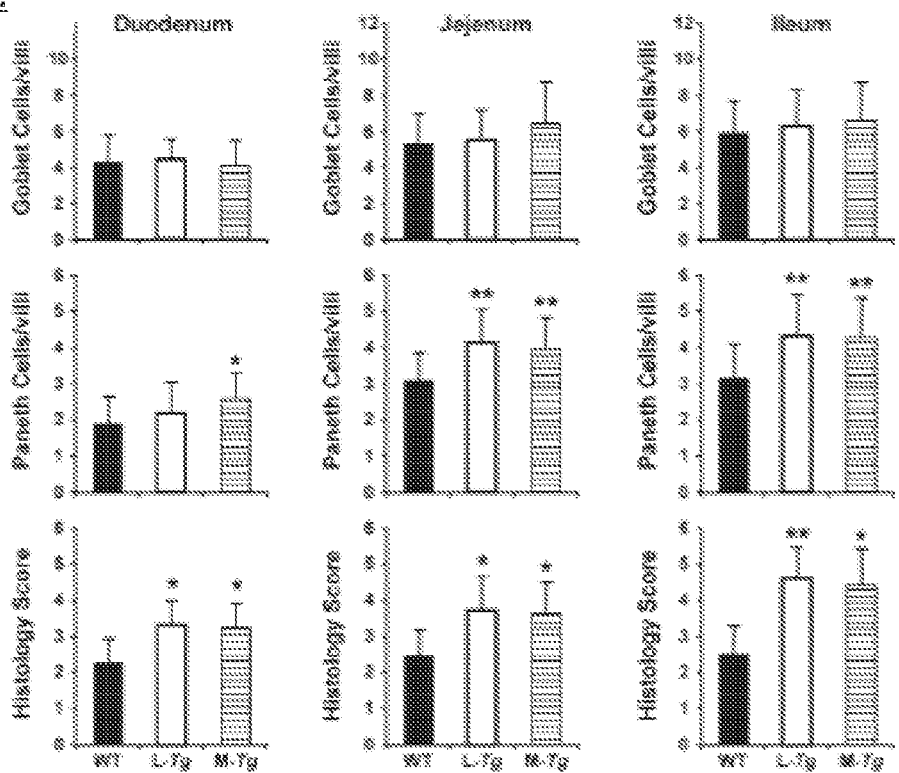
Figure 22:
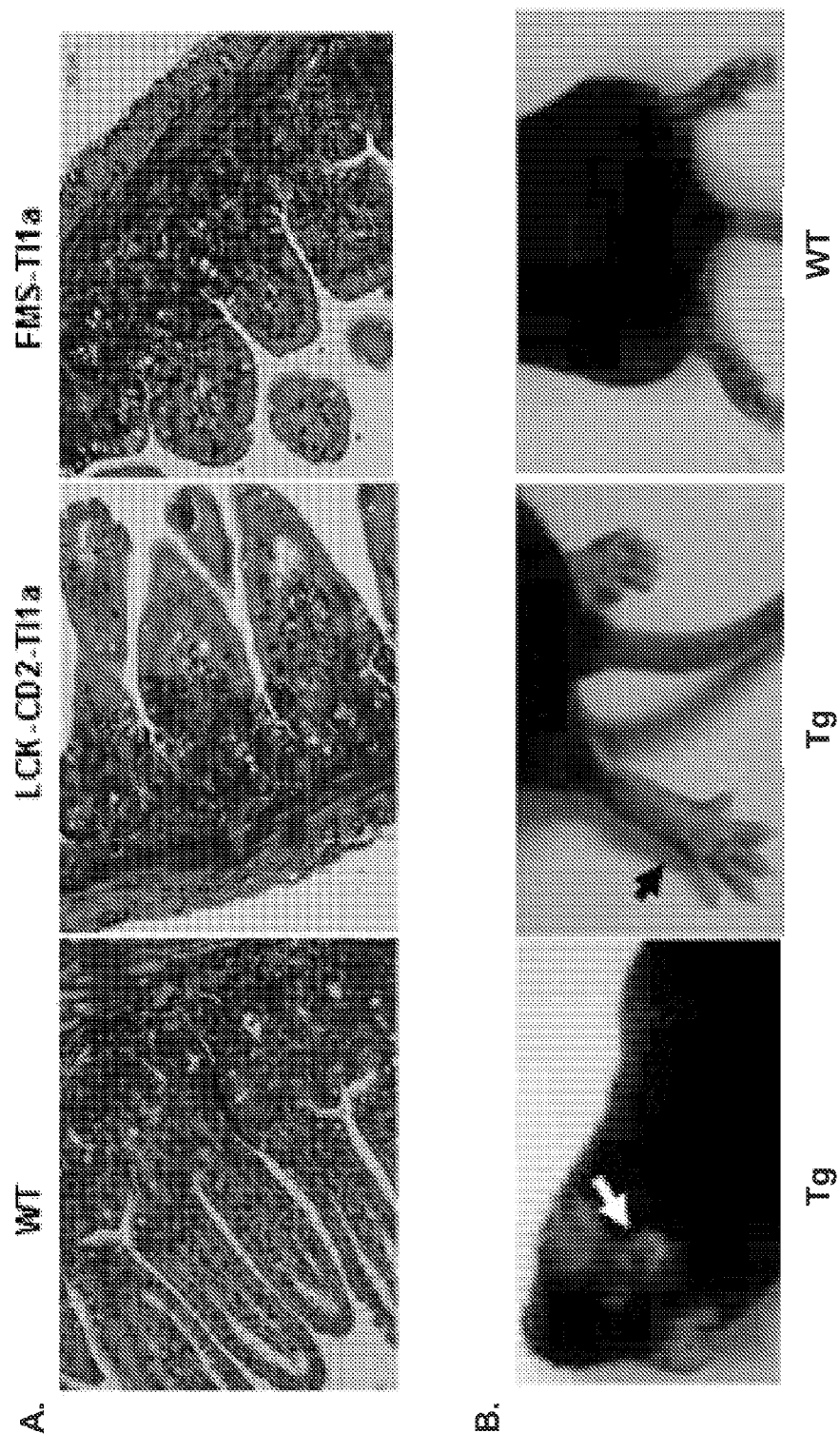
FIG. 22 depicts, in accordance with an embodiment herein (A) increased fibrosis in the small intestine of TL1A Tg mice. Masson Trichrome staining was performed on mice ileal sections (distal 3 cm of small intestine). There is increased blue collagen stain in L-Tg and FMS-TL1A Tg compared to WT littermate mice. Magnification 200×, Six independent mice per group used. (B) TL1A. transgenic mice develop ulcerated skin lesions and arthropathy. A typical ulcerated skin lesion is illustrated (white arrow, top). Erythematous arthropathy found in the transgenic (Tg) mice is shown (black arrow, middle). A WT joint is shown in the bottom panel for comparison. Fibrostenosis is also readily apparent, as shown by (C) WT mice, with bile duct and inflammatory cells marked, and (D) transgenic TL1A mice, demonstrating more inflammation around the bile ducts and portal triads in the transgenic TL1A mice as compared to WT mice. Additionally, in (E) WT mice, and (F) transgenic TL1A. mice, more fibrosis in the bile ducts and portal triads appears in the transgenic TL1A mice as compared to the WT.
Figure 22:
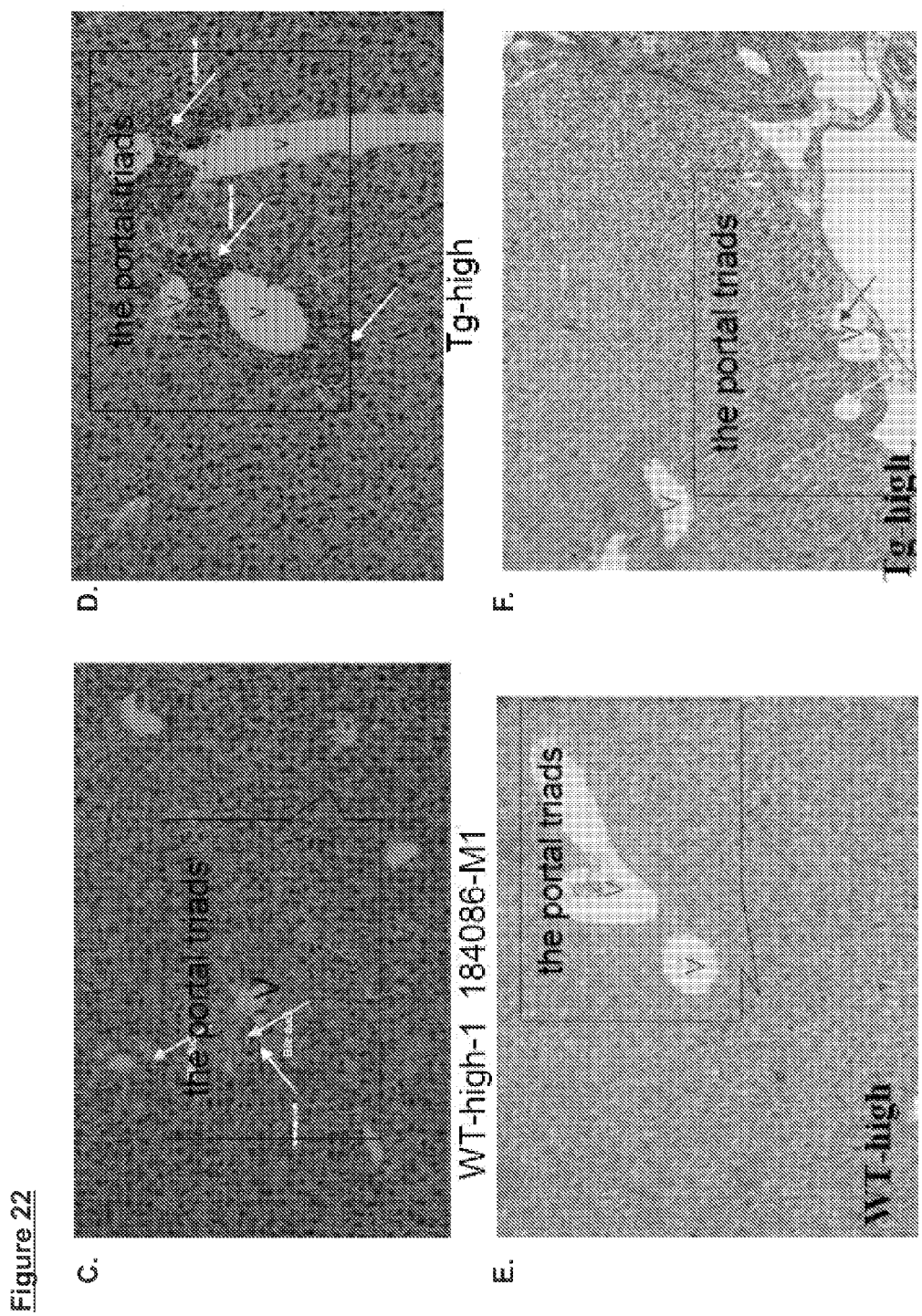

At 10 months, the inventors similarly observed Paneth cell hyperplasia in both L-Tg and M-Tg mice compared to WT mice (FIGS. 21A, 22A). In contrast to younger mice (2 months of age), there were no detectable differences in the number of goblet-cells of WT and Tg mice at 10 months of age (FIG. 21B), The inflammatory changes in the small intestine such as increased mononuclear cell infiltrate of the LP and blunting of the villi was more prominent and progressive, involving the duodenum, jejunum and ileum (FIG. 21A), The increased inflammation in both M-Tg and L-Tg mice was associated with increased histologic fibrosis by the more extensive Masson Trichrome stain in the small intestine. Together, these results indicated that constitutive expression of TL1A in T-cells and myeloid cells lead to progressive spontaneous intestinal inflammation and fibrosis.

Example 11

Mice with Constitutive TL1A Expression Develop Extra-intestinal Pathology

At a low frequency, the inventors observed extra-intestinal pathology in both the M-Tg and L-Tg mice (FIG. 22B). One such feature was an erythematous ulcerated skin lesion that was observed in 1 out of 58 FMS-TL1A Tg, 2 of 51 L-Tg and 1 out of 155 WT littermate mice. Another observed pathology was joint erythema that caused movement difficulties and resulting in mice unable to feed. Arthropathy was observed in 2 out of 58 M-Tg, 2 out of 51 L-Tg mice and 0 out of 155 WT mice. Three out of 4 Tg mice with arthropathy had monoarticular disease and 1 L-Tg mouse had polyarticular disease. The data demonstrates these novel murine models with constitutive expression of TL1A in APC and T-cells develop extraintestinal pathology, such as ulcerated skin lesion and arthropathy.

Example 12

Accelerated T-cell and APC Activation in L-Tg and M-Tg Mice

To assess whether constitutively expressed TL1A can costimulate T-cells in vivo, the inventors compared the expression of an activation marker on CD4+ and CD8+ cells between Tg and WT littermate controls. CD4+ CD45RB$^{low}$CD25+ T$_{reg}$ cells were gated out in order to examine the expression of activation markers on conventional T-cells.

Figure 23:
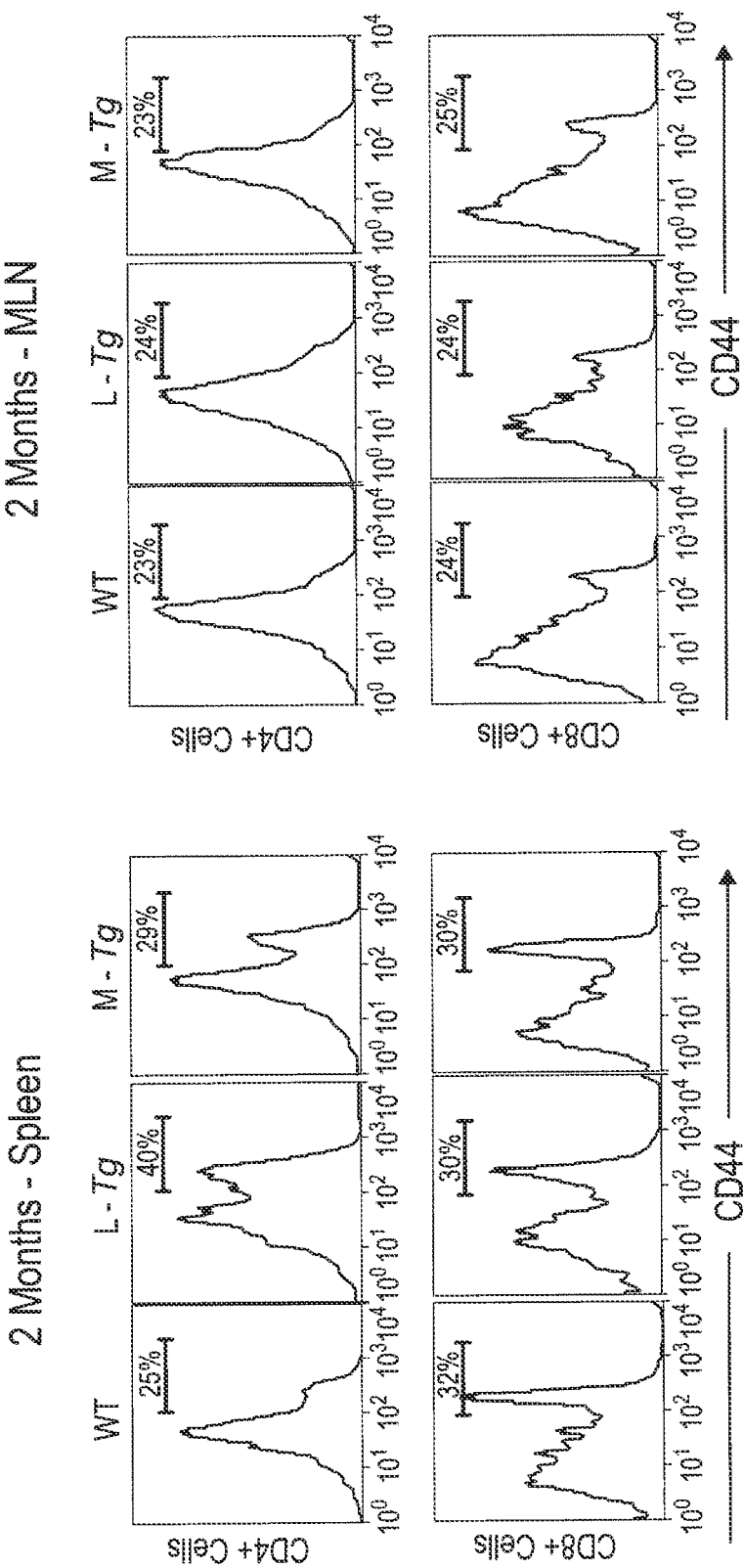
FIG. 23 depicts, in accordance with an embodiment herein, sustained TL1A expression leads to an increased percentage of activated T-cells. FACS plot of 2. month (A) and 10 month (B) splenocytes and MLN cells showing expression of activation markers CD4+. Either CD4+ or CD8+ cells are gated as indicated. Data shown are representative of 4 mice per group for WT ("WT"), L-Tg, and M-Tg mice.
Figure 23:
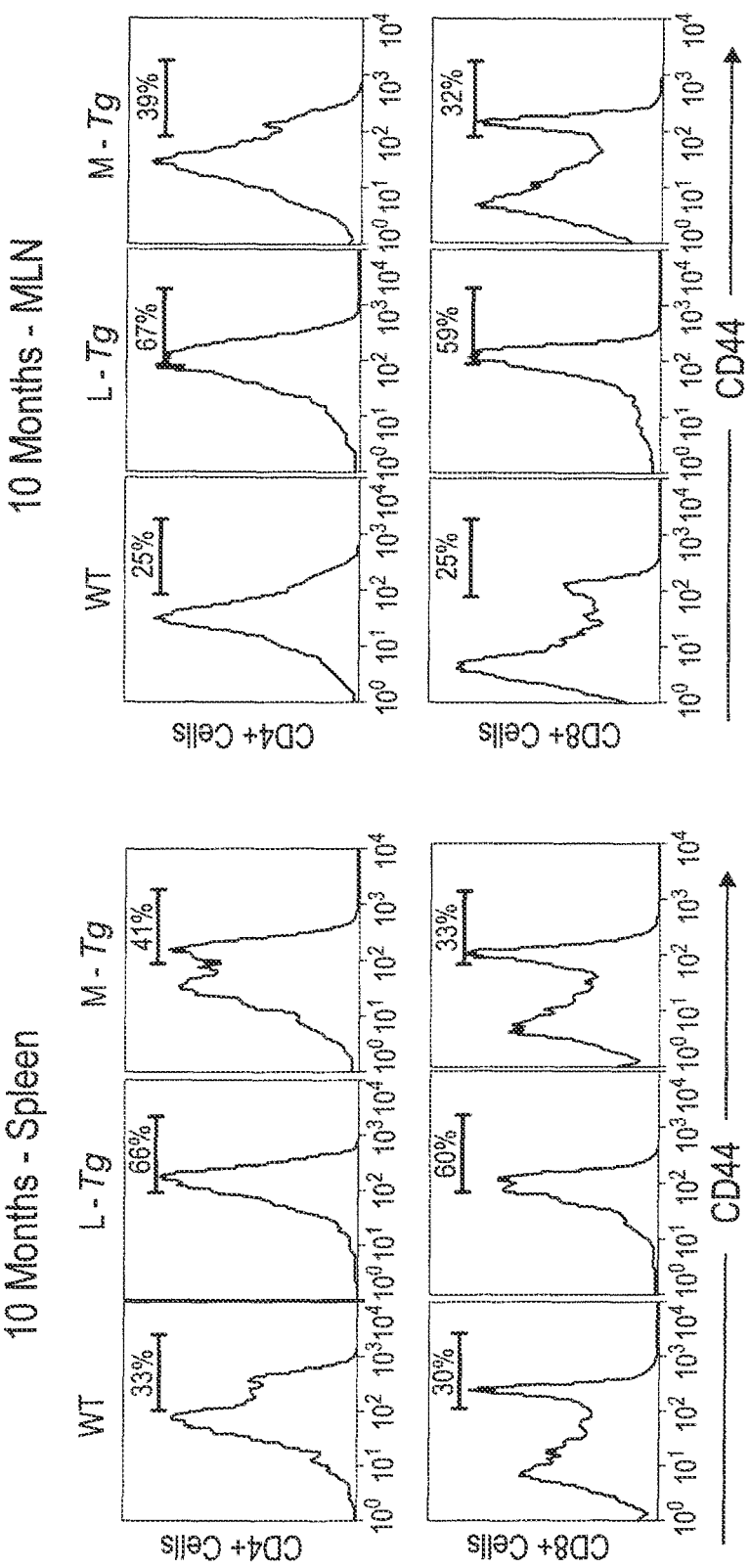

For L-Tg mice, at 2 months, there was almost 2 fold higher CD4+ CD44+ T-cells from the spleen, but not MLN of L-Tg mice (FIG. 23A). There was also no difference in the expression of the activation marker CD44 on CD8+ T-cells in the MLN and spleen at 2 months of age between TL1A. Tg mice and WT littermates, By 10 months of age, a higher percentage of TL1A Tg CD4+ cells in both the spleen and MLN expressed the activation marker CD44, particularly in the L-Tg mice (FIG. 23B). In contrast, only CD8+ cells from the L-Tg, but not M-Tg, spleen and MLN exhibited an increased expression of the activation marker CD44.

Figure 24:
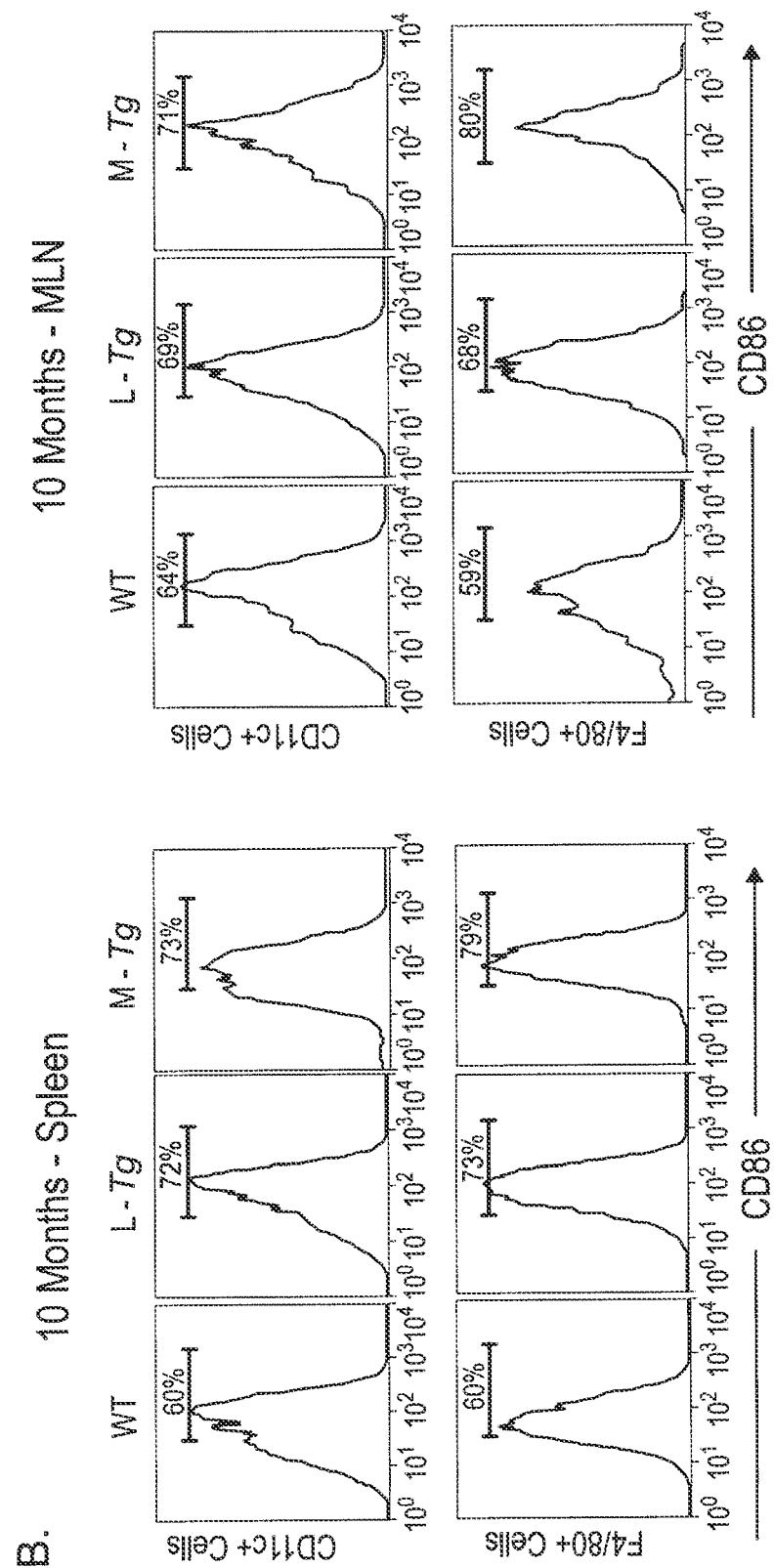
FIG. 24 depicts, in accordance with an embodiment herein, sustained TL1A expression leads to an increased percentage of activated DC and macrophages. FACS plot of 2 month (A) and 10 month (B) splenocytes and MIA cells showing expression of activation markers CD8+. Either F4/80+ or CD11c+ cells gated as indicated. Data shown are representative of 4 mice per group for WT WT, L-Tg, and M-Tg mice.

For M-Tg mice, the expression of the activation marker CD86 was compared between TL1A Tg and WT littermate controls to assess the effect of constitutive TL1A expression on the activation state of DC and macrophages (FIG. 24). Flow cytometric (FACS) analysis revealed. increased CD86+ expression on DC (CD11c+) and macrophages (F4/80+) in both the spleen and MLN of TL1A Tg mice compared to WT mice. In contrast to L-Tg mice, there was a negligible further increase in the percentage of activated DC and macrophages over time (compare 2 and 10 months). These data demonstrated that sustained TL1A expression could result in enhanced activation of CD4+, CD8+, DC and macrophages in vivo.

Example 13

Constitutive in vivo TL1A Expression Leads to an Increased Number of T-cells Expressing T$_{reg}$ and Gut Homing Markers FACS analysis did not eveal any differences in the frequencies of CD3+, CD4+, CD8+, MHCII+, CD11c+ or F4/80+ cells in the spleen and MLN among M-Tg, L-Tg or WT littermate mice.

Figure 25:
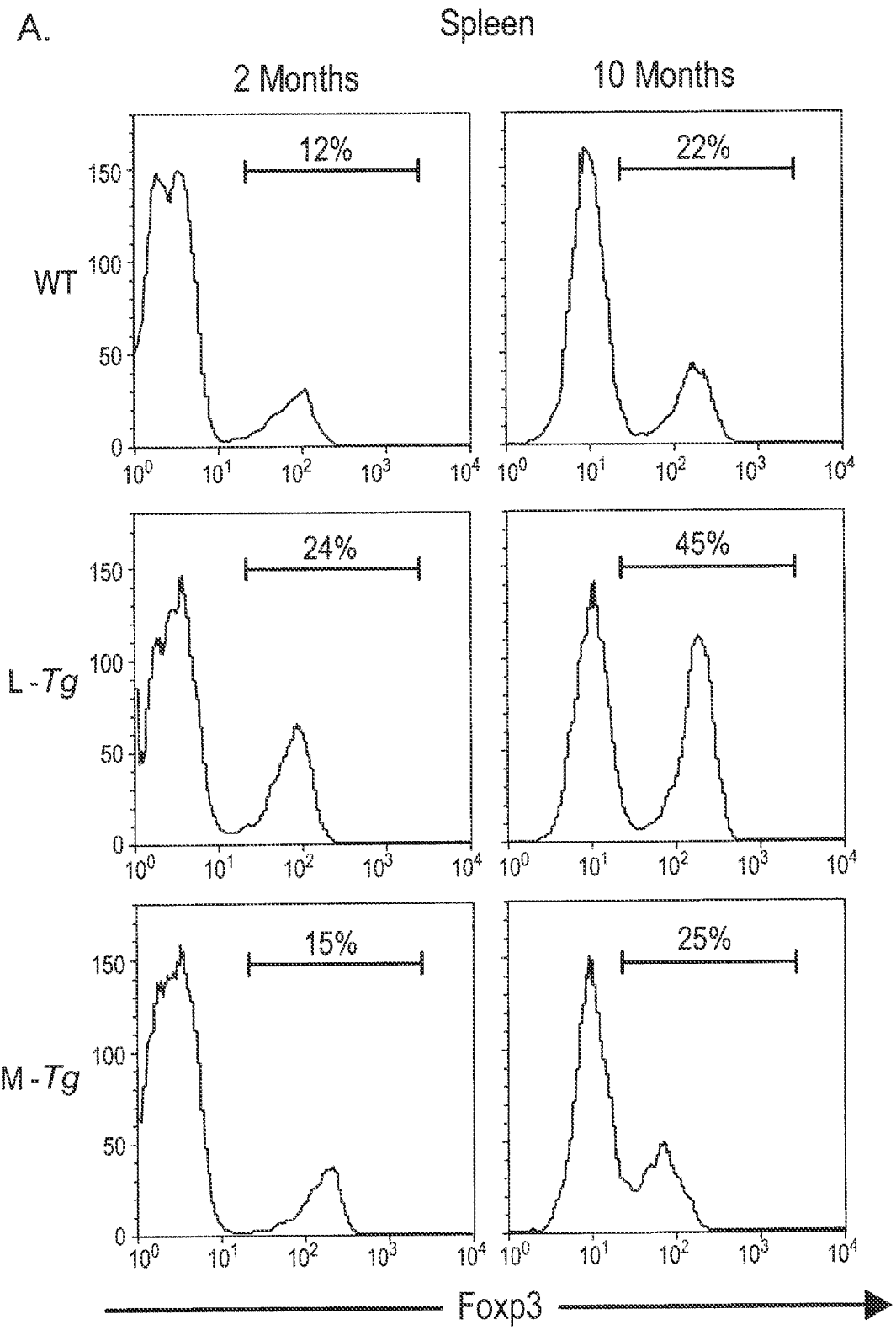
FIG. 25 depicts, in accordance with an embodiment herein, increased numbers of regulatory T ($T_{reg}$) cells in TL1A Tg mice. FACS plot of CD4+ Foxp3+ splenocytes (A) or CD4 +Foxp3+ MLN cells (B) are shown. Data shown are representative of 4 mice per group at either 2 or 10 months of age for WT WT, L-Tg, and M-Tg mice.
Figure 25:
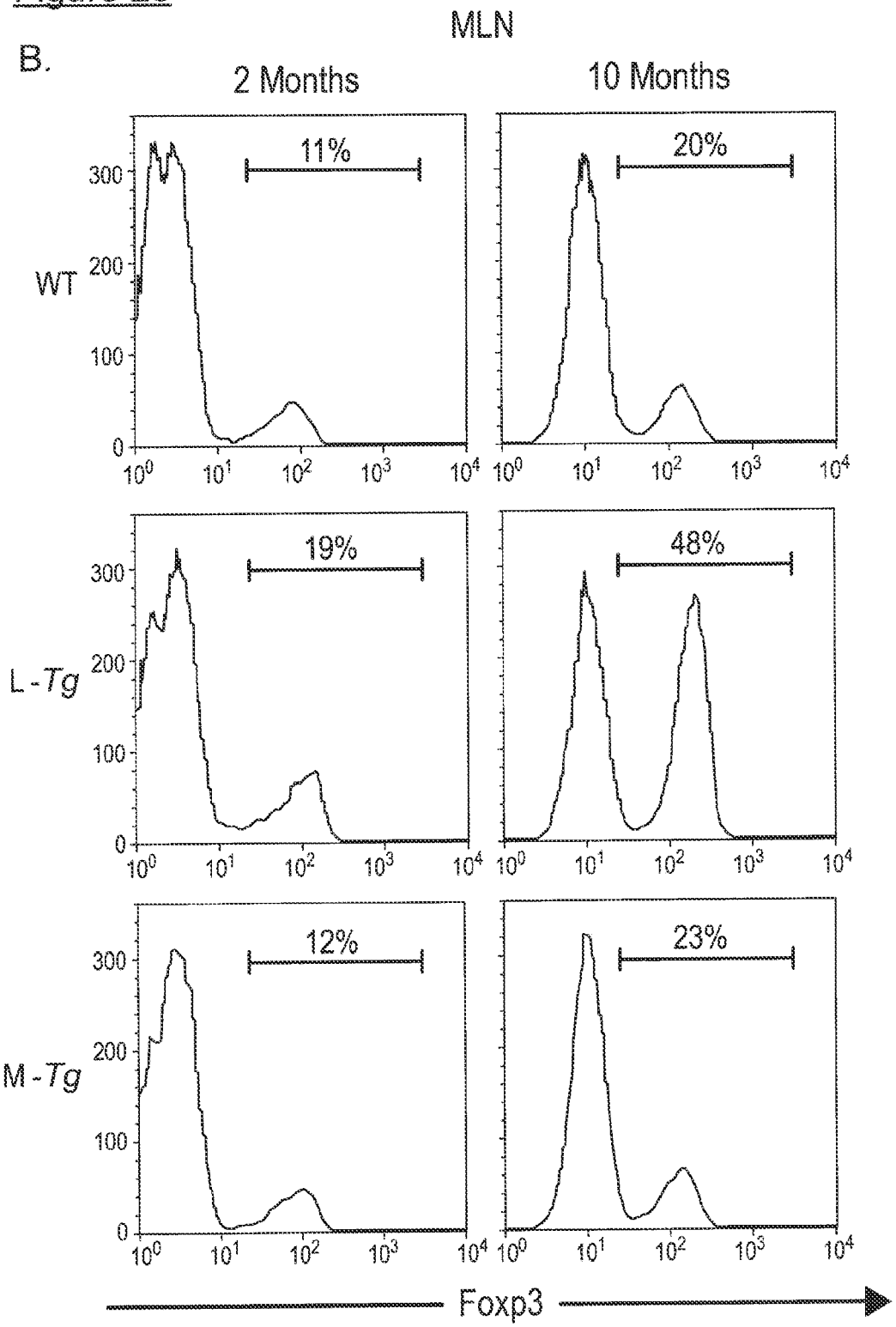

There was an increase in the frequency of Foxp3 positive cells in the spleen (FIG. 25A) and MLN (FIG. 25B) of L-Tg mice. The percentage of Foxp3+ cells further increased as the L-Tg mice aged. By contrast, there was no difference in the frequency of Foxp3+ cells in the spleen or MLN of M-Tg mice at both 2 and 10 months. A trend toward a higher cell number in the MLN and small bowel LPMC was noted in older animals.

Figure 26:
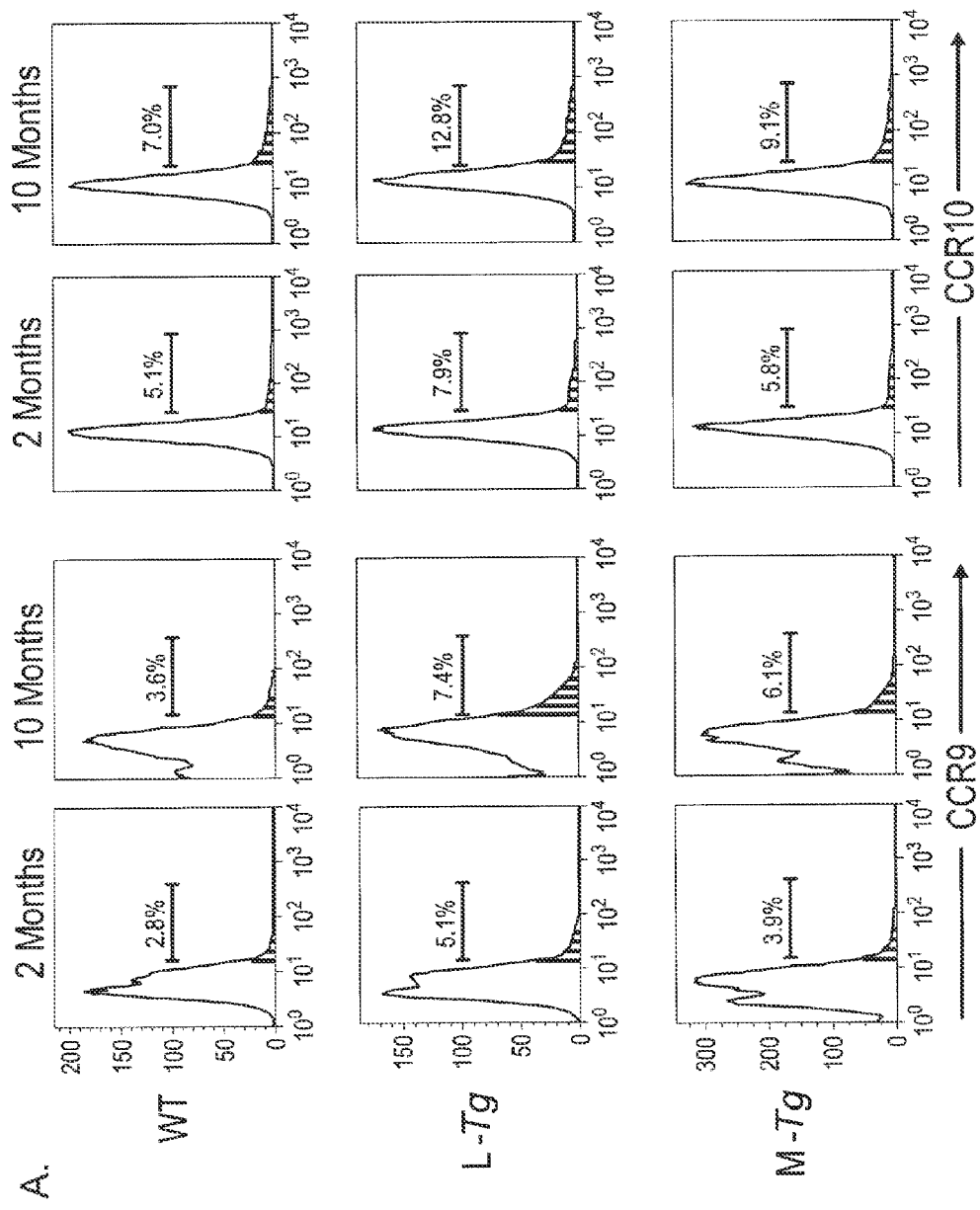
FIG. 26 depicts, in accordance with an embodiment herein, increased expression of gut homing markers and IFN-γ in TL1A Tg mice. (A) FACS plots showing expression of gut homing markers CCR9 and CCR10 on CD4+ cells isolated from the MLN. (B) FACS plot of gated CD4+ cells from MLN and stained for intracellular IFN-γ, IL-17, and IL-13 expression from 10 month old WT WT, IL-Tg or M-Tg mice. Data shown are representative of 4 mice per group (A and B). Black bars indicate area under the curve that is gated as CCR9 positive cells for WT WT, L-Tg, and M-Tg mice.
Figure 26:
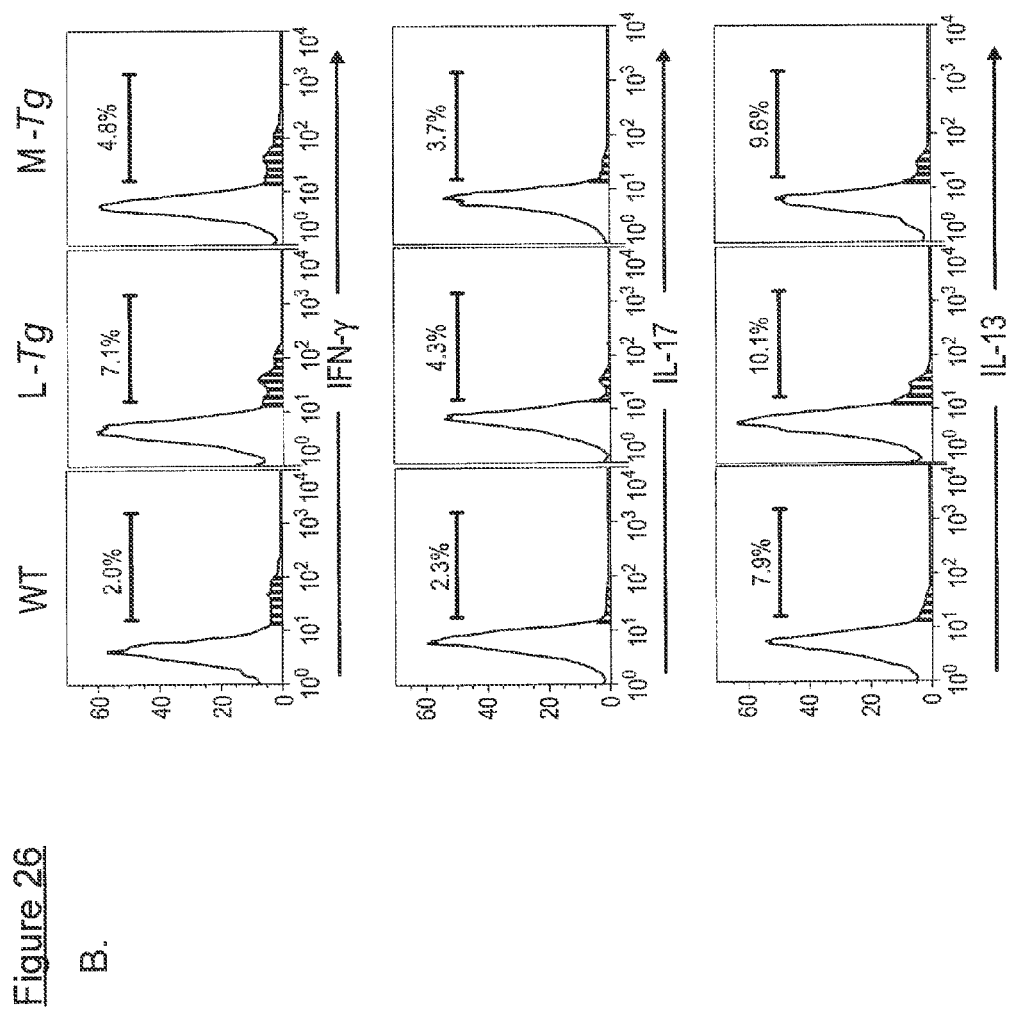

To determine whether this finding was due to increased trafficking to the gut immune compartment, the inventors assessed the expression of the gut homing markers CCR9 and CCR10 in the MLN and spleen of TL1A Tg and WT littermate mice (FIG. 26A). In the spleen, there was no difference in CCR9+ or CCR10+ cells at 2 or 10 months between either TL1A Tg or WT mice. However, the inventors discovered an increase in the percentage of cells expressing CCR9 and CCR10 in the MLN of L-Tg mice compared to WI mice at 2 months and the difference became even greater as the mice aged. For the FMS-TL1A Tg mice, a higher percentage of CCR9+ and CCR10+ cells was observed at 10 months, but not at 2 months.

Example 14

TL1A Tg Mice have an Enhanced Pro-inflammatory Cytokine Profile in the MLN and Small Intestine Having established increased expression of activation and gut homing markers, the inventors further measured the expression of pro-inflammatory cytokines such as IFN-γ, IL-13 and IL-17 by FACS analysis and ELISA.

At 2 months of age, there was no difference in the expression of CD4+, IFN-γ, CD4+, IL-13+, CD4+, IL-17+ T-cells by either FACS, intracellular stain or ELISA in M-Tg, L-Tg or WI littermate mice.

Figure 27:
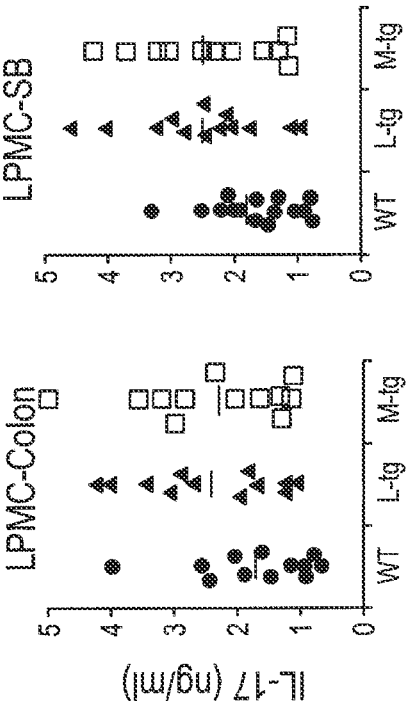
FIG. 27 depicts, in accordance with an embodiment herein, cytokine profile of W17, L-Tg, and M-Tg littermate mice. IFN-γ (A), IL-17 (B), IL-13 (C) and IL-10 (D) secretion after stimulation with anti-CD3 and anti-CD28 assessed by enzyme-linked immunosorbent assay (ELISA). Each data point (A)-(D) represents cytokine expression for either splenocytes, MLN cells or lamina propria mononuclear cells (LPMC) from either the colon or the distal 10 cm of small intestine isolated from an individual mouse. p-values are indicated the figure where significant.
Figure 27:
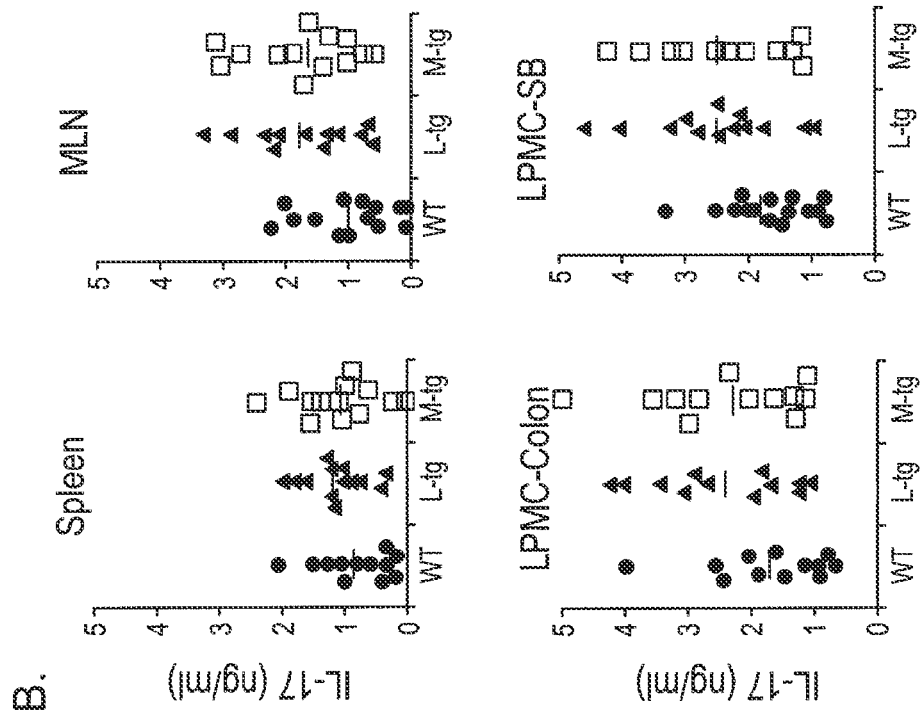
Figure 27:
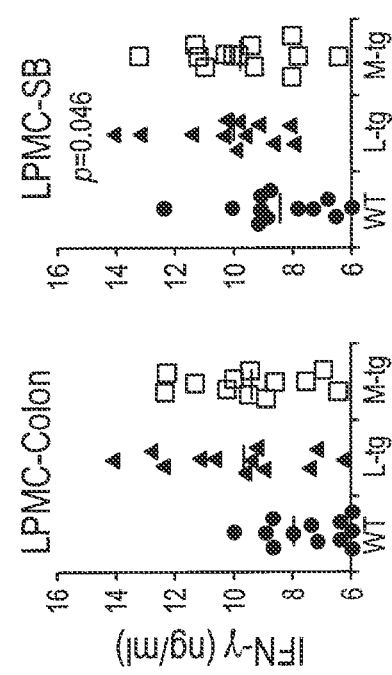
Figure 27:
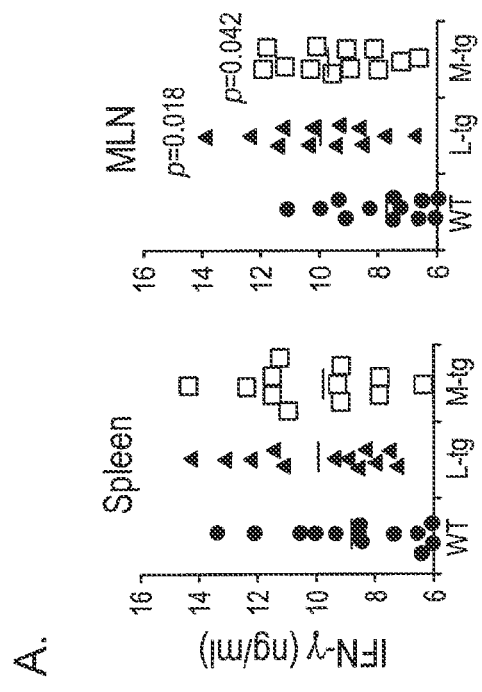
Figure 27:
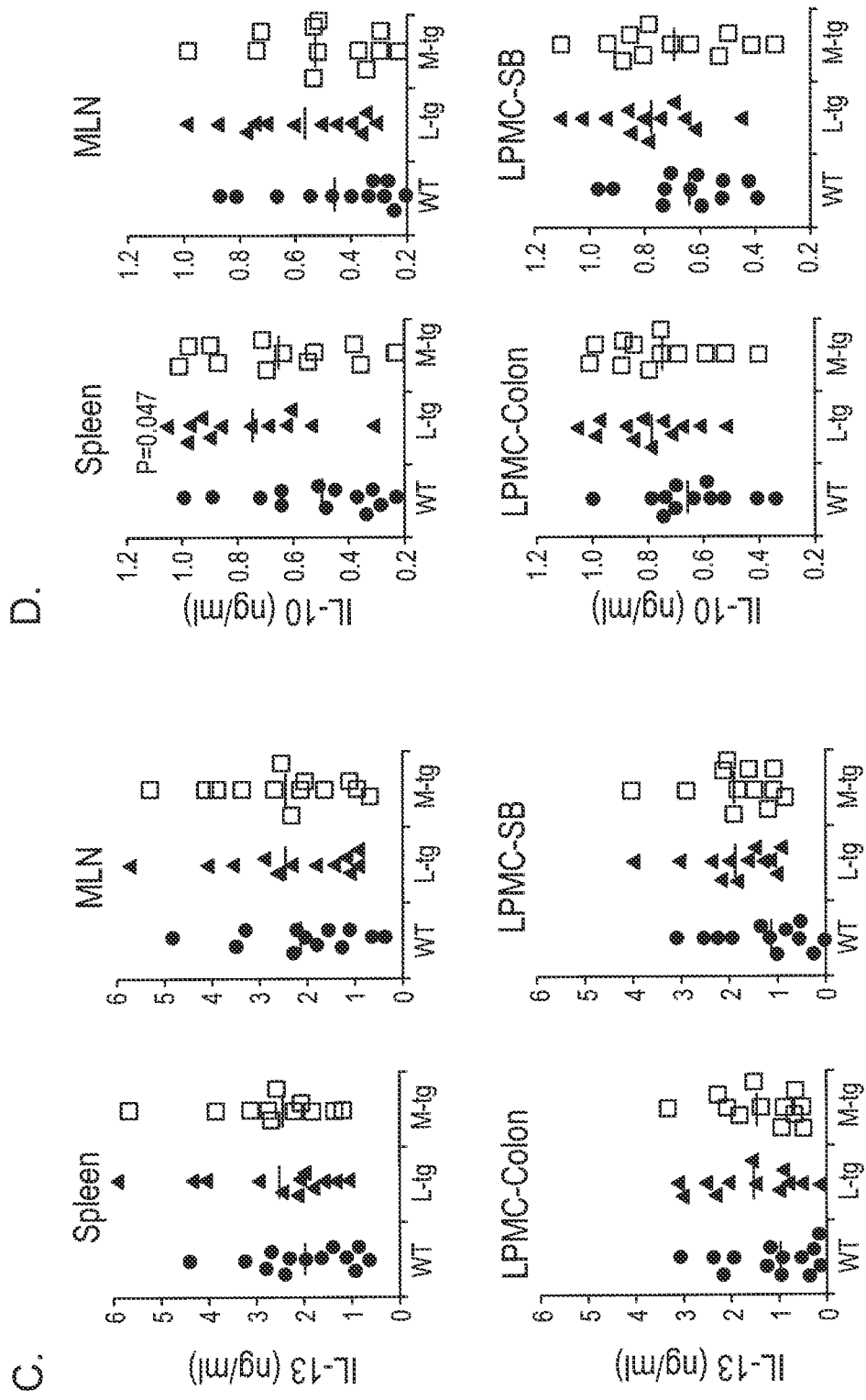

By 10 months of age, the frequency of CD4+, IFN-γ+, CD4+, and IL-17+ T-cells increased by approximately 3- and 2-fold respectively, in the MLN of L-Tg mice, as shown by FACS (FIG. 26B). In the M-Tg mice, the percentage of CD4+, IFN-γ+ cells increased by approximately 2-fold (FIG. 26B). The inventors did not observe any differences in the CD4+, IL-13+ T-cells in both of the TL1A Tg mice and only a negligible difference in the CD4+, IL-17+ T-cells in M-Tg mice (FIG. 27).

To confirm the FACS findings, the inventors isolated cells from the spleen, MLN and LPMC from the colon and small intestine and assessed their ability to produce cytokines following stimulation with anti-CD3 and anti-CD28. Similar to the intracellular stain, the inventors found significantly higher IFN-γ production in the MLN and small intestine LPMC of L-Tg mice (FIG. 27A). FMS-TL1A. Tg mice also exhibited significantly increased IFN-γ production in MLN and a trend toward a higher level in the LPMC from the small intestine. There was also a trend toward higher IL-17 and IL-13 production in the MLN and small intestine LPMC of both LCK-CD2-TL1A and FMS-TL1A Tg mice. Interestingly, the expression of the anti-inflammatory cytokine IL-10 appeared to be higher in both the TL1A Tg mice was statistically significant in the splenic cells of L-Tg as compared to WT mice. These data suggested that constitutive expression of TL1A in vivo resulted in enhanced IFN-γ and IL-10 production and potentially enhanced IL-17 and IL-13 production.

Example 15

Two Chronic Colitis Induction Models: Chronic Dextran Sodium Sulfate (DSS)-induction and Adoptive-transfix Models Further studies were performed by the inventors to determine the in vivo consequence of elevated TL1A expression under induced colitogenic settings. Two leading approaches are chronic dextran sodium sulfate (DSS)-induced model (performed using both L-Tg and M-Tg mice) and adoptive-transfer model (using L-Tg mice).

In all models, there was proximal migration of colonic inflammation, worsened patchy intestinal inflammation, and strictures in the intestine and colon with constitutive TL1A expression. This is remarkably similar to CD patients, wherein TATFSF15 haplotype B and elevated TL1A expression in primary monocytes exhibits worsened ileo-cecal inflammation with relative recto-sigmoid sparing and intestinal fibrostenosis.

These novel TL1A murine Tg models therefore resemble a complicated form of severe human CD. Results from both TL1A transgenic models coupled with findings in CD patients suggest that TNFSF15 is a severity gene and that the cytokine, TL1A, when over expressed, plays a central role generating one phenotypic form of complicated CD, For histopathological labeling and expression studies, statistical data are presented as the mean±standard deviation (SD). Comparison between two groups was performed by a two-tailed Fisher's Exact Test for categorical variables and Student's t-test for continuous variables. $p<0.05$ was considered significant.

Example 16

Transgenic Mice and Induction of Chronic Colitis

LCK-CD2-T11A-GFP (L-Tg) and M-Tg (M-Tg) mice were generated and genotyped as described. [57]

For the DSS-induced colitis model, experiment was performed as described except 2% (wt/vol) DSS (MP Biomedicals, Irvine, Calif.) drinking water was used due to lethality in TL1A-Tg mice when DSS concentration ≥2.5% was used.

In the adoptive-transfer model, colitis was induced by intraperitoneal injection of 500,000 CD4+CD45RBhi naïve T-cells isolated from either L-Tg, or WT mice to Rag1−/− mice. [59] All mice were maintained under specific pathogen-free conditions in the Animal Facility at Cedars-Sinai Medical Center CSMC). Littermate control mice were used. This study was carried out in strict accordance with the Guide for the Care and Use of Laboratory Animals of the National Institute of Health. Animal studies were approved by the CSMC Animal Care and Use Committee (protocol 2269).

Example 17

Comparison to Human Subjects, Including TL1A Overexpressing Subjects

Patients enrolled in this study were seen at the CSMC IBD-center and had been diagnosed with CD according to standard clinical, endoscopic, radiological, and histological findings. Written informed consent was obtained and approved by the CSMC institutional Review Board (IRB 3358 and 2673). Clinical course, laboratory values, and endoscopic findings, were collected and histology scored by two pathologists blinded to TL1A status (DQS and MV). The biopsy specimens from the first 7 available colonoscopy at CSMC after IBD diagnosis were used. More than 10 histologic sections per gut region from each patient were scored at 200× magnification. [73] Assessment of TL1A levels, genotyping and haplotype assignment had been performed. Patients defined as high TL1 A producers were Jewish subjects with homozygous risk haplotype-B whose immune-complex stimulated TL1A at 6 hours were >0.15 ng/mL/1× $10^6$ monocytes. Patients defined as low TL1A producers were Jewish subjects with homozygous protective haplotype-A whose immune-complex stimulated TL1A at 6 hours was <0.15 ng/mL/1×$10^6$ monocytes.

Example 18

Figure 28:
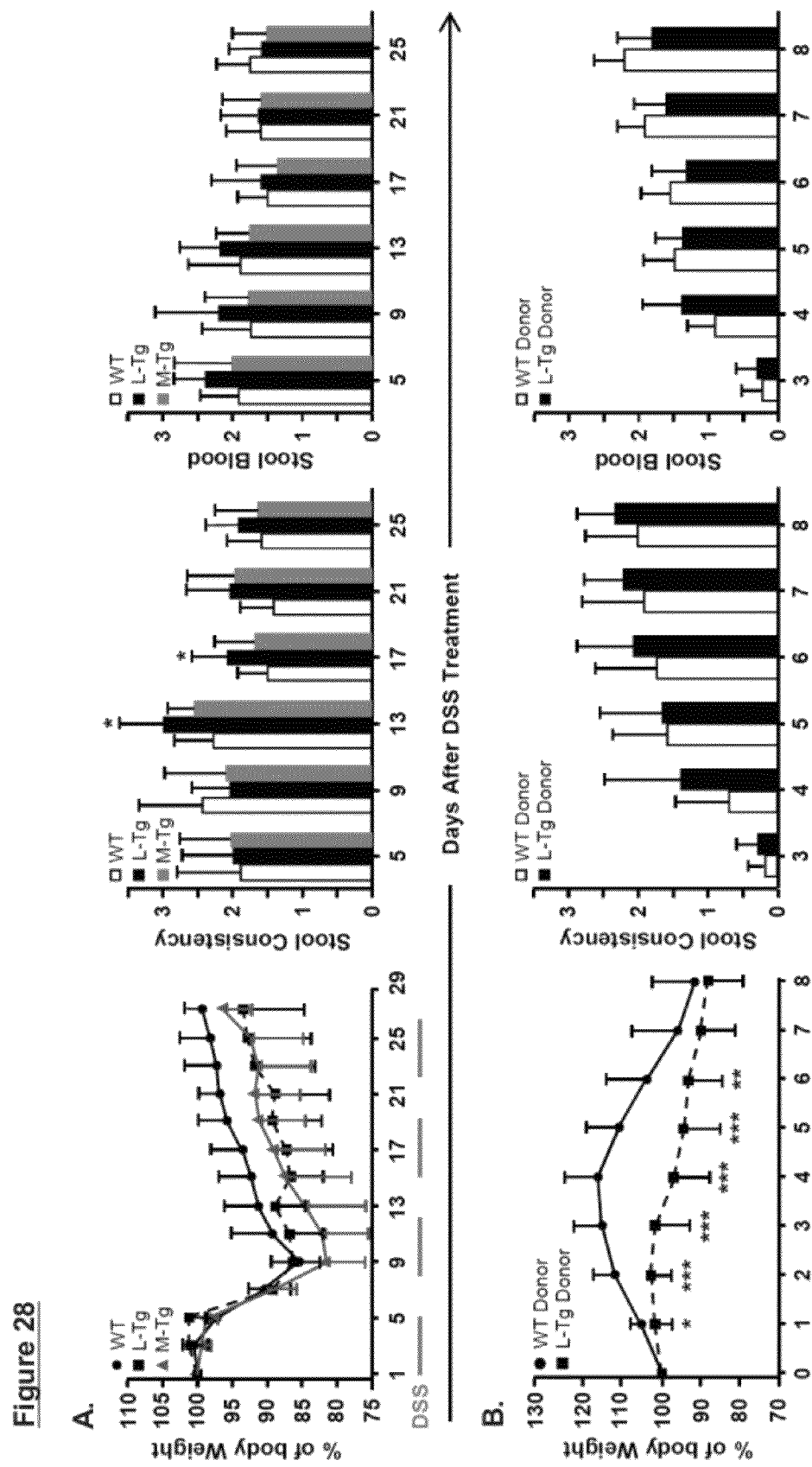
FIG. 28 depicts, in accordance with an embodiment herein, intestinal and colonic disease features in WT, L-Tg, and M-Tg mice, DAI composed of body weight change, stool consistency and blood are shown for (A) DSS-induced colitis (n=15 for WT, M-Tg; n=15 for L-Tg) and (B) adoptive T-cell transfer model (n=12). Data are expressed as mean±D. (C) Gross appearance of intestine and colon were measured using a standard scoring system. [59] (D) Myeloperoxidase activity was measured and data are expressed as arbitrary unit (U) per gram (g) of protein. (E) Total numbers of mononuclear cells were isolated from the distal 10 cm of intestine or colon. For (C)-(D), each symbol represents independent mice. Each symbol in (D) represents mean of triplicates. *$p<0.05$, $p<0.01$, *$p<0.001$.
Figure 28:
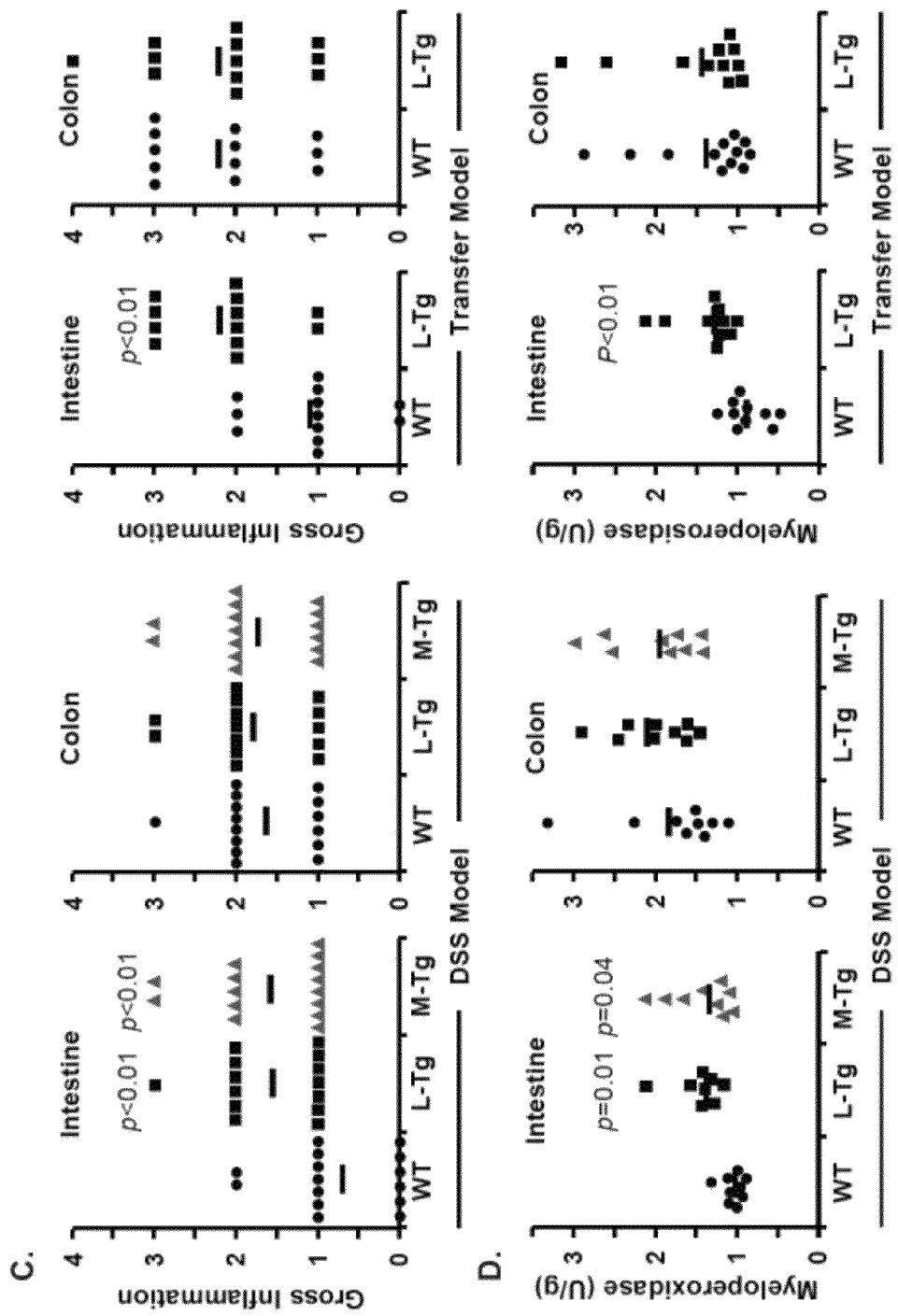
Figure 28:
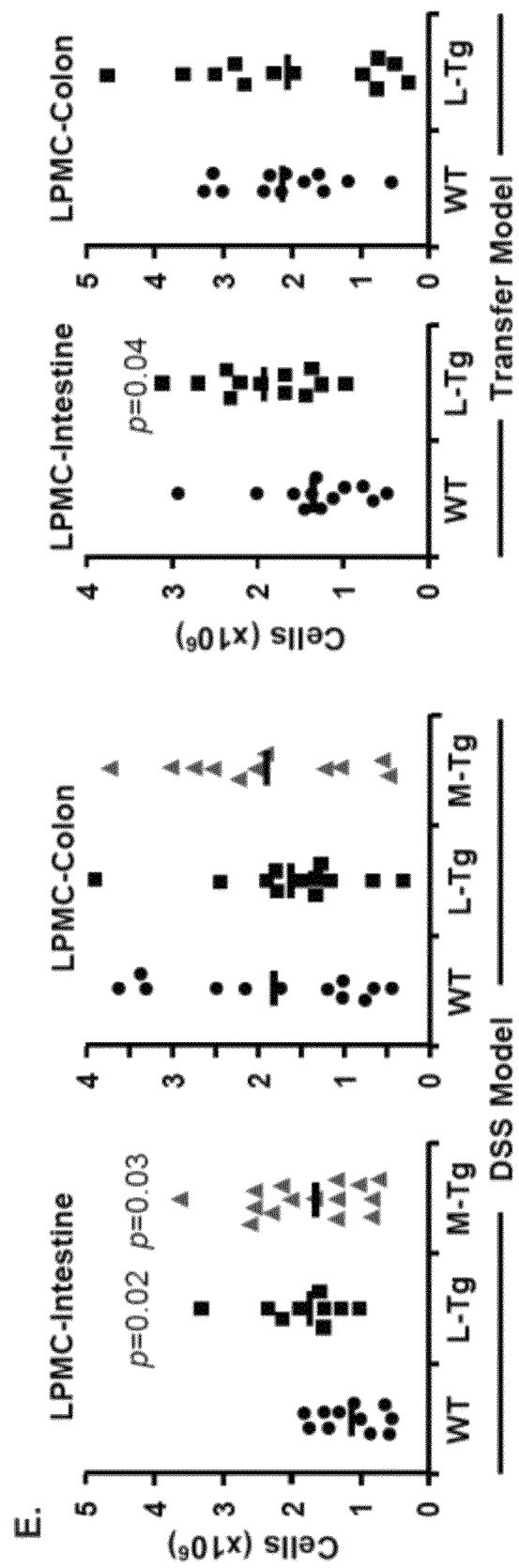

Constitutive TL1A Expression Led to Reduced Weight in Induced Chronic Colitis Models DSS-induced and adoptive T-cell transfer models were used to determine the in vivo consequences of TL1A overexpression, Adaptive immunity plays an important role in chronic colitis induced by multiple cycles of DSS [9, 74], a process which can be modeled by adoptively transferring naïve CD4+CD45RBhi T-cells into immune-deficient Rag1−/− mice. [59] In the DSS model, TL1A Tg lost more weight than WT littermates but the difference was not significant (FIG. 28A). No difference in the amount of stool blood and consistency was found between WT and Tg mice except on days 13 and 17 where LCK-CD2-TL1A-GFP (L-Tg) 8 mice had looser stool compared to WT and M-Tg (M-Tg) mice (FIG. 28A). In the adoptive-transfer model, Rag1−/− mice that received naïve L-Tg (but not WT) T-cells had significantly lower weight by week 1 which persisted up to week 6 after T-cell transfer (FIG. 28B). No differences in the amount of stool blood or consistency were found (FIG. 28B).

Example 19

Increased Intestinal Inflammation in the TL1A-Tg Mice

Inspection of the gut revealed worsened gross inflammation in the intestine of TL1A-Tg compared to WT mice in both chronic colitis models (FIG. 28C). Another measure of gut inflammation was to determine myeloperoxidase activity.11 Compared to WT mice, elevated myeloperoxidase activity in the ileum of TL1A-Tg mice in both models of chronic colitis were found (FIG. 28D), Additionally, greater numbers of LPMC were isolated from the intestine of TL1A-Tg than from WT mice (FIG. 28E).

Figure 29:
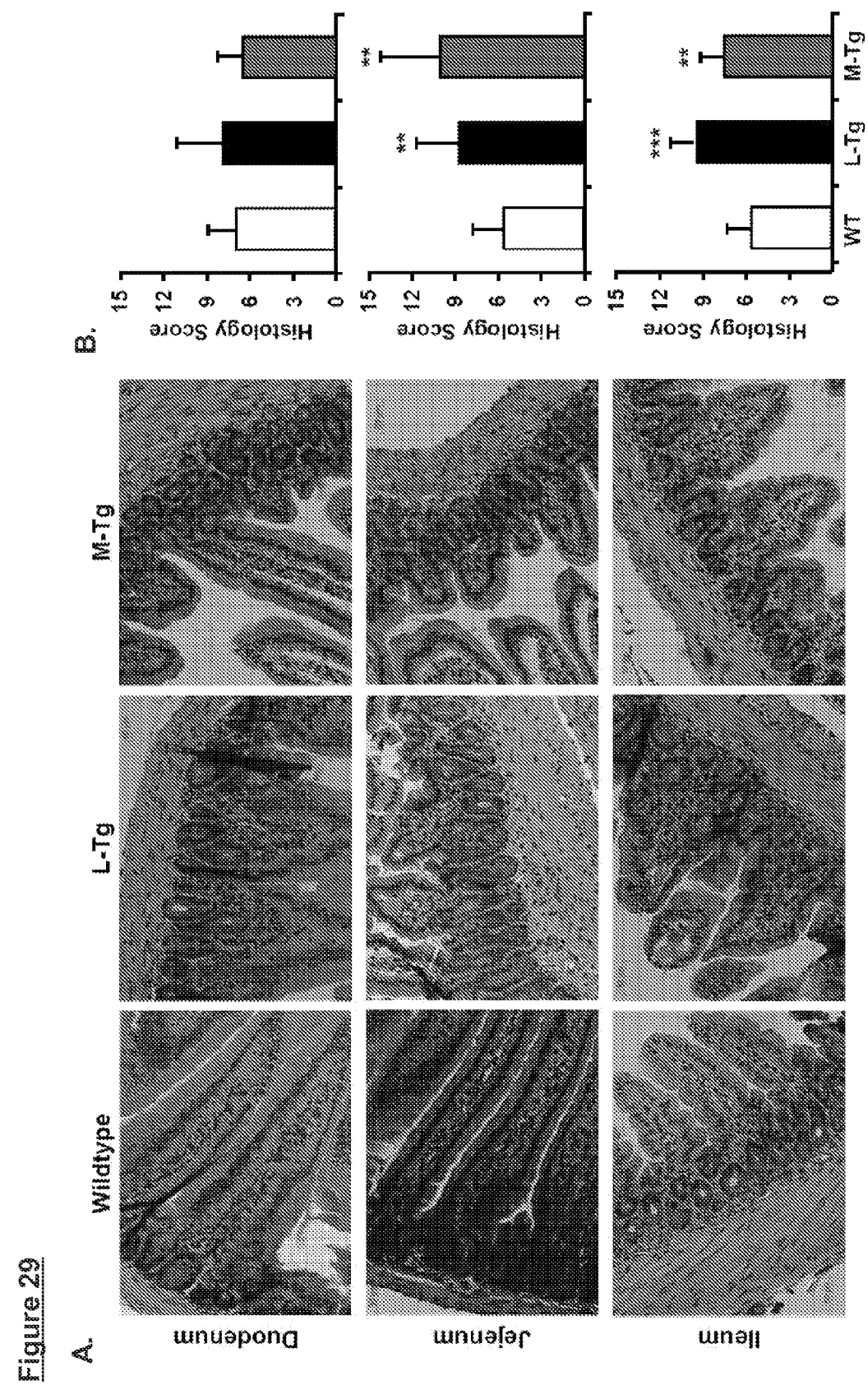
FIG. 29 depicts, in accordance with an embodiment herein, L-Tg and M-Tg mice have patchy intestinal inflammation. Representative H&E stained DSS (A) and adoptive transfer (B) intestinal sections are shown. Quantative 20 histology scores for DSS (C) and adoptive transfer (D) were determined. Data are expressed as mean±SD. Fields at 200× magnification were scored. $p<0.01$, *$p<0.001$.
Figure 29:
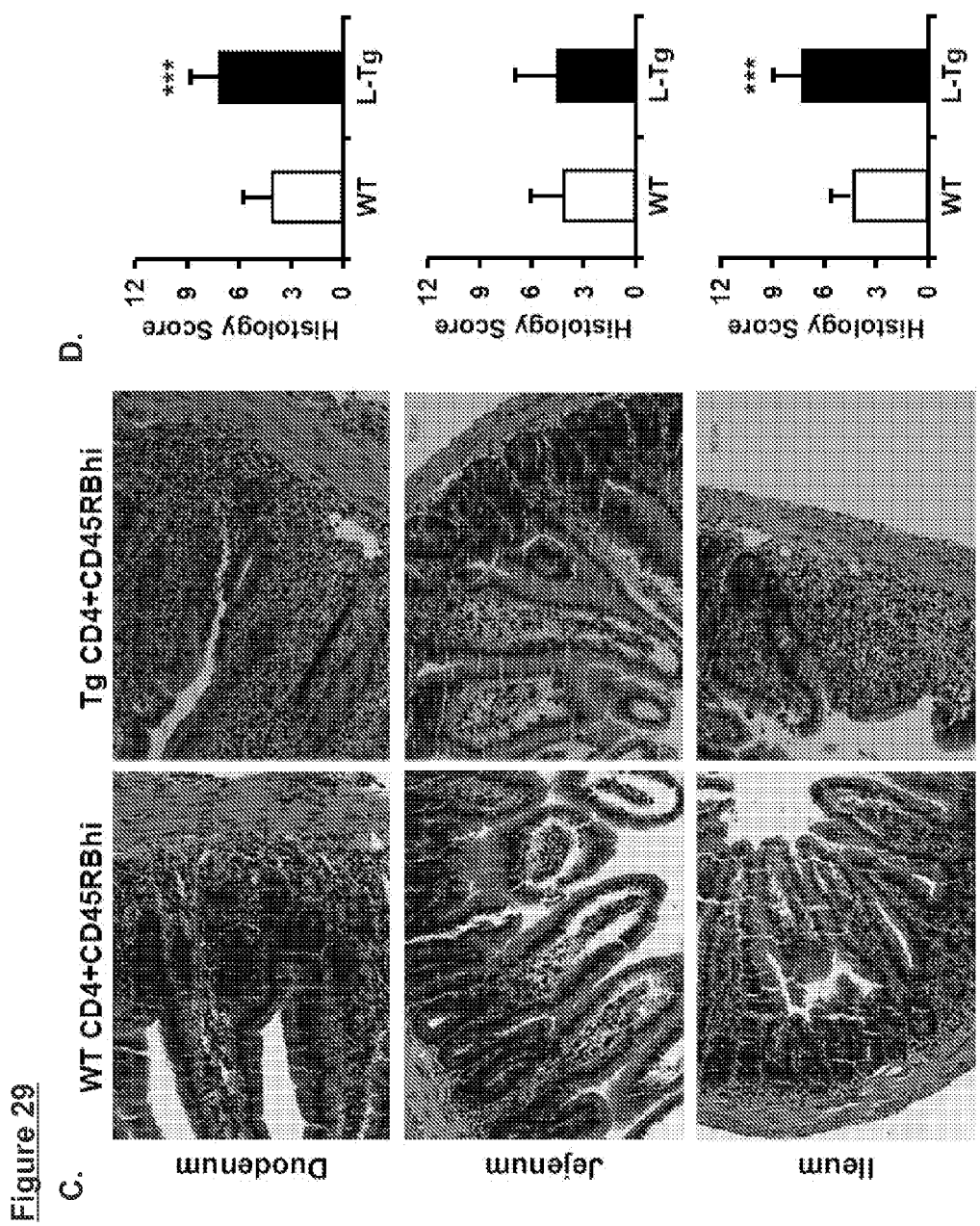

Histologic examination of the intestine revealed blunting of the villi, crypt damage, worsened inflammatory changes, and increased mononuclear cell infiltration of the lamina propria (LP), particularly in the ileum from TL1A-Tg compared to WT mice in both the DSS (FIG. 29A) and adoptive-transfer models (FIG. 29B). Depending on the murine colitis model used, different intestinal areas with increased inflammatory changes were observed. For example, histological changes were reflected by a significant increase in the inflammatory score of TL1A-Tg mice in the jejunum and ileum of the DSS model and in the duodenum and ileum of the T-cell transfer model (FIGS. 29A, 29B). Taken together, constitutive TL1A expression in either T-cells or myeloid lineages resulted in patchy intestinal inflammation.

Example 20

Proximal Migration of Colonic Inflammation in the TL1A-Tg Mice

No differences were found in the overall gross inflammatory score (FIG. 28C), myeloperoxidase activity (FIG. 28D) or lamina propria mononuclear cell (LPMC) recovery (FIG. 28E) in the colon between WT, M-Tg, and L-Tg mice in both chronic colitis models.

However, in the DSS-induced colitis model, enhanced inflammation was observed in the cecum of M-Tg and L-Tg mice compared to WT cecum (FIG. 30A). No differences in inflammation were found in other areas of colon between WT, M-Tg and L-Tg mice (FIG. 30B). These histological changes were reflected by a significant increase in the inflammatory score in the cecum, but not other colonic regions (FIG. 30B).

In the adoptive T-cell transfer model, proximal migration of colonic inflammation was observed in Rag1−/− mice transferred with T-cells from L-Tg mice, when compared to WT T-cells (FIGS. 30C, 30D). Compared to WT mice, there was exacerbation of ileo-cecal inflammation but relative sparing of inflammation in the recto-sigmoid colon of TL1A mice (FIG. 30C, D). Closer inspection of colonic specimens revealed increased hyperemia, wall thickening, edema, and adhesions in the cecum with relative sparing in the rectum in the Rag1−/− mice transferred with L-Tg T-cells compared to WT T-cells (FIG. 30E). These data showed elevated TL1A expression led to proximal migration of colonic inflammation with relative rectal sparing in the adoptive T-cell transfer model.

Example 21

Constitutive TL1A Expression Leads to Gut Fibrostenosis

Mice with constitutive TL1A expression developed both intestinal and colonic gross structuring disease in both chronic colitis models. In the DSS model, gross strictures were present only in the M-Tg and L-Tg mice: intestine up to 3 cm in length (WT, 0/15 mice; LTg, 3/14 mice; M-Tg, 3/15 mice), colon <1 cm in length (WT, 0/15 mice; LTg, 3/14 mice; M-Tg, 3/15 mice), In the adoptive-transfer model, gross strictures were only present in Rag1−/− mice transferred with TL1A T-cells: intestine up to 3 cm in length (WT, 0/12 mice; L-Tg, 4/12 mice), colon (WT, 0/12 mice; L-Tg, 3/12 mice). Art example of fibrostenotic disease in the colon and intestine is shown in FIG. 31A. At a low frequency, hydronephrosis with ureteral stricture was observed in the DSS model from the TL1A Tg mice (WT, 0/15; L-Tg, 1/14; M-Tg, 1/15) and in the adoptive T-cell transfer model (WT, 0/12; 1/14). An example of hydronephrosis with ureteral stricture is shown in FIG. 31B.

Figure 31:
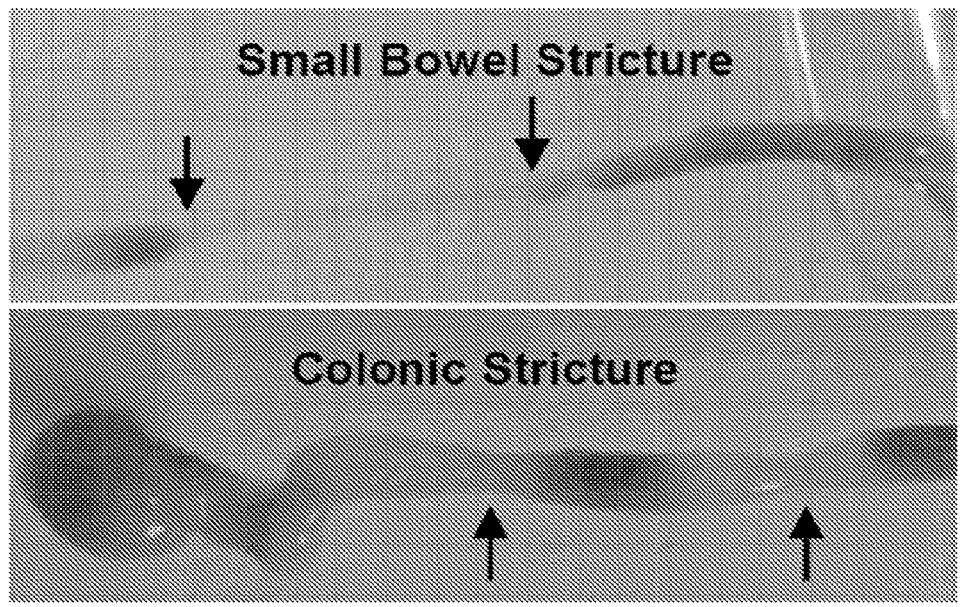
FIG. 31 depicts, in accordance with an embodiment herein, TL1A-Tg mice have fibrostenotic disease. (A) Representative pictures of intestinal and colonic stricture are shown. (B) Representative picture of hydronephrosis due to ureteral stricture are shown. Masson-Trichrome staining of collagen deposition in non-strictured tissue sections of mouse mid-colon and distal 3 cm of ilea are shown for the DSS model in (C). Collagen was stained blue. Thickness of collagen deposition was quantitated and represented as mean±SD in (C). Vimentin stain of fibroblasts in nonstrictural tissue sections were performed for the DSS model in (D). Fibroblasts were stained brown. Vimentin-positive cells were quantitated and represented as mean±SD in (D). Fields at 200× magnification were scored. *$p<0.05$, $p<0.01$, *$p<0.001$.
Figure 31:
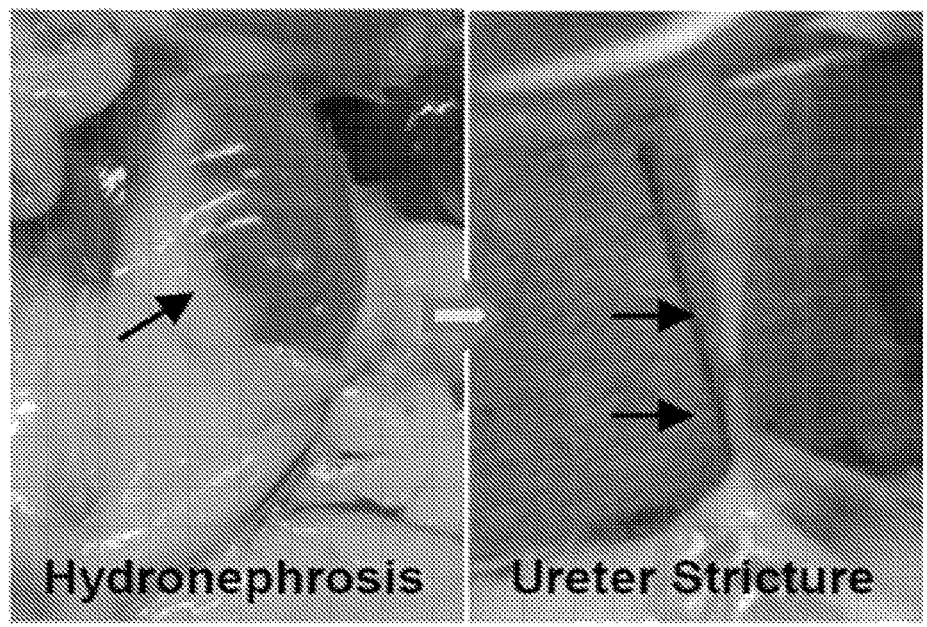
Figure 31:
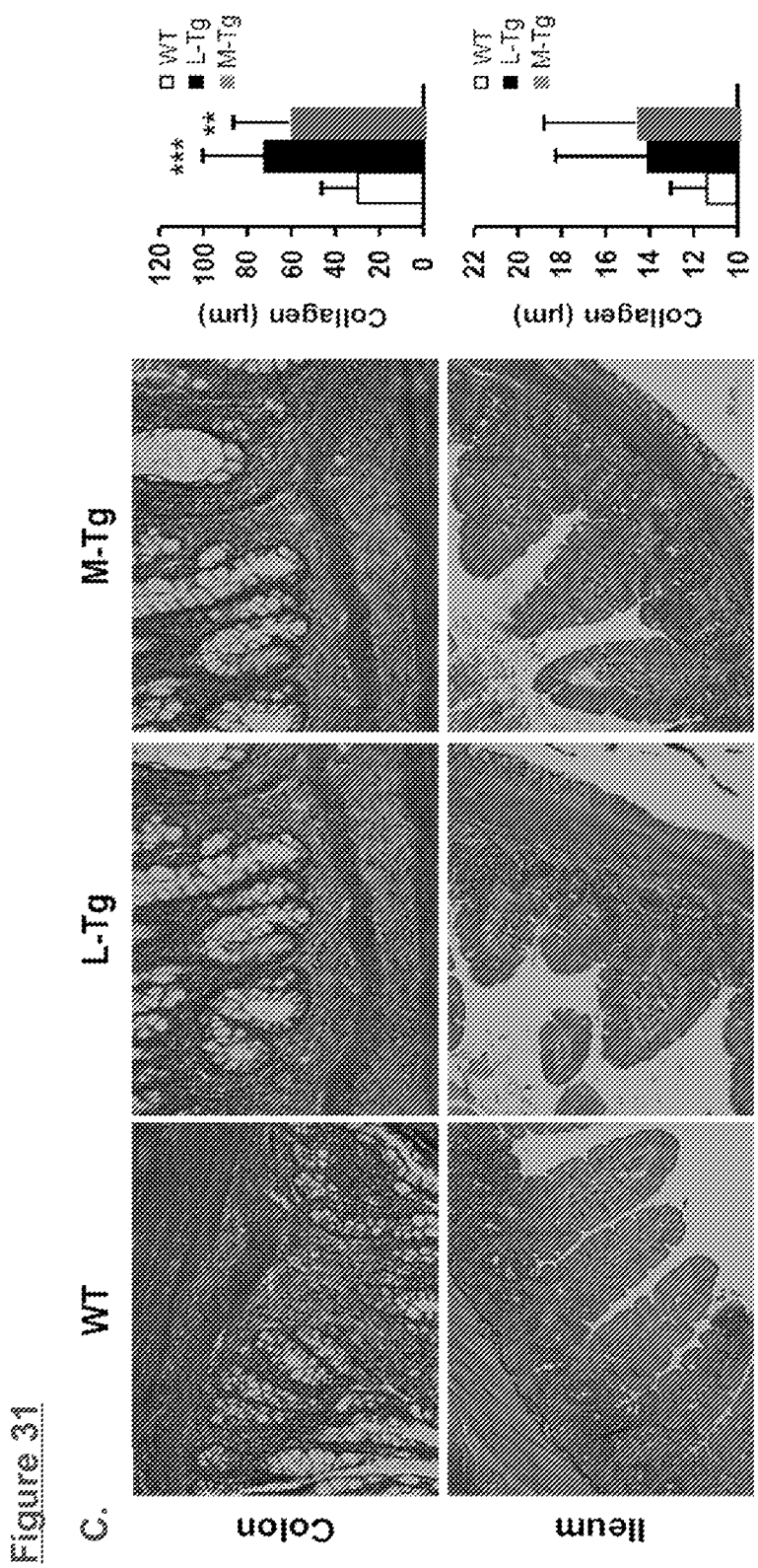
Figure 32:
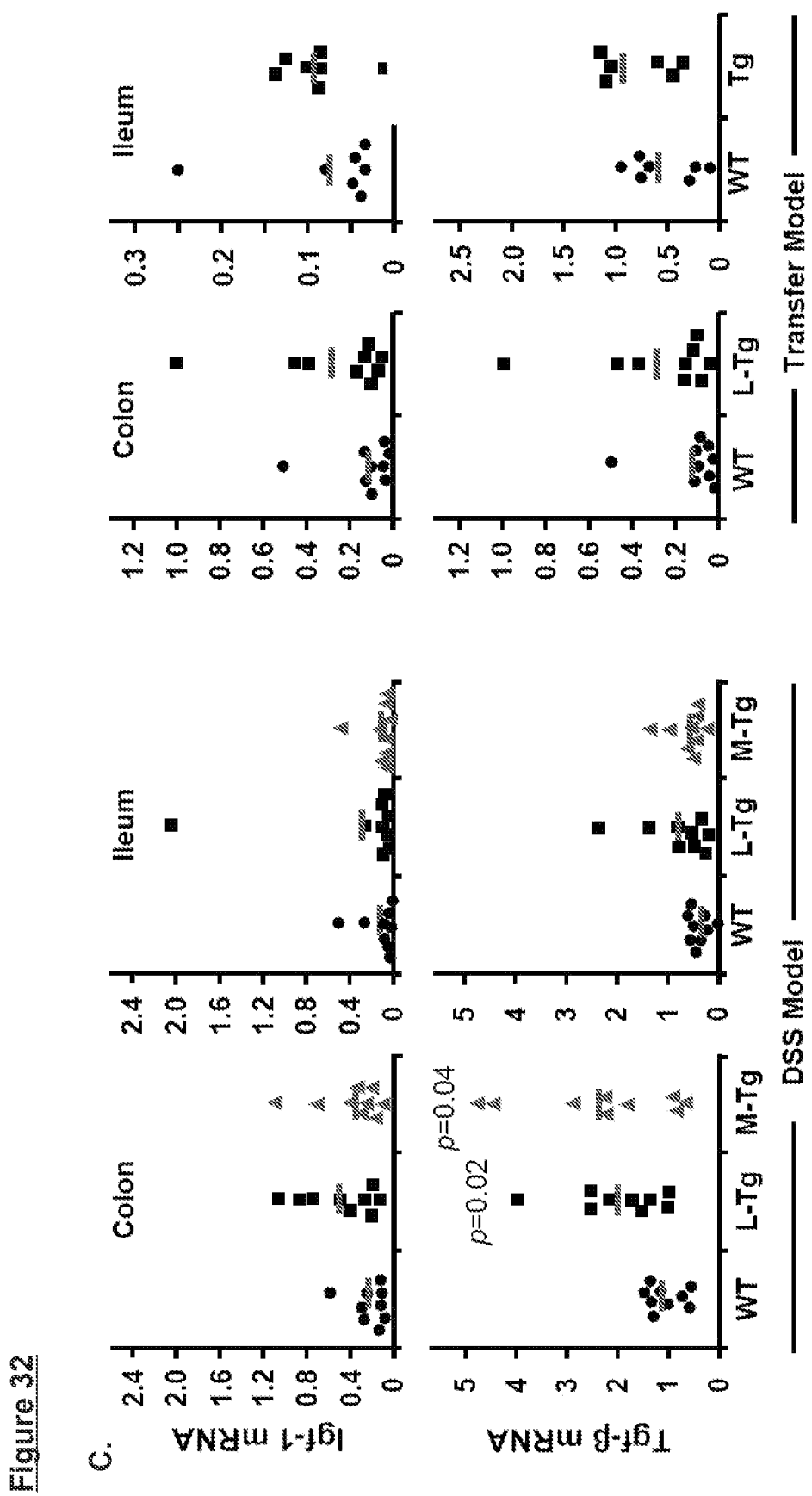
FIG. 32 depicts, in accordance with an embodiment herein, adoptive transfer of L-Tg mice can lead to fibrostenotic disease. (A) Masson-Trichrome staining of collagen deposition in non-strictured tissue sections of mouse 21 mid-colon and distal 3 cm of ilea are shown for the adoptive-transfer model. Thickness of collagen deposition was quantitated and represented as mean±SD. (B) Vimentin stain of fibroblasts in non-strictured tissue sections were performed for the adoptive transfer model. Fibroblasts were stained brown. Vimentin-positive cells were quantitated and represented as mean+SD. Fields at 200× magnification were scored for (A) and (B) (C) IGF-1 and TGF-β mRNA expression were measured from mid-colon and ileum. Each symbol represents expression measured from independent mice performed in duplicates. *$p<0.05$, **$p<0.01$

To determine whether there was increased collagen deposition, Masson-Trichrome stain was performed on colonic and intestinal regions without gross stricture. Increased Masson-Trichrome stain in the colon, but not intestine, of TL1A Tg mice undergoing chronic DSS treatment was observed (FIG. 31C). The increased Masson-Trichrome stain was correlated with increased thickness of colonic collagen deposition in both L-Tg and M-Tg mice when compared to WT mice (FIG. 31C). Collagen is secreted by fibroblasts and can be identified by the marker vimentin. [63] Compared with WT controls, an increased number of vimentin-positive cells were observed in both the non-strictured colon and ilea of DSS-treated TL1A transgenic mice (FIGS. 31D). Similar to the DSS model, 11 increased collagen deposition was found in the non-strictured colon in Rag1−/− mice transferred with L-Tg T-cells (FIG. 32A). Increased numbers of vimentin-positive cells were observed in both the non-strictured ileum and colon of Rag1−/− mice transferred with L-Tg T-cells than with WT T-cells (FIG. 32B).

As increased colonic mRNA expression of pro-fibrogenic factors TGF-β1 and IGF-1 in CD patients had been reported [64, 65] the expression of these genes was assessed. Compared to WT mice, increased expression of colonic TGF-β1 in the both types of TL1A Tg mice undergoing chronic DSS treatment was found in the non-fibrotic colonic sections (FIG. 32C). The expression of TGF-β1 in the intestine was not different between WT and TL1A Tg mice (FIG. 32C). No difference in the expression of IGF-1 was detected in both chronic colitis models (FIG. 32C). Together, these results demonstrated that constitutive TL1A expression in T-cells and myeloid cells lead to severe fibrostenotic disease in the murine gut, which may in part be due to elevated expression of the profibrogenic factor TGF-β1.

Example 22

Figure 33:
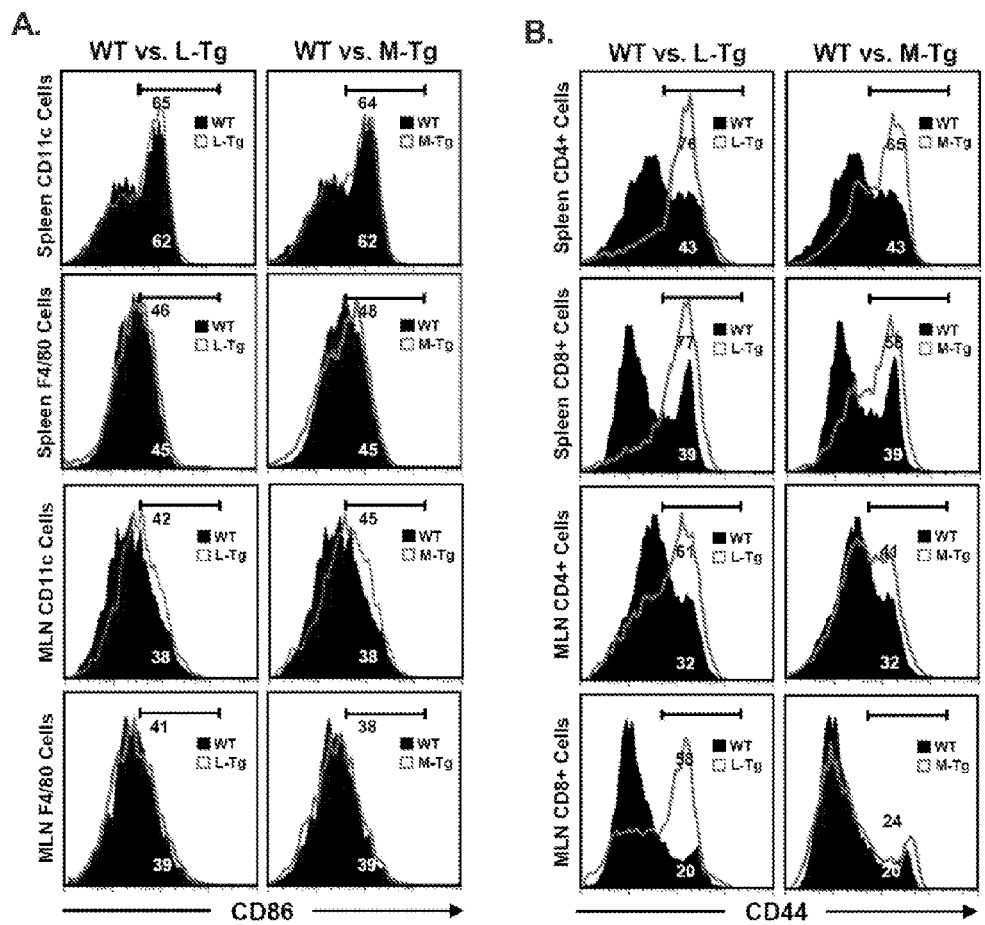
FIG. 33 depicts, in accordance with an embodiment herein, sustained TL1A expression leads to increased percentage of activated T-cells in DSS-induced chronic colitis. Flow cytometry plot of splenocytes and MLN cells showing expression of activation markers CD86 in (A) and CD44 in (B), CD4+, CD8+, CD11c+, or F4/80+ cells were gated as indicated. Data shown are representative of at least 5 independent experiments.

Accelerated T-cell Activation and Enhanced IL-17 Production in the Chronic DSS Colitis Model To assess the effect of TL1A expression on immune-cell composition, we performed FACS analysis. Flow cytometry did not reveal differences in the frequencies of CD3+, CD4+, CD8+, CD11c+ or F4/80+ cells in the spleen and MLN between L-Tg, M-Tg or WT littermate mice. To determine the effect of constitutive TL1A expression on the activation state of antigen presenting cells, expression of the activation marker CD86 was compared. Flow cytometry did not reveal differences in the CD86 expression between dendritic cells (CD11c+) and macrophages (F4/80+) between TL1A Tg and WT mice (FIG. 33A). There was a modest, but not significant increase in the frequencies of T-cells expressing the gut-homing markers chemokine receptor-9 (WT, avg 2.9%; L-Tg, avg 5.2%; M-Tg, avg 4.1%) and chemokine receptor-10 avg 5%; L-Tg, avg 8.9%; M-Tg, avg 7.6%).

Figure 34:
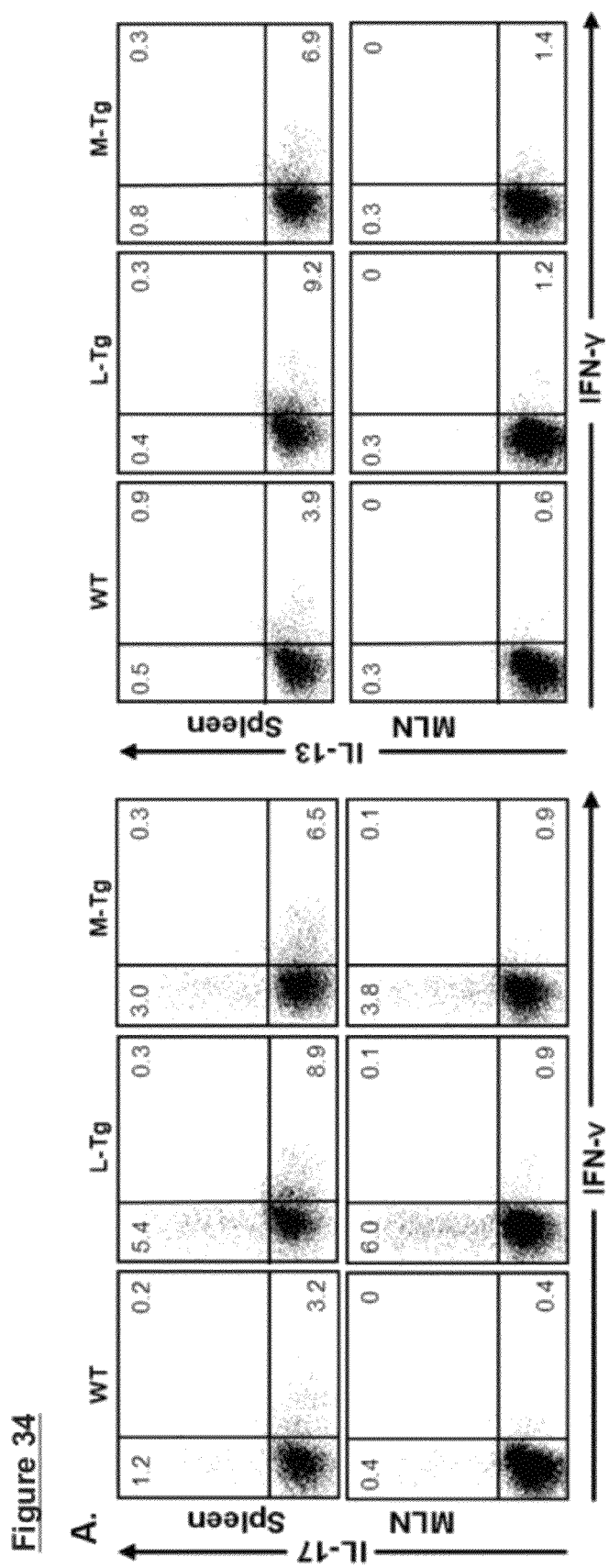
FIG. 34 depicts, in accordance with an embodiment herein, Sustained TL1A expression leads to increased IL-17 expression in DSS induced chronic colitis. (A) Flow cytometry plots of gated CD4+ cells from spleen and MLN and stained for intracellular IFN-γ, IL-17, and IL13 expression are shown. Data shown are representative of ≥5 mice per group. (B) IFN-γ, IL-17, IL13, TNFα and IL-6 secretion after stimulation with anti-CD3 and anti-CD28 were assessed by ELISA. Each data point represents cytokine expression for splenocytes, MLN cells, or LPMC from an individual mouse. p-values are indicated where significant.
Figure 34:
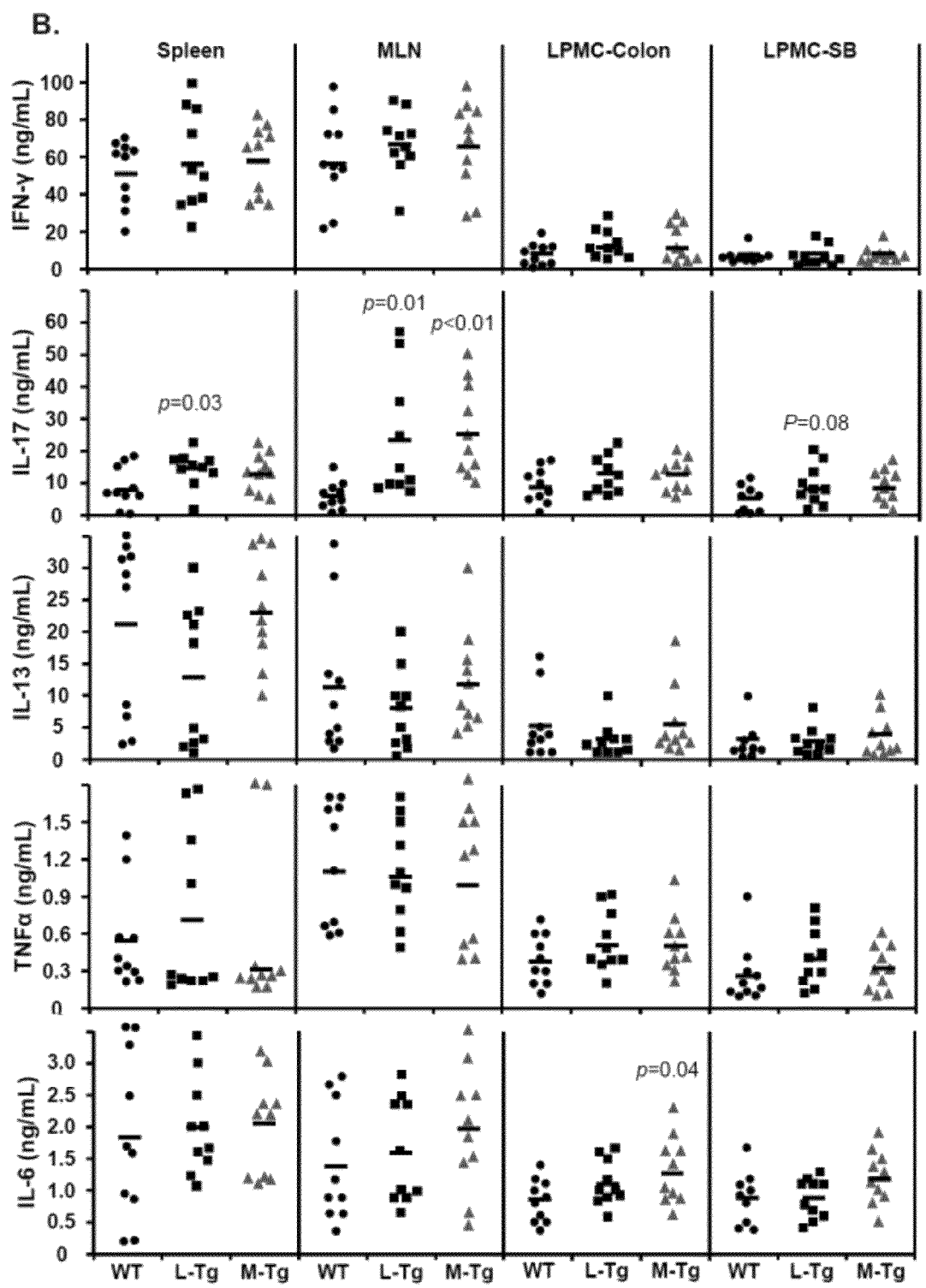

To assess whether elevated TL1A expression can enhance the co-stimulation of T-cells in the DSS model, we compared the expression of CD44 on CD4+ and CD8+ cells between TL1A. Tg and WT littermate controls. CD4+ CD45RB$_{low}$CD25+ T$_{reg}$ cells were gated out to examine the expression of activation markers on conventional T-cells, Compared to WT mice, a higher percentage of TL1A Tg CD4+ and CD8+ cells expressed the activation marker CD44, particularly L-Tg mice (FIG. 33B). To assess the molecular consequences of increased T-cell activation in the TL1A Tg mice, the expression of IFN-γ, interleukin (IL)-13, and IL-17 were measured. FIG. 34A shows that the frequency of CD4+ IFN-γ+ and CD4+IL-17+ T-cells were increased in TL1A Tg mice compared to WT mice, and reached significance in the frequency of CD4+IL-17+ in the MLN (WT vs. L-Tg, p=0.03; WT vs. M-Tg, p=0,04). Similar to the intracellular stain, higher IL-17 production in the MLN for both TL1A Tg mice and in the spleen for L-Tg mice was found (FIG. 34B). There was a trend toward higher IL-17 production in the LPMC from the intestine of L-Tg mice (p=0.08) (FIG. 34B). No differences in the production of IFN-γ, IL13, TNFα or IL-6 were observed (FIG. 34B).

Example 23

Figure 35:
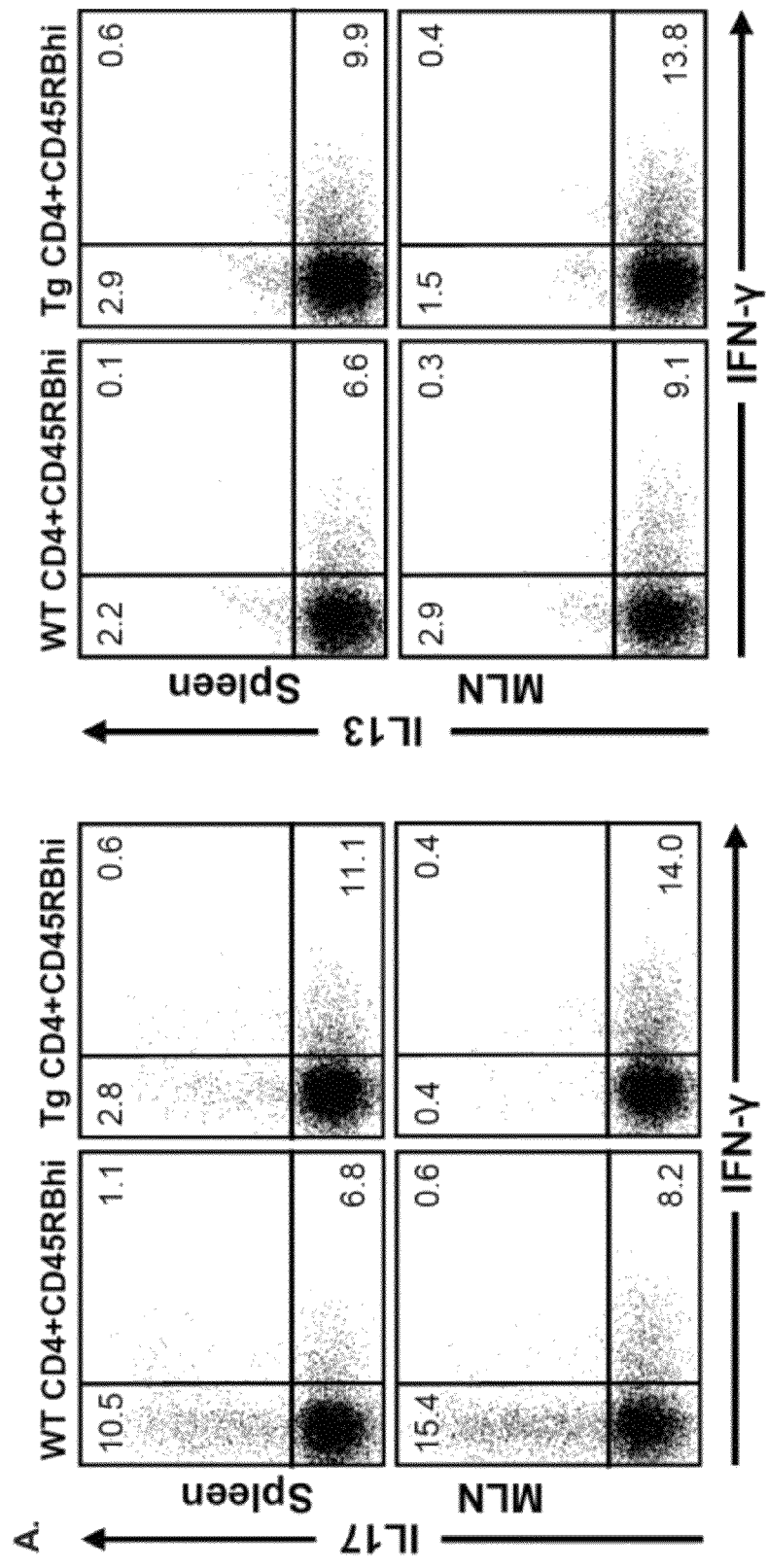
FIG. 35 depicts, in accordance with an embodiment herein, Sustained TL1A expression leads to increased IFN-γ and reduced IL-17 expression in the adoptive-transfer model. (A) Flow cytometry plots of gated CD4+ cells from spleen and MLN and stained for intracellular IFN-γ, IL-17, and IL13 expression are shown. Data shown are representative of ≥5 mice per group. (B) IFN-γ, IL17, IL13, TNFα and IL-6 secretion after stimulation with anti-CD3 and anti-CD28 were assessed by ELISA. Each data point represents cytokine expression for splenocytes, MLN cells, or LPMC of an individual mouse. p-values are indicated where significant.
Figure 35:
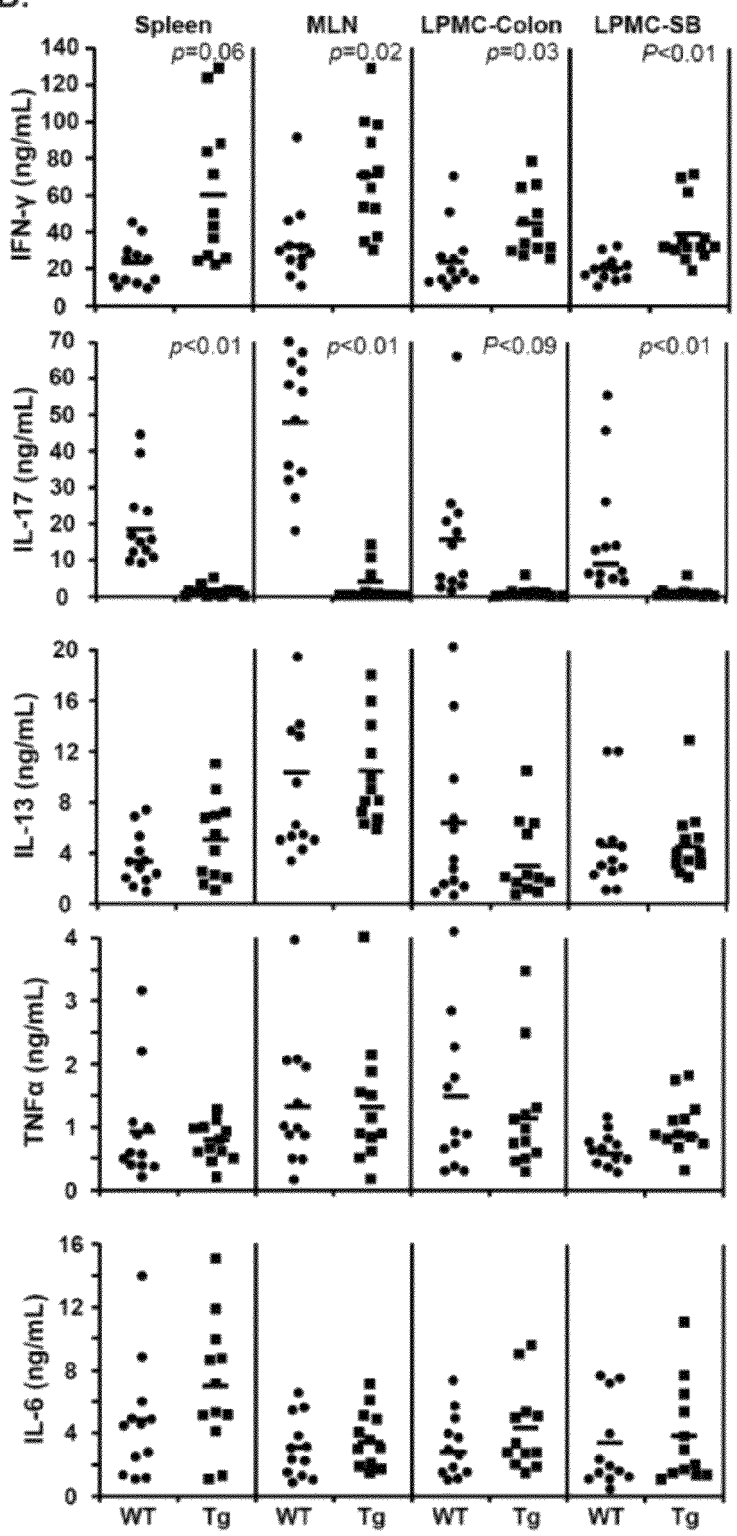

Constitutive TL1A Expression Led to Enhanced Th-1 but Reduced Th-17 Immune Responses in the Adoptive T-cell Transfer Model In the adoptive T-cell transfer model, no differences in the frequencies of CD3+, CD4+, chemokine receptor-10, activation markers (CD44 and CD86), CD11c+ or F4/80+ cells in the spleen and MLN between Rag1−/− mice transferred with WT or TL1A Tg T-cells were observed. There was a modest increase in the frequencies of CD4+ cells expressing chemokine receptor-9 in the spleen (WT, avg 3.7%; L-Tg, avg 8.9%)

and MLN (WT, avg 2.8%; L-Tg, avg 5.0%). Intracellular cytokine stain showed that the frequency of CD4+IFN-γ+ was significantly elevated in the spleen and MLN of Rag1−/− mice transferred with T-cells expressing TL1A compared to WT T-cells (FIG. 8A). There were very low numbers of CD4+IL-17+ T-cells in Rag1−/− mice transferred with TL1A Tg T-cells (FIG. 35A). No differences in the frequency of CD4+IL13+ cells were found (FIG. 35A). Consistent with the intracellular stain, higher IFN-γ production was found in the spleen, MLN, and LPMC in Rag1−/− mice transferred with TL1A Tg T-cells compared to WT T-cells (FIG. 35B). Significantly reduced IL-17 production was observed in all the tissues tested (FIG. 35B). No differences in the production of IL-13, TNFα, and IL-6 were observed. These data indicated that constitutive expression of TL1A in naïve CD4+ CD45RBhi T-cells may affect the proliferation, differentiation or maintenance of Th-1 and -17 cells in the peripheral immune-compartments and inflamed tissues.

Example 24

Figure 36:
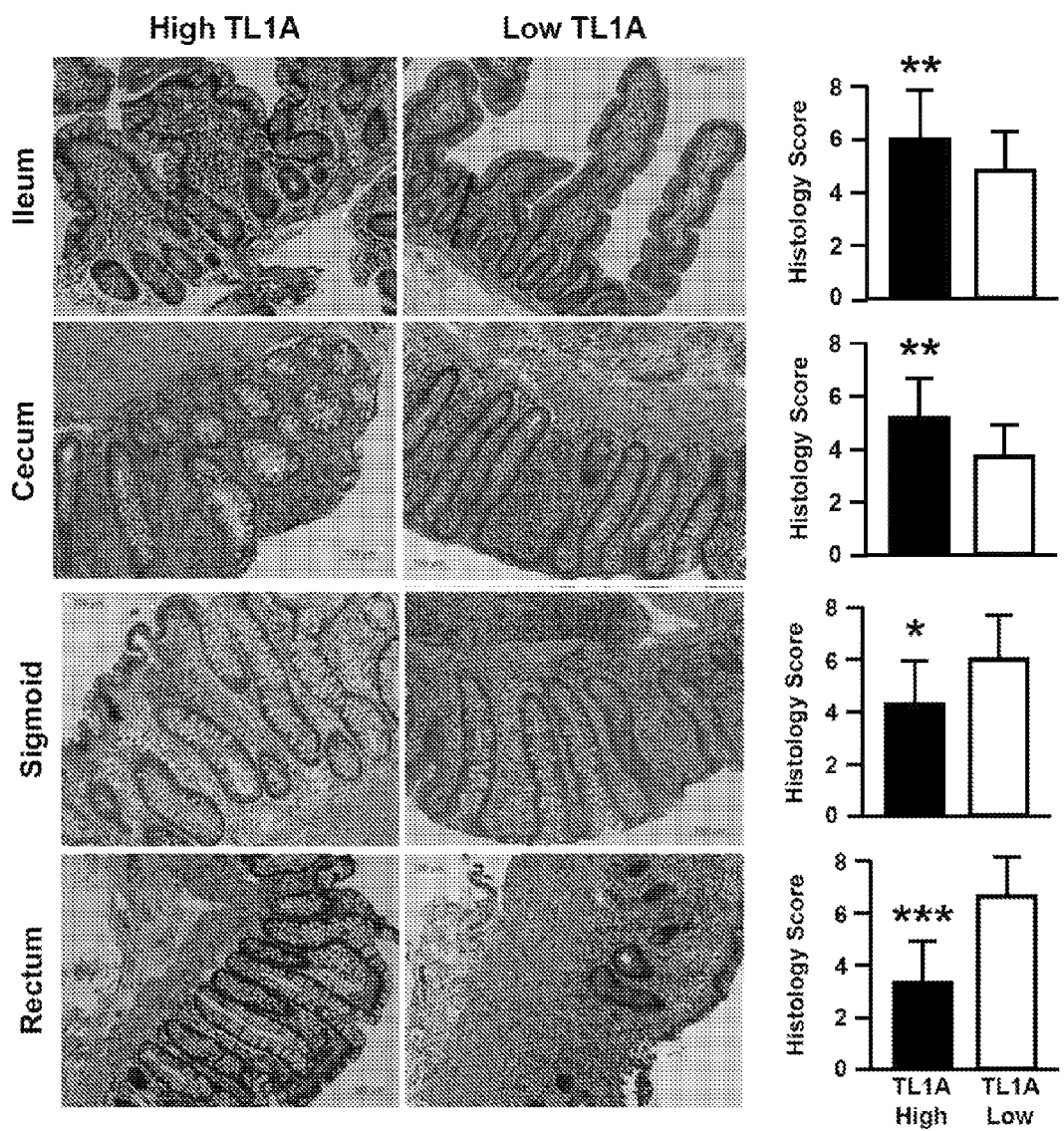
FIG. 36 depicts, in accordance with an embodiment herein, CD patients with elevated TL1A expression have increased ileo-cecal inflammation but reduced recto-sigmoid inflammation. Representative H&E stained intestinal and colonic sections are shown and corresponding histology scores were determined. Data are expressed as mean±SD. Sections at 200× magnification were scored by 2 pathologists blinded to the TL1A haplotype or its expression level. *$p<0.05$, *$p<0.01$, ***$p<0.001$.
Figure 37:
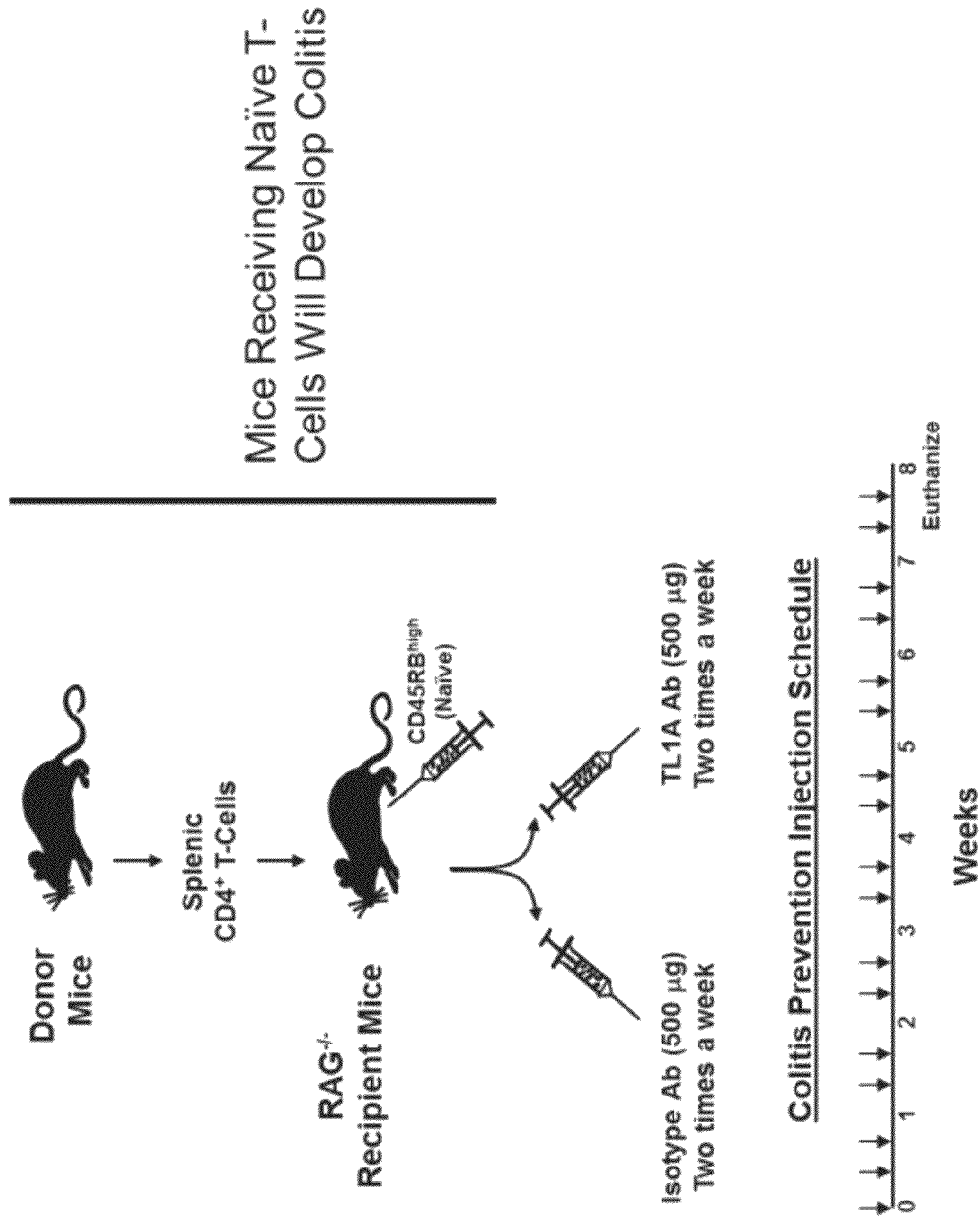
FIG. 37 depicts, in accordance with an embodiment herein, (A) general design of a colitis prevention in vivo experiment, wherein Rag1−/− deficient mice are injected with naïve T-cells to induce colitis and receive 2 injections of antibody (either TL1A 12F6A or isotype control) per week for 8 weeks; (B) TL1A antibody reduces weight loss in experimental colitis; and (C) TL1A 12F6A antibody reduces disease activity index.
Figure 37:
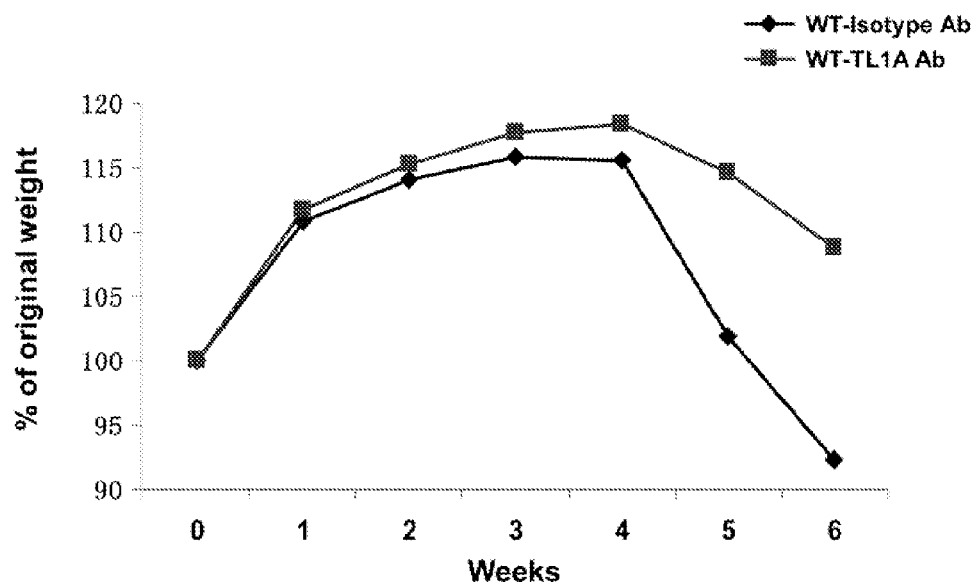
Figure 37:
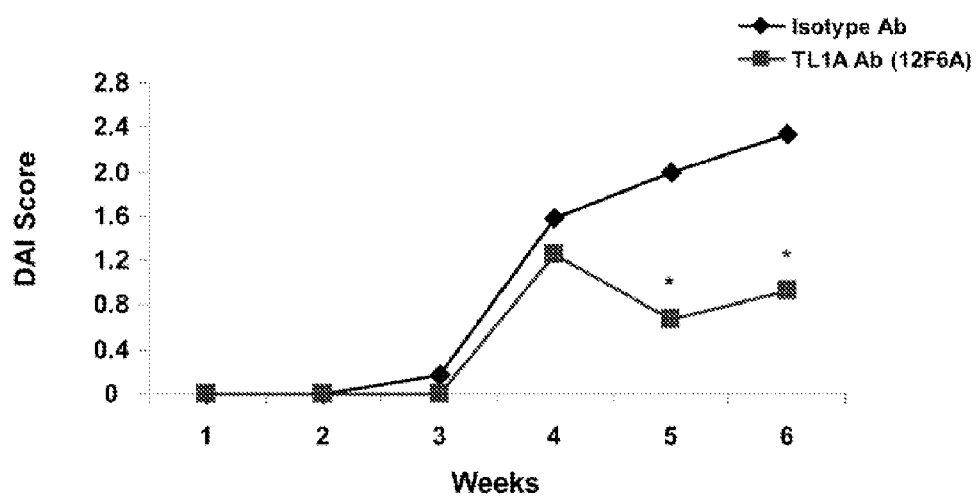

Human Study: Proximal Migration of Colonic Inflammation with Relative Rectal Sparing and Intestinal Fibrostenosis in High TL1A Expressing CD Patients Given the findings in mice, we examined whether humans with elevated TL1A expression had similar proximal migration of colonic inflammation with relative rectal sparing. A blinded retrospective analysis of CD patients with known TL1A expression profiles was performed. [24] In our previous study, TL1A level of 0.15 ng/mL/1×106 monocytes at 6 hours post immune complex (IC) stimulation distinguished over 90% of Jewish CD patients with risk TL1A haplotype-B and protective haplotype-A. [24] Therefore, high TL1A producers were defined as subjects with homozygous risk haplotype-B whose immune-complex stimulated TL1A at 6 hours was ≥0.15 ng/ML/1×106 monocytes and low TL1A producers had homozygous protective haplotrype-A whose immunecomplex stimulated TL1A at 6 hours was ≤0.15 ng/ML/1×10$^6$ monocytes. The patients' demographics, clinical features, and medications within 2 months of colonoscopy are provided in table 1. Significant increase in intestinal strictures and Harvey-Bradshaw Index were found in the high-TL1A compared to the low-TL1A group (Table 1). To assess whether TL1A expression level is associated with a specific mucosal pattern of inflammation, H&E stained histologic sections from ileum, cecum, sigmoid, and rectum were examined. Compared to the low-TL1A group, the high-TL1A group had more severe ileo-cecal inflammation with relative recto-sigmoid sparing of inflammation (FIG. 36). Together, these data suggest that CD patients who express elevated TL1A levels develop worsened inflammation in the ileo-colonic region and 15 proximal migration of colonic inflammation with relative sparing of inflammation in the sigmoid and rectum.

TABLE 1

Summary of clinical and laboratory data

|  | High TL1A | Low TL1A | p-Value |
| --- | --- | --- | --- |
| Gender (M/F) | 4/4 | 6/4 | NS |
| SB Stricture | 62.5% (5/8) | 10% (1/10) | 0.04 |
| Colon Stricture | 12.5% (1/8) | 20% (2/10) | NS |
| Biologic Use | 25% (2/8) | 70% (7/10) | NS |
| Failed 1 Biologic[a] | 62.8% (5/8) | 5/10 (50%) | NS |
| Failed ≥ 2 Biologics[a] | 25% (2/8) | 0% | NS |
| Immunomodulator[b] Use | 27.5% (3/8) | 60% (6/10) | NS |
| Immunomodulator[b] Failure | 75% (6/8) | 50% (5/10) | NS |
| 5-ASA[c] Failure | 87.5% (7/8) | 80% (8/10) | NS |
| Enema Use | 0% | 0% | NS |
| Ureteral Stricture | 25% (2/8) | 0% | NS |
| Previous Surgery | 87.5% (7/8) | 70% (7/10) | NS |
| TL1A (ng/mL) | 0.29 ± 0.12 | 0.08 ± 0.04 | 0.01 |
| Harvey-Bradshaw Index | 9 ± 3.45 | 2.61 ± 3.43 | <0.01 |
| Time to surgery (years) | 11 ± 10.05 | 6.75 ± 6.8 | NS |
| WBC (1000/µL) | 8.40 ± 4.34 | 8.10 ± 3.31 | NS |
| ESR (mm) | 20.64 ± 15.31 | 14.36 ± 7.20 | NS |
| CRP (mg/dL) | 1.17 ± 1.59 | 1.76 ± 3.31 | NS |

[a]Biologics include infliximab, adalimumab, certolizumab, thalidomide, and natalizumab.
[b]Immunomodulators include azathioprine, 6-mercaptopurine, methotrexate, and tacrolimus.
[c]5-ASAs include mesalamine and sulfaselazine.
Data are expressed as mean ± SD.
NS, not significant.

Example 25

TL1A Antibody Treatment in Colitis Prevention Using Adoptive T-cell Transfer Model As described, Rag1−/− deficient mice are injected with naïve T-cells to induce colitis. Application of TL1A blocking antibodies during early stages of disease onset allows measurement of efficacy of antibody treatment to prevent colitis. Following injection with naïve T-cells to induce colitis, mice receive 2 injections of antibody (either 500 µg TL1A 12F6A or isotype control) per week for 8 weeks (FIG. 38A).

Figure 38:
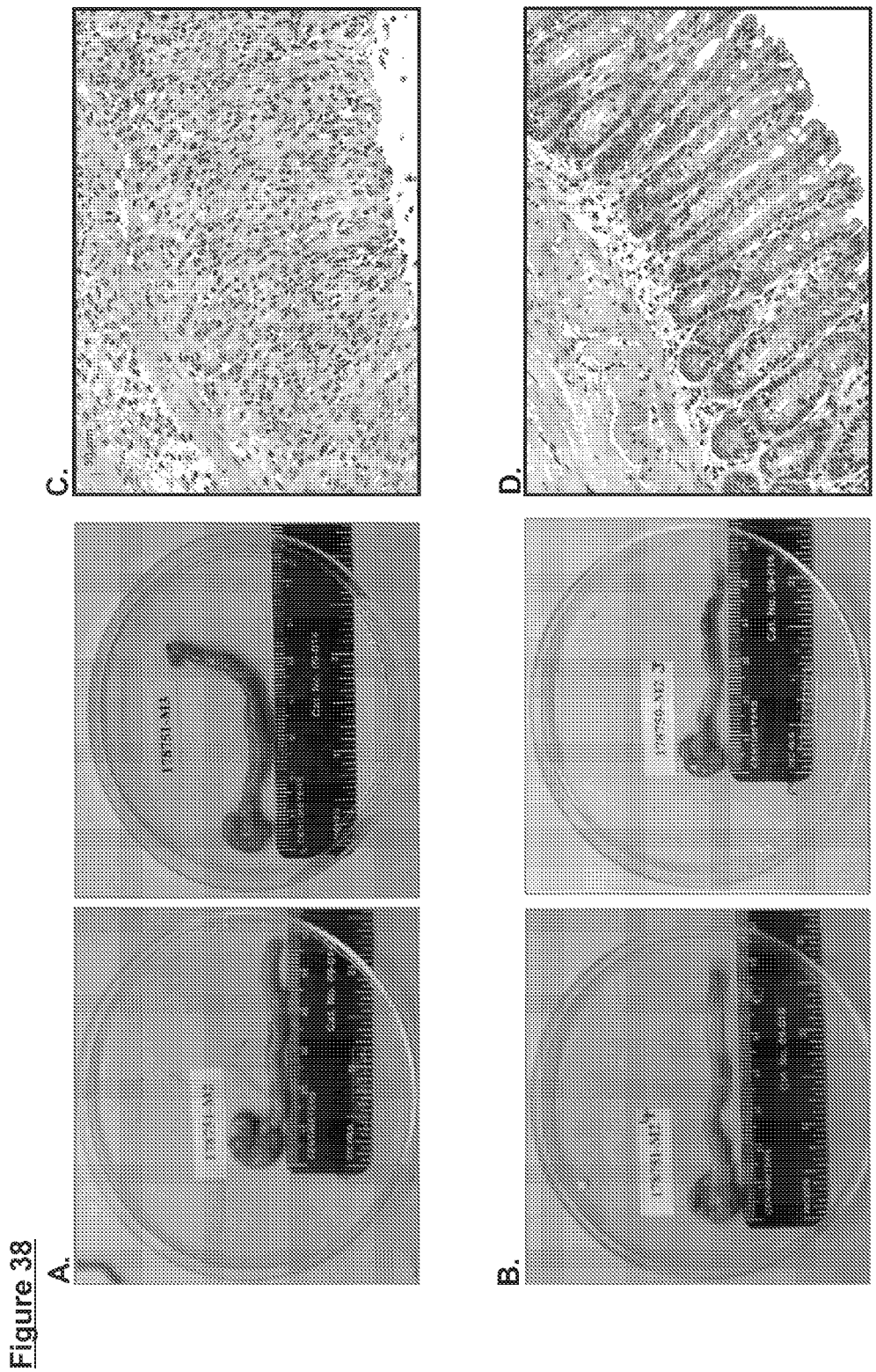
FIG. 38 depicts, in accordance with an embodiment herein, TL1A 12F6A antibody reduces gross colitis. (A) Isotype Ab treated mice display increased colon hyperemia, increased colon thickness, increased colon stiffness, and stricture with proximal dilation. (B) By contrast, TL1A 12F6A Ab treated mice display decreased colon hyperemia, decreased colon thickness, decreased colon stiffness, and no stricture or dilation., Furthermore, TL1A 12F6A antibody reduces histologic inflammation in the colon. For example, (C) isotype antibody treated shows reduced inflammation compared to (D) TL1A 12F6A antibody treated mice.
Figure 39:
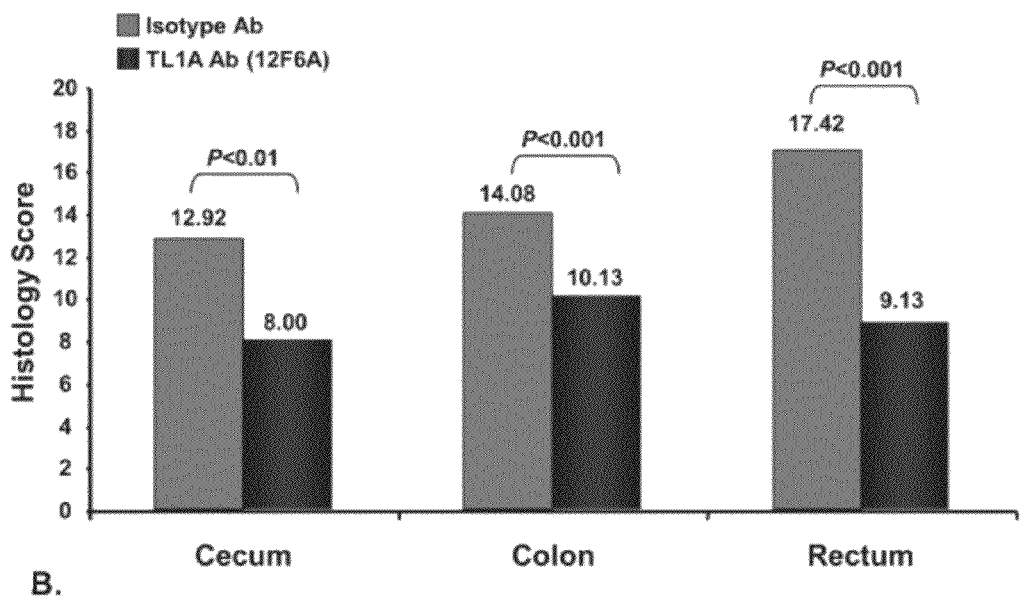
FIG. 39 depicts, in accordance with an embodiment herein, (A) TL1A 12F6A antibody reduced histologic inflammation in the colon, cecum, rectum as shown by the histology score in isotype antibody treated mice compared to TL1A 12F6A antibody treated mice, and (B) as measured by LMPC count, there is also reduced inflammatory infiltrate following TL1A 12F6A antibody treatment. p-values are indicated where significant.
Figure 39:
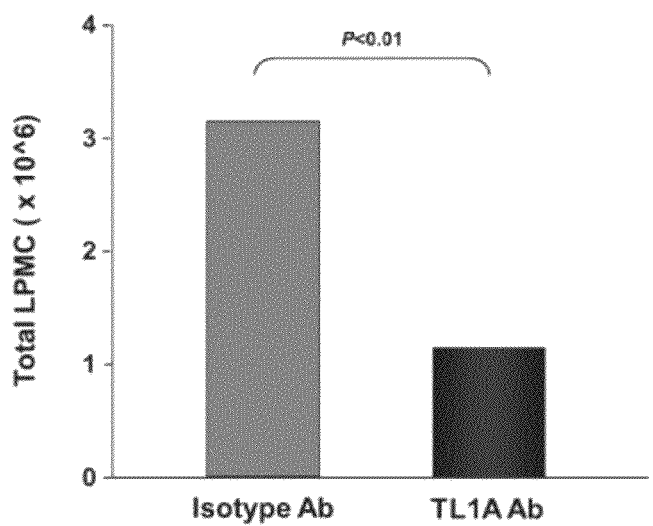
Figure 40:
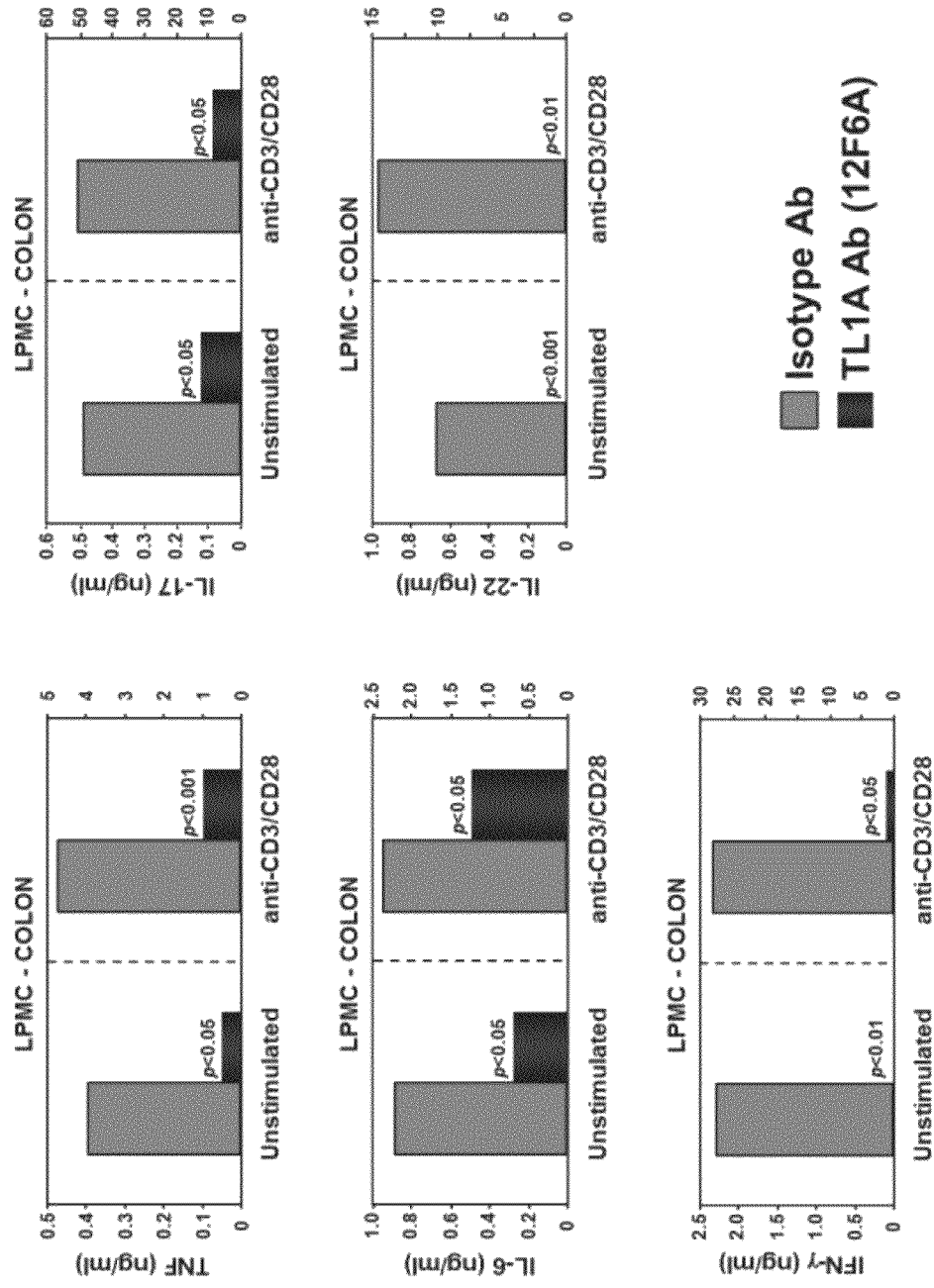
FIG. 40 depicts, in accordance with an embodiment herein, reduced Th1 and Th17-related cytokine expression in TL1A 12F6A Ab treated colon. As shown, measurements of different cytokines, including TNT-α, IL-6, IFN-γ, IL-17, and IL-22 of LPMC, in TL1A treated mice remained low, even following stimulation with anti-CD3/CD28 antibody compared to isotype Ab treated mice. p-values are indicated where significant.

The inventors observed that TL1A antibody reduces weight loss in experimental colitis and TL1A 12F6A antibody reduces disease activity index compared to isotype controls (FIGS. 38B, 38C). Further, it was observed that, TL1A 12F6A antibody reduces gross colitis. Isotype Ab treated mice display increased colon hyperemia, increased colon thickness, increased colon stiffness, and stricture with proximal dilation (FIG. 39A). (B) By contrast, TL1A 12F6A Ab treated mice display decreased colon hyperemia, decreased colon thickness, decreased colon stiffness, and no stricture or dilation (FIG. 39B). In addition, TL1A 12F6A antibody reduces histologic inflammation in the colon as shown by H&E stain. Isotype antibody treated shows reduced inflammation compared to TL1A 12F6A antibody treated mice (FIGS. 39C, 39D). This was further reflected in histology scores, wherein application TL1A 12F6A antibody reduced histologic inflammation in the colon, cecum, and rectum as shown by the histology score in isotype antibody treated mice compared to TL1A 12F6A antibody treated mice (FIG. 40A). There is also reduced inflammatory infiltrate following TL1A 12F6A antibody treatment, as measured by LPMC count (FIG. 40B).

Figure 41:
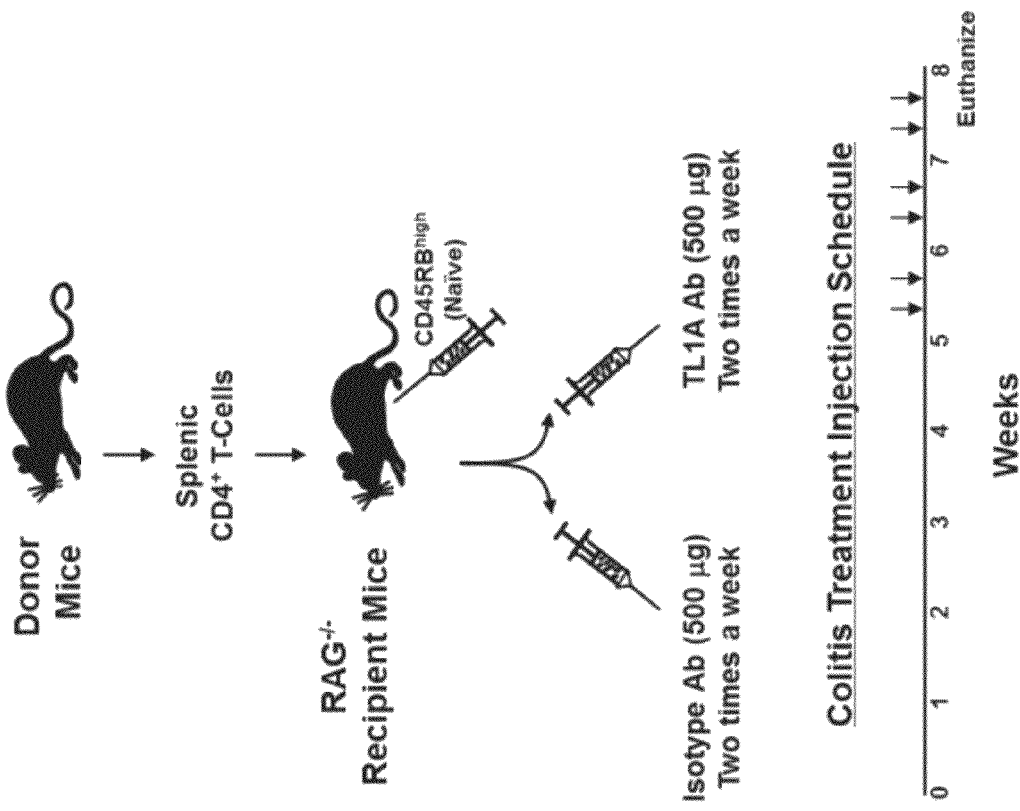
FIG. 41 depicts, in accordance with an embodiment herein, (A) general design of an in viva experiment for ameliorating established colitis, wherein Rag1−/− deficient mice are injected with naïve T-cells to induce colitis and receive 2 injections of antibody (either TL1A 12F6A or isotype control) per week for 8 weeks beginning week 5; (B) TL1A antibody reduces weight loss in established colitis; and (C) TL1A 12F6A. antibody reduces disease activity index measurements compared to isotype controls.
Figure 41:
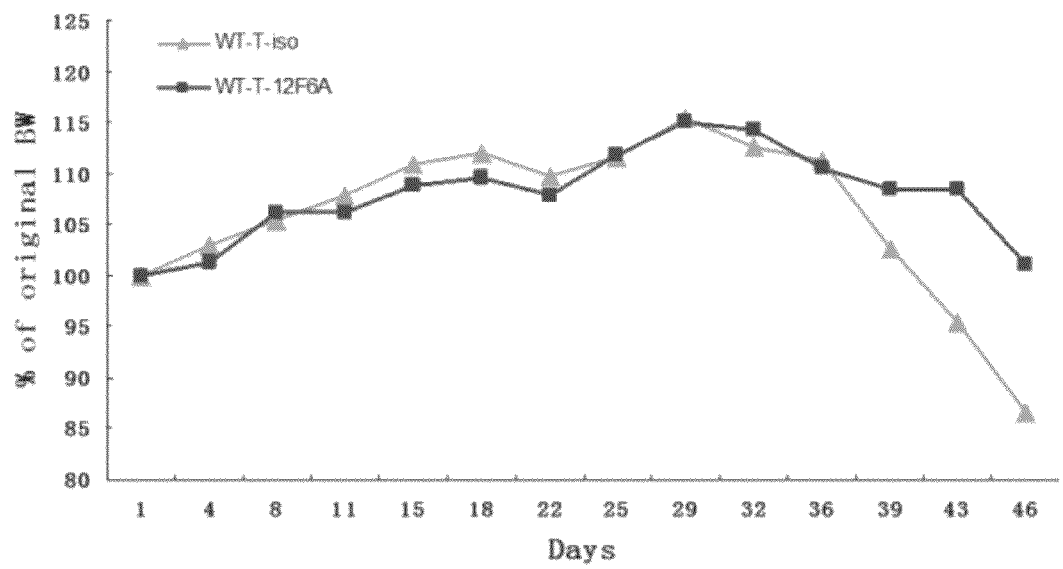
Figure 41:
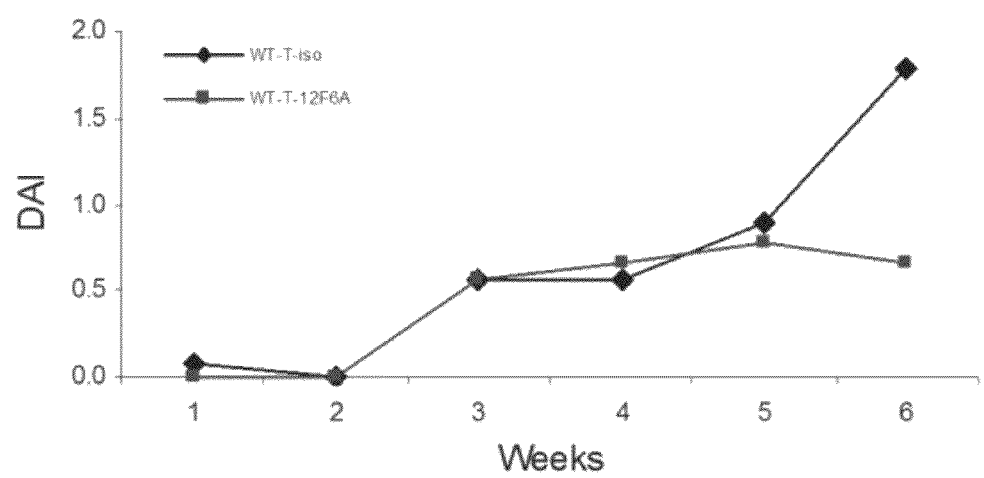

These observations were supported by molecular assays demonstrating reduced Th1 and Th17-related cytokine expression in TL1A 12F6A Ab Treated Colon. As shown, measurements of different cytokines, including TNF-α, IL-6, IFN-γ, IL-17, and IL-22 of LPMC, in TL1A treated micermained low, even following simulation with anti-CD3/CD28 antibody compared to isotype Ab treated mice (FIG. 41). Together, these results demonstrate that application of TL1A blocking antibody is effective in preventing colitis.

Example 26

Figure 42:
FIG. 42 depicts, in accordance with an embodiment herein, TL1A 12F6A antibody can ameliorate established colitis. Significant reduction in inflammation and fibrostenosis following TL1A 12F6A antibody treatment is observed after 4 weeks. In (A) isotype controls there is increased colon hyperemia, increased colon thickness, increased colon stiffness, and stricture with proximal dilation, compared to (B) TL1A 12F6A treated animals. This is further shown in samples of (C) rectal, (D) colon, and (E) cecum tissue, with isotype or TL1A 12F6A antibody treatment as indicated.
Figure 42:
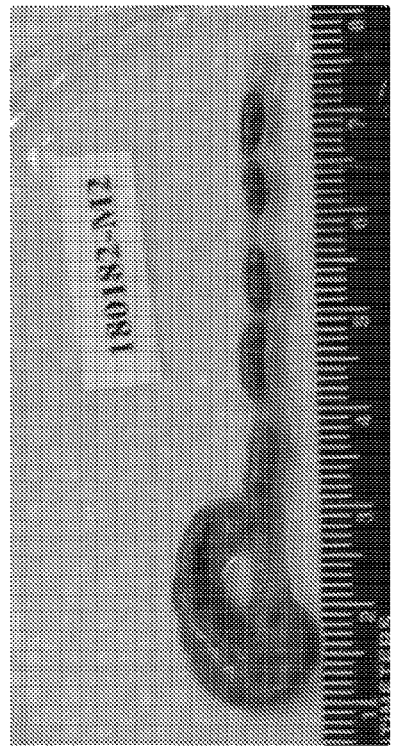
Figure 42:
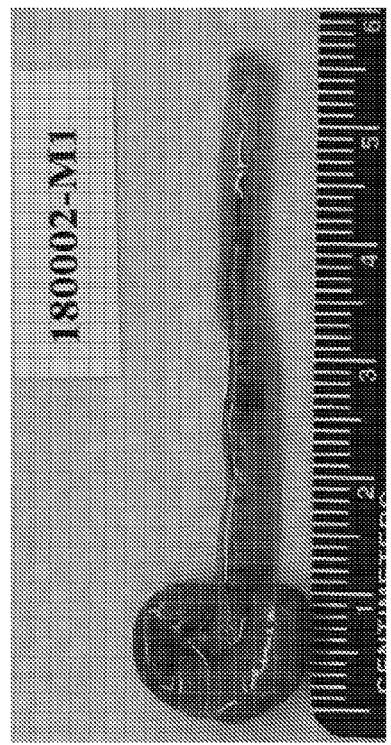
Figure 42:
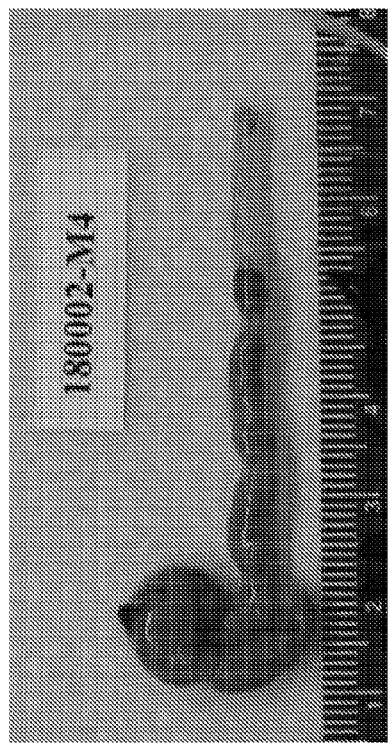
Figure 42:
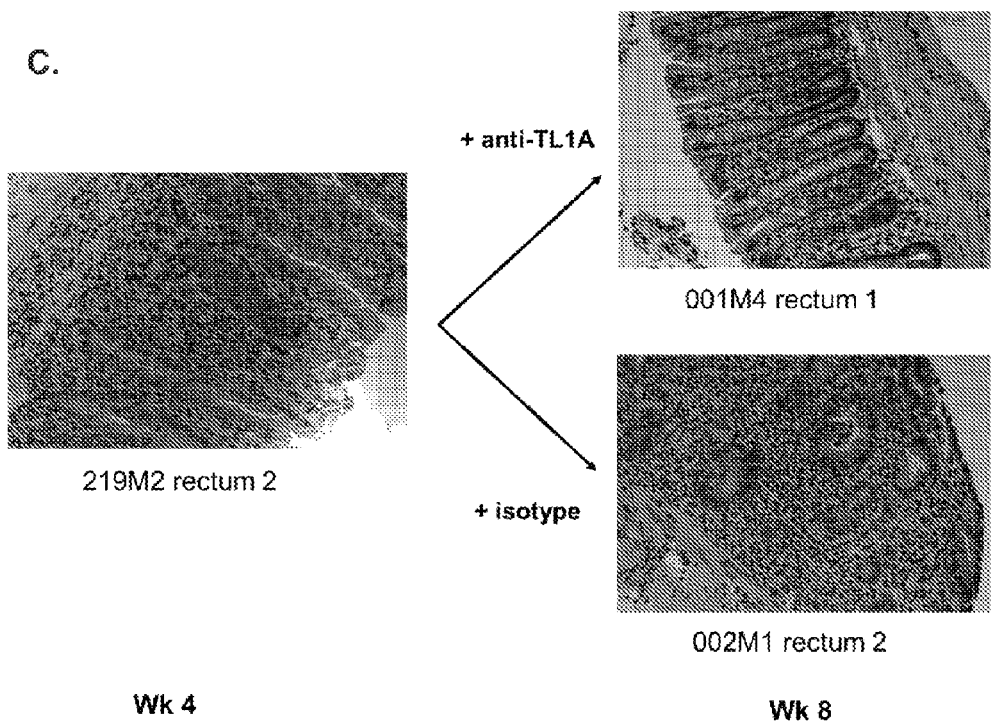
Figure 42:
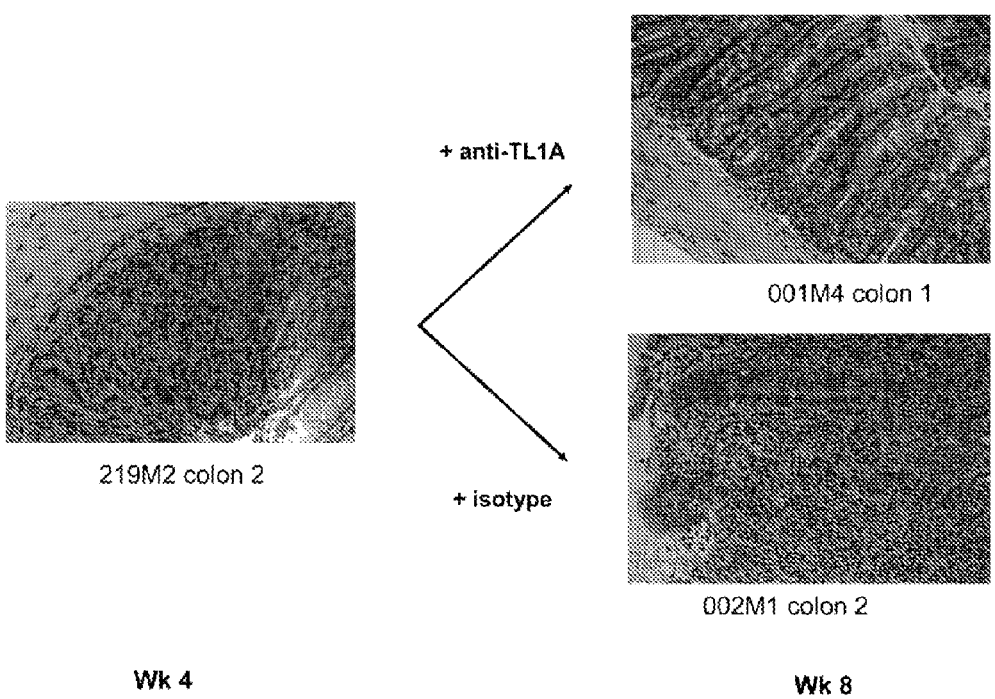
Figure 42:
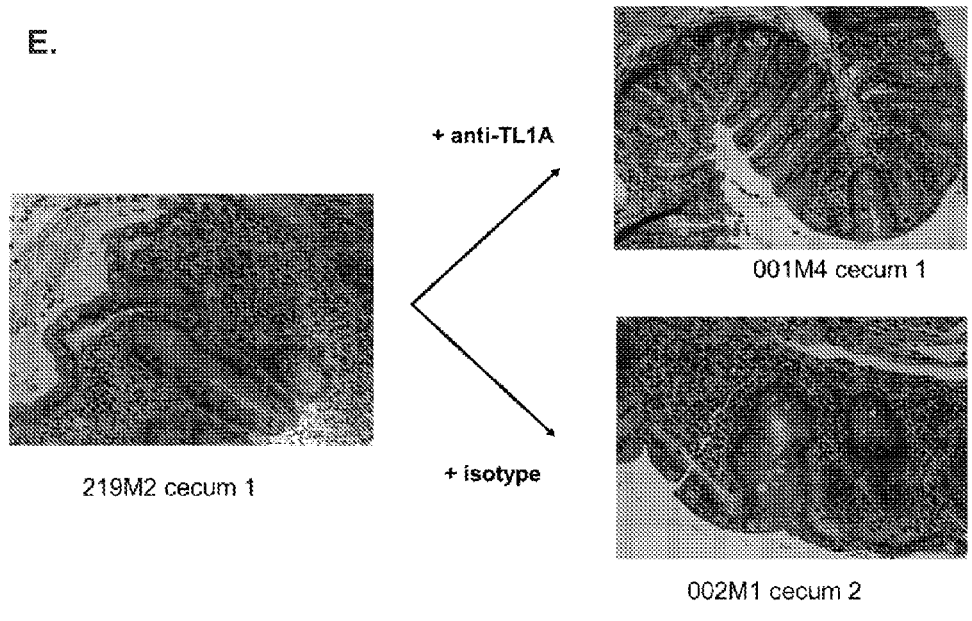

TL1A Antibody Treatment in Established Colitis Using Adoptive T-cell Transfer Model Application of TL1A blocking antibodies may be delayed in the adoptive T-cell transfer model to assess how blocking of TL1A function may ameliorate established colitis. In this model, Rag1−/− deficient mice again are injected with naïve T-cells to induce colitis. However, application of blocking antibodies is delayed until week 5, wherein 2 injections of antibody (either 500 μg TL1 A 12F6A or isotype control) per week for 8 weeks are applied (FIG. 42A). Similar to the colitis prevention model, TL1A antibody effectively reduces weight loss in established colitis, and further reductions in DAI are observed following TL1A 12F6A antibody treatment, compared to isotype controls (FIGS. 42B, 42C).

Figure 43:
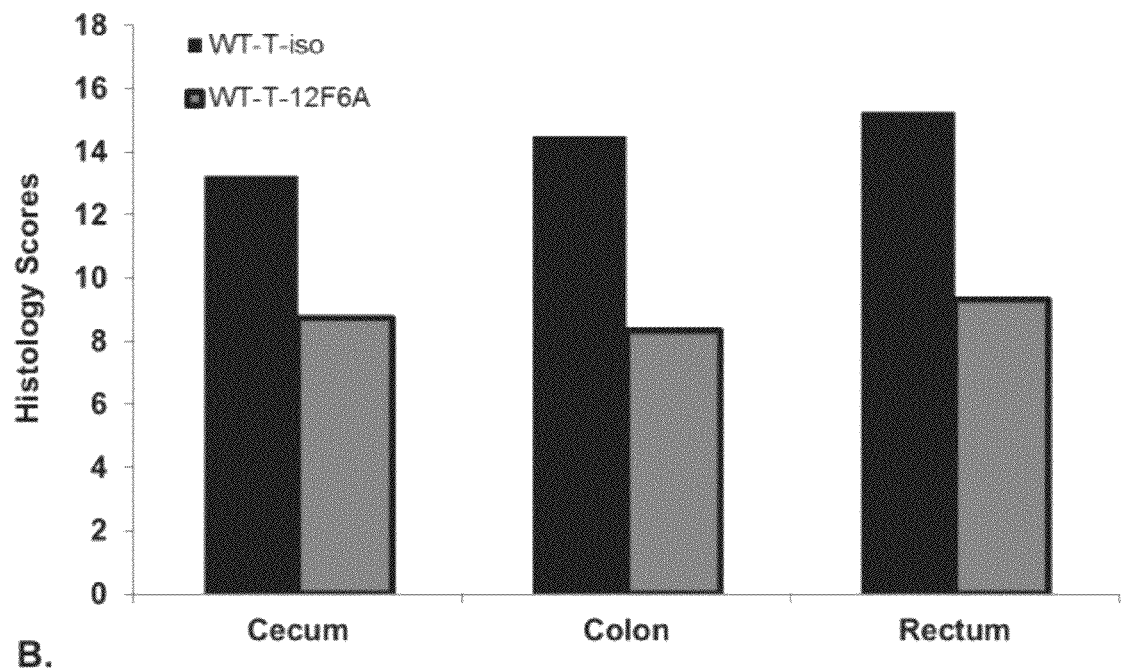
FIG. 43 depicts, in accordance with an embodiment herein, (A) TL1A 12F6A antibody reduced histologic inflammation in the colon, cecum, rectum in established colitis as shown by the histology score in isotype antibody treated mice compared to TL1A 12F6A antibody treated mice. (B) As measured by LMPC count, there is also reduced inflammatory infiltrate following TL1A 12F6A antibody treatment for established colitis.
Figure 43:
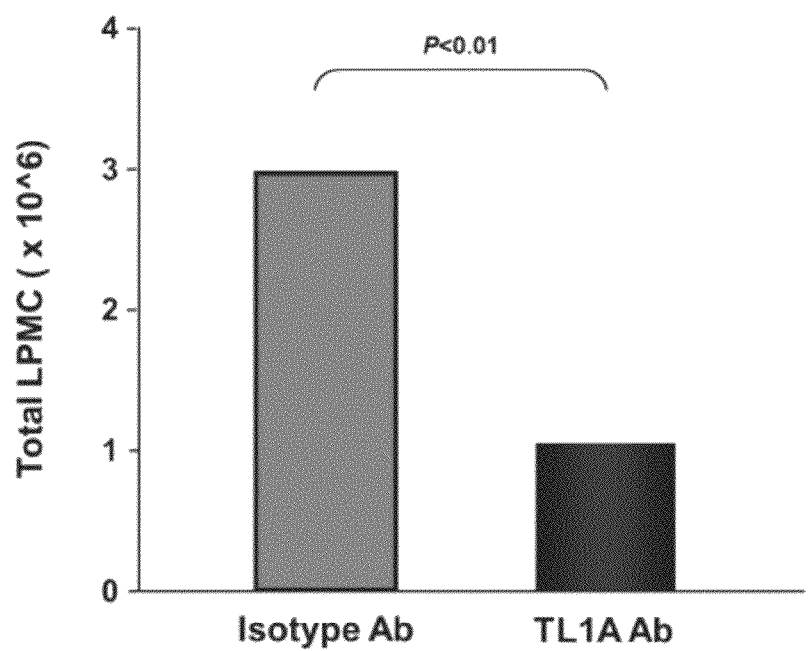
Figure 44:
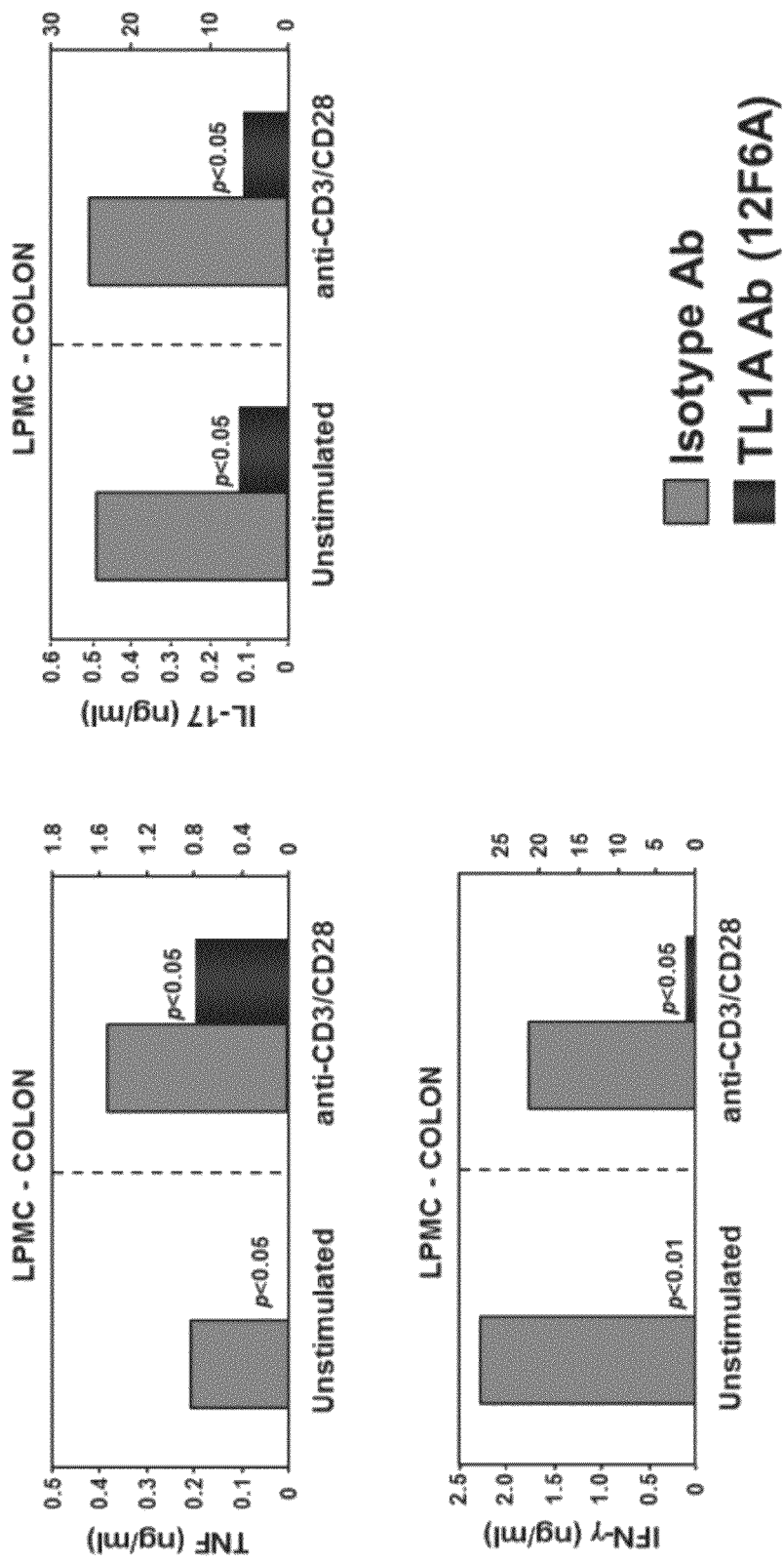
FIG. 44 depicts, in accordance with an embodiment herein, reduced Th1 and Th17-related cytokine expression in TL1A 12F6A Ab treated colon in established colitis. As shown, measurements of different cytokines, including TNF-$\alpha$, IL-6, IL-17, and IL-22 of LPMC, in TL1A treated mice remained low, even following stimulation with anti-CD3/CD28 antibody compared to isotype Ab treated mice. p-values are indicated where significant.
Figure 45:
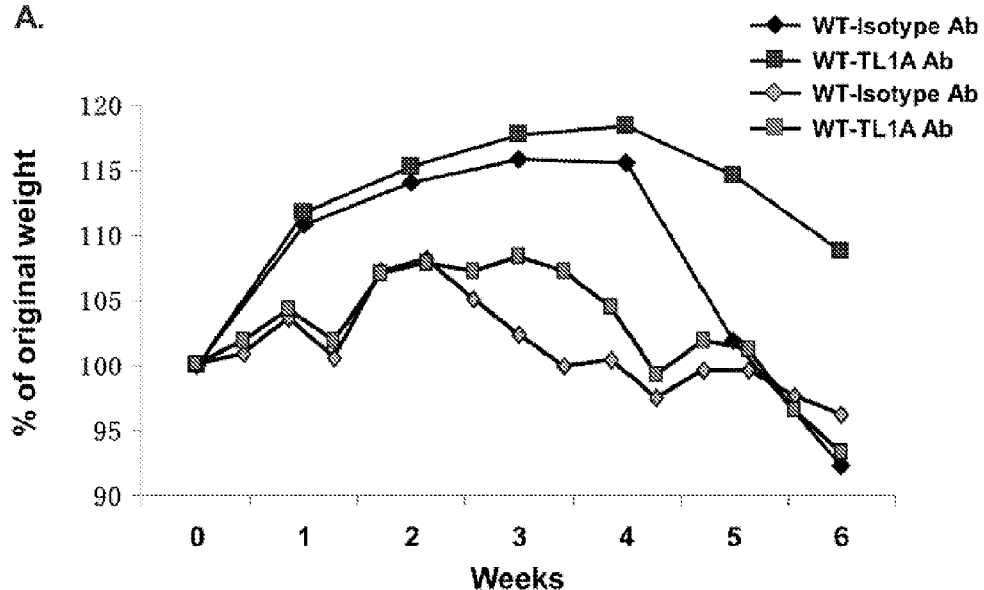
FIG. 45 depicts, in accordance with an embodiment herein, results of an in vivo experiment for antibody treatment of Rag1−/− deficient mice receiving L-Tg T-cells constitutively expressing TL1A. Unlike colitis prevention and established colitis models described, application of TL1A P12F6A antibody provides less effective results in an adoptive-transfer model using T-cells derived from L-Tg mice. (A) For example, mice receiving TL1A expressing T-cells continue experiencing weight loss. (B) There is also continued progression of disease as measured by disease-activity index (DAT).
Figure 45:
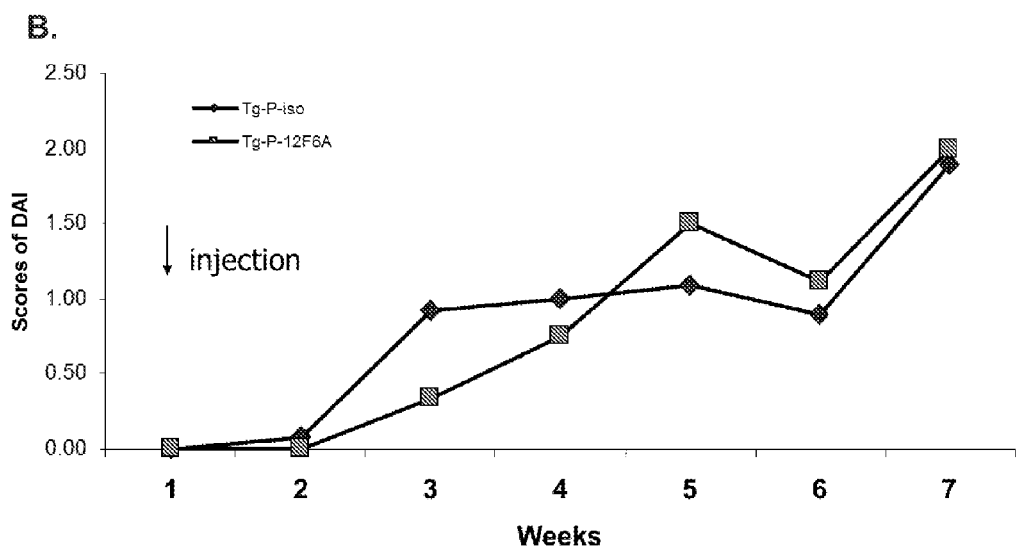

The inventors further observed in histological sections that TL1A 12F6A antibody can ameliorate established colitis. Significant reduction in inflammation and fibrostenosis Wowing TL1A 12F6A antibody treatment was observed after 4 weeks. In isotype controls there is increased colon hyperemia, increased colon thickness, increased colon stiffness, and stricture with proximal dilation, compared to TL1A 12F6A treated animals (FIGS. 43A, 43B). Staining using H&E demonstrated that there was significant improvement following TL1A 12F6A antibody treatment compared to isotype controls in rectal, colon, and cecum tissue (FIGS. 43C-E). This was confirmed by histological scoring, wherein TL1A 12F6A antibody treatment reduced histologic inflammation in the colon, cecum, rectum in established colitis (FIG. 44A). Inflammatory infiltrate was also reduced, as measured by LMPC count, following TL1A 12F6A antibody treatment (FIG. 44B). Molecular assays further show significant reduction in Th1 and Th17-related cytokine expression in TL1A 12F6A Ab treated colon in established colitis. As shown, measurements of different cytokines, including TNF-α, IL-6, IFN-γ, IL-17, and IL-22 of LPMC, in TL1A treated miceremained low, even following simulation with anti-CD3/CD28 antibody compared to isotype Ab treated mice (FIG. 45). Together, these results demonstrate that application of TL1A blocking antibody is effective in ameliorating established colitis.

Example 27

Figure 46:
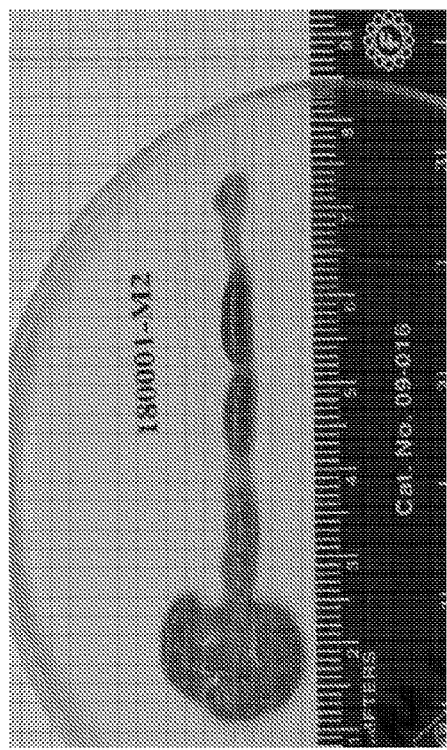
FIG. 46 depicts, in accordance with an embodiment herein, results of an in vivo experiment for antibody treatment of Rag1−/− deficient mice receiving L-Tg T-cells constitutively expressing TL1A. In (A) isotype controls there is increased colon hyperemia, increased colon thickness, increased colon stiffness, and stricture with proximal dilation as expected, with only mild improvement observed in (B) TL1A 12F6A treated animals, as shown by representative samples.
Figure 46:
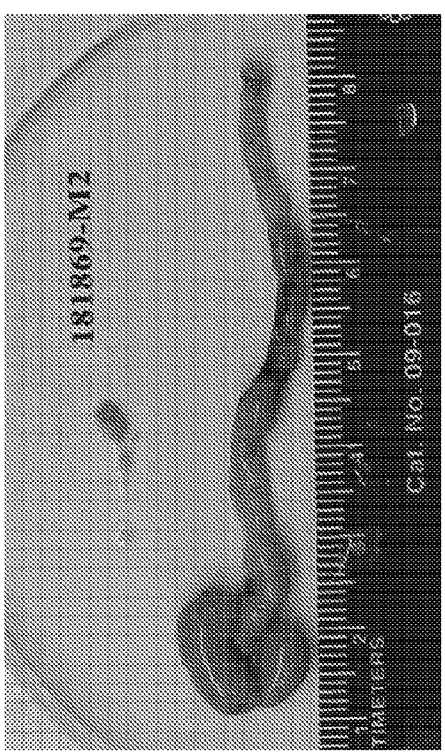
Figure 46:
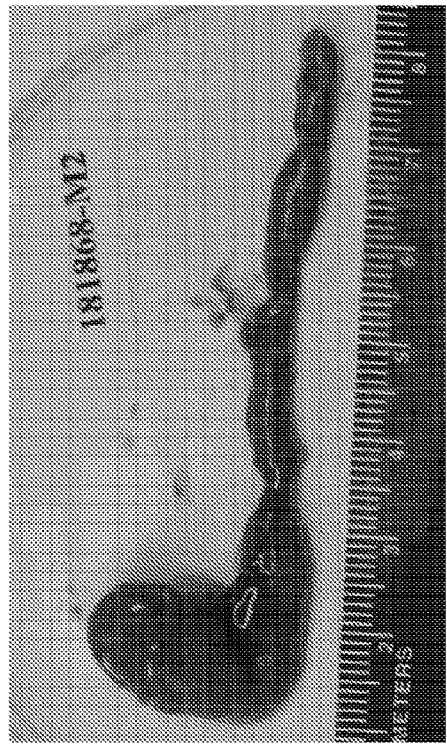
Figure 46:

TL1A Antibody Treatment Using Adoptive T-cell Transfer Model, Including L-Tg T-cells Constitutively Expressing TL1A Whereas the aforementioned techniques inject Rag1−/− deficient mice with naive T-cells, generation of L-Tg mice allows injection of T-cells constitutively expressing TL1A. Interestingly, the inventors observed that unlike colitis prevention and established colitis models described, application of TL1A P12F6A antibody provides less effective results in adoptive-transfer model using T-cells derived from L-Tg mice. For example, mice receiving TL1A expressing T-Cells continue experiencing weight loss and here is also continued progression of disease as shown by DAI measurements (FIGS. 46A, 46B).

Figure 47:
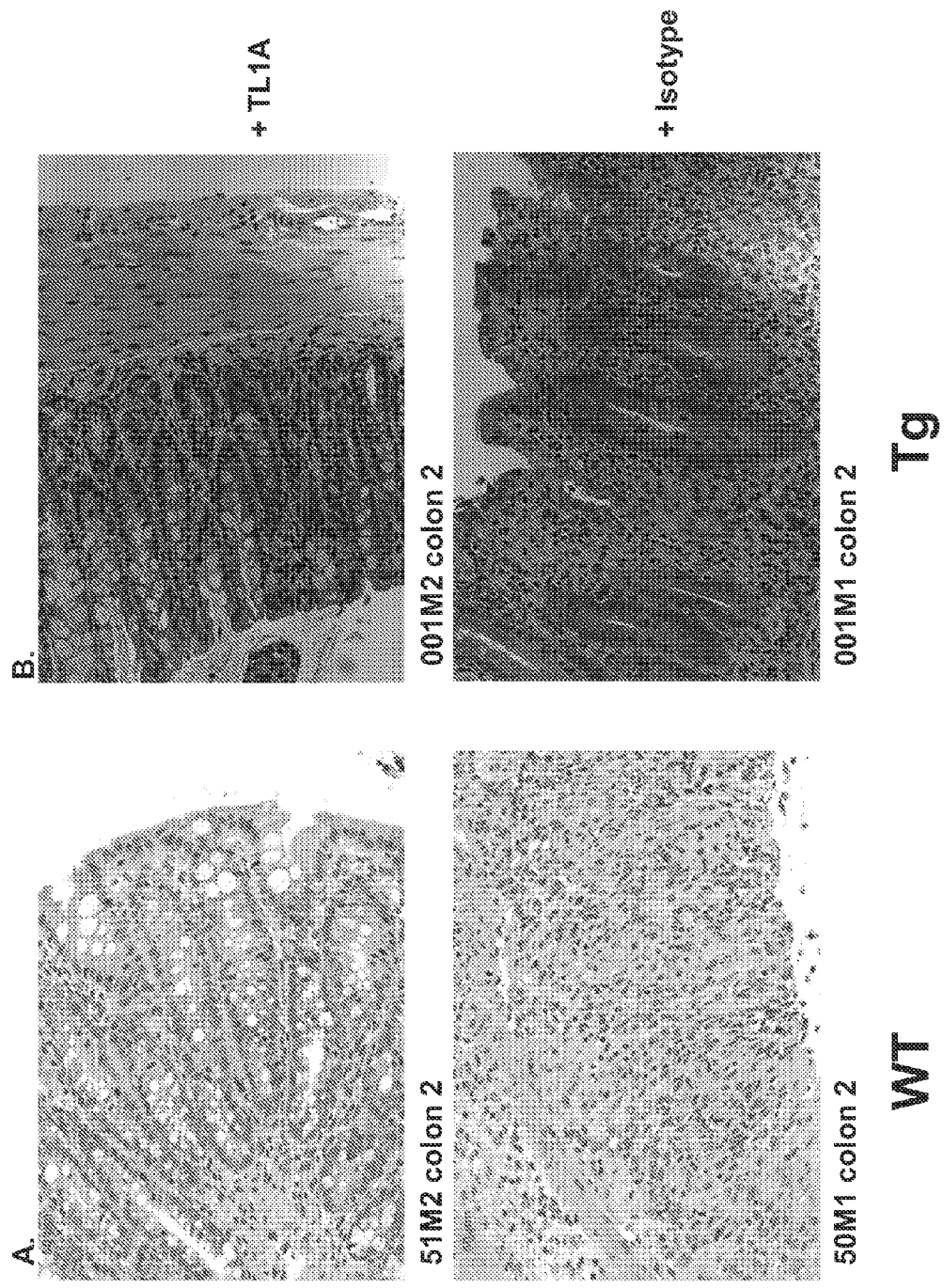
FIG. 47 depicts, in accordance with an embodiment herein, results of antibody treatment of Rag1−/− deficient mice receiving L-Tg T-cells constitutively expressing TL1A. Application of TL1A P12F6A antibody improves conditions in WT mice and mice receiving T-cells constitutively expressing TL1A. (A) WT animal controls show hyperemia in colonic sample after treatment with isotype controls, which is reduced following application of TL1A P12F6A antibody as shown. (B) Disease progression is present in mice receiving T-cells constitutively expressing TL1A, although improvement is shown in TL1A 12F6A treated animals, as shown by representative samples.
Figure 48:
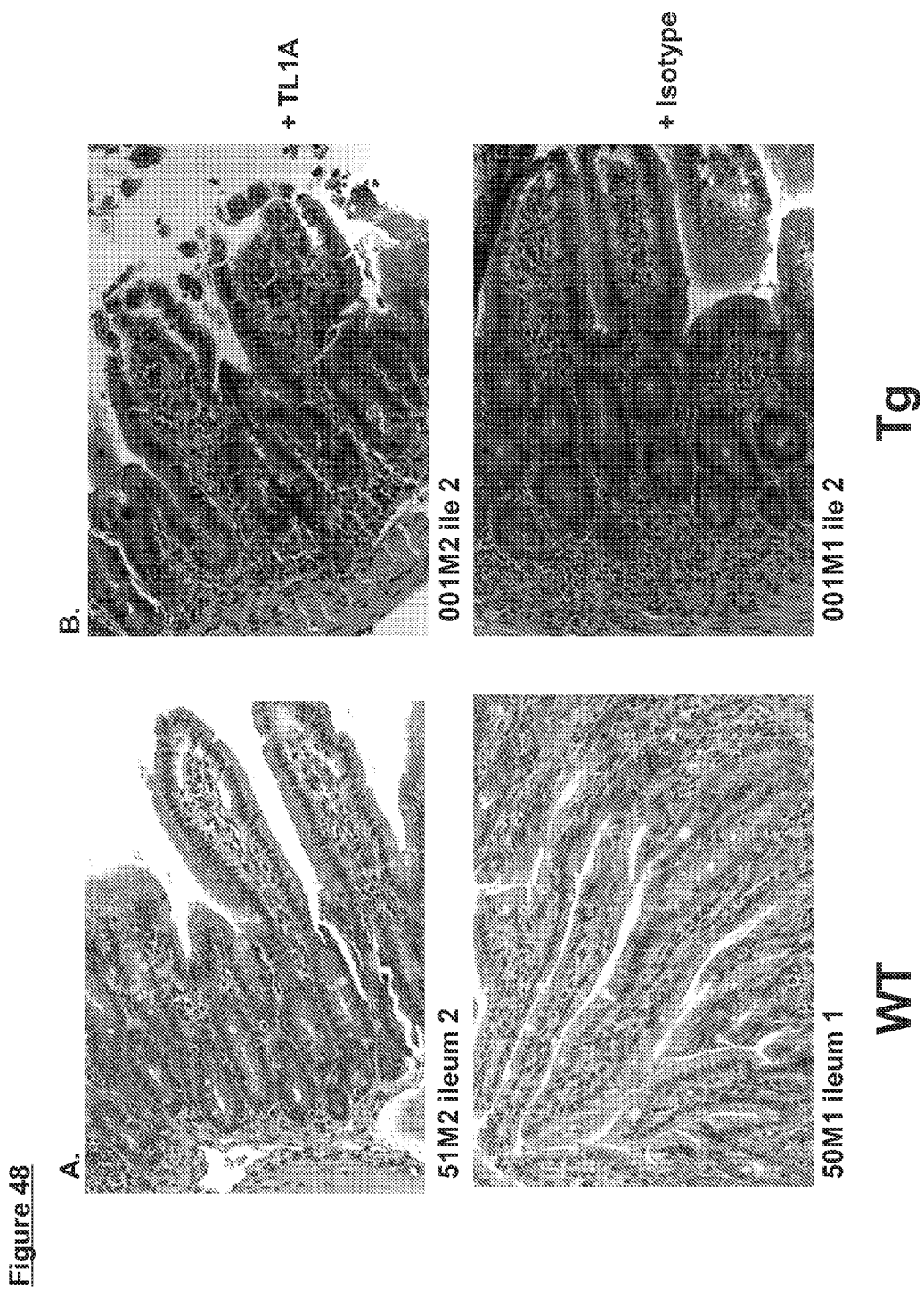
FIG. 48 depicts, in accordance with an embodiment herein, results of antibody treatment of Rag1−/− deficient mice receiving L-Tg T-cells constitutively expressing TL1A. (A) WT animal controls show mild hyperemia after treatment with isotype antibody, and improvement after treatment with TL1A 12F6A. antibody as shown. (B) Disease progression is present in mice receiving T-cells constitutively expressing TL1A regardless of whether isotype or TL1A 12F6A blocking antibody is applied, as shown by representative samples.

Further, although inventors observed increased colon hyperemia, increased colon thickness, increased colon stiffness, and stricture with proximal dilation as expected in mice treated with isotype antibody controls there is also only mild improvement observed in TL1A 12F6A treated animals (FIGS. 47A, 47B). Closer inspection of histological sections demonstrated that WT animal controls possessed hyperemia in colonic samples after treatment with isotype controls, with a mild reduction following application of TL1A P12F6A antibody (FIG. 48A). Disease progression was present in both wild-type mice receiving T-cells constitutively expressing TL1A, with TL1A antibody or isotype antibody treatment, although some improvement is shown in TL1A 12F6A treated animals (FIG. 48B). In the ileum, WT animals possessed mild hyperemia after treatment with isotype antibody, and some improvement after treatment with TL1A 12F6A antibody as shown, However, disease progression was apparent in mice receiving T-cells constitutively expressing TL1A regardless of whether isotype or TL1A 12F6A blocking antibody is applied, as shown by representative samples.

Example 28

In vivo Study Results: Discussion

This study showed that elevated TL1A expression resulted in severe patchy intestinal inflammation with proximal migration of colonic inflammation under colitogenic conditions. Furthermore, TL1A Tg mice spontaneously developed ileitis, but not colitis by 10 months of age. [16, 17, 57] The severity of ileitis was more dramatic in induced chronic colitis models, (DSS and adoptive transfer). As colitis is the predominant gut pathology seen in both the DSS and adoptive-transfer models, ileitis reported in this study was likely driven by constitutive TL1A expression. Depending on the model, TL1A expression led to either additional inflammation in the jejunum (DSS) or duodenum (adoptive-transfer).

Constitutive TL1A expression also altered the colitis pattern from the more distal recto-sigmoid inflammation to the more proximal cecal inflammation. These inflammatory changes are likely caused by TL1A and not the cell type that expresses TL1A as both L-Tg and M-Tg mice exhibited a similar pattern of inflammation. Relative sparing of rectal inflammation was seen in the adoptive-transfer model using TL1A Tg T-cells. TL1A is a severity gene, which when overexpressed results in a change in location to the proximal parts of the colon and small intestine, and away from the rectum. Prior studies reported that TL1A is associated with expansion of T-helper subsets and can synergize with IL-12 and -18 to enhance Th-1 response and IFN-γ production.[4, 5, 66, 67] Other investigations found that mice lacking TL1A display reduced experimental encephalitis disease activity which is associated with decreased Th-17 cell differentiation and proliferation. [12] Consistently, in DSS-induced models of chronic colitis, TL1A enhances Th-1 and -17 effector functions by up-regulating IFN-γ and IL-17 production, respectively, in CD4+ T-cells under Th1/Th17 polarizing conditions. [9] TL1A had also been found to be involved in Th-2 mediated Ova-induced lung disease and in spontaneous ileitis. [11, 16, 17] These reports indicated that the TL1A/DR3 signaling pathway may have a universal role in regulating T-helper effector outcomes.

Increased IL-17 production was found in DSS-induced chronic colitis with constitutive TL1A expression. [9] in the adoptive-transfer model, TL1A expression led to a Th-1 dominant immune response with almost a complete absence of IL-17 production. The differences in the T-helper response may be based on the differentiation state of the CD4+ T-cells. In the DSS-induced chronic colitis model, TL1A can enhance the effector characteristics of committed Th17 cells. In the adoptive transfer model, TL1A/DR3 signaling may inhibit Th-17 development in newly challenged naïve T-cells. Differential responsiveness of naïve and committed T-cells to TL1A/DR3 signaling had also been recently proposed. [58] Another explanation for the different TL1A dependent T-helper immune response between the DSS and adoptive T-cell transfer models may be different gut microflora. We bred WT and TL1A Tg littermates in our facility for the DSS-induced chronic colitis experiments. For the adoptive-transfer model, we purchased. Rag1−/− recipient mice from Jackson Laboratory. Previous studies had demonstrated that genetically identical inbred mice raised in different animal facilities had different immune composition due to the 17 different gut microflora, [68-70] The potential immunomodulatory roles of gut microbia-host interaction between mice may have contributed to the different TL1A mediated T-helper immune response.

Figure 30:
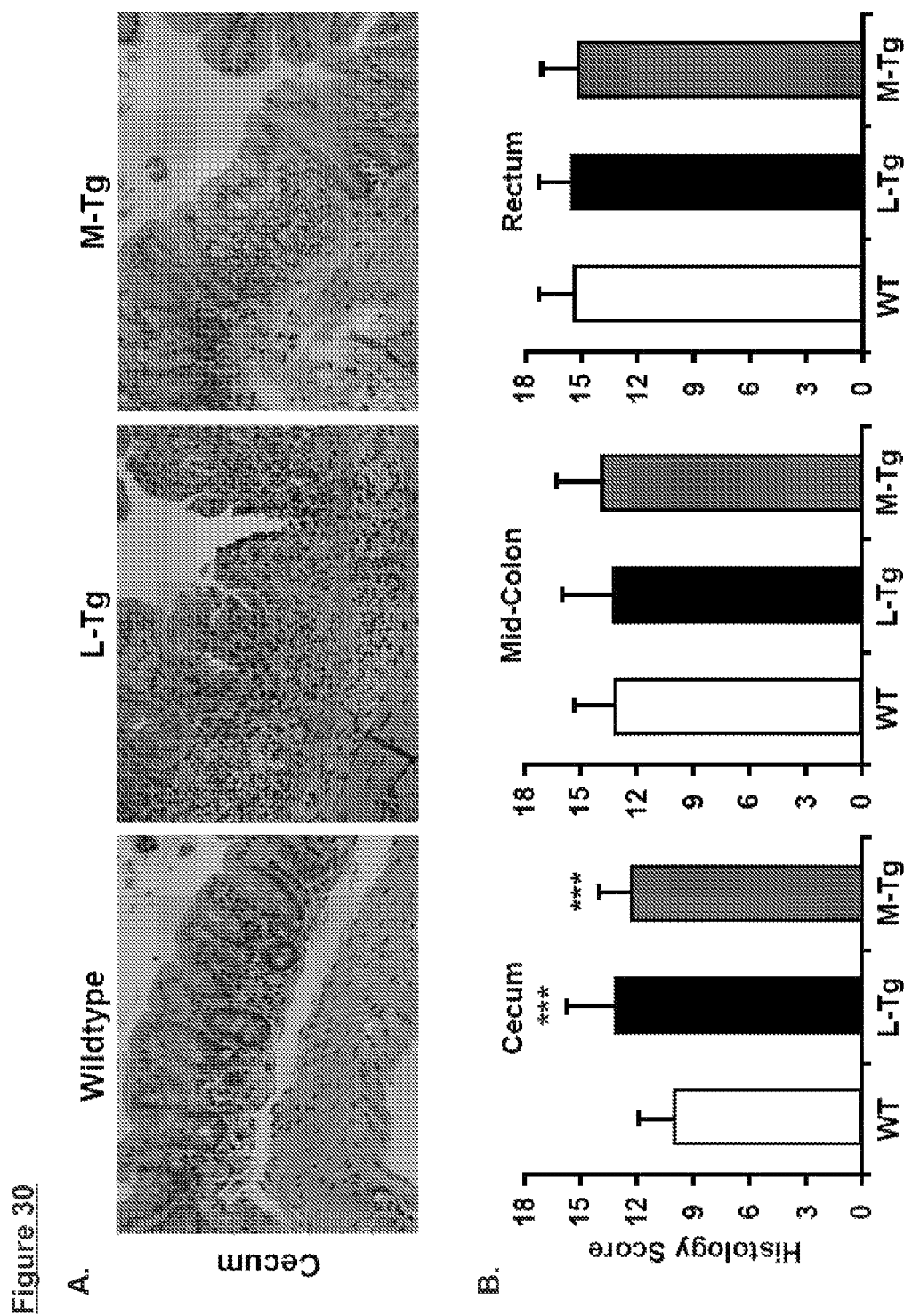
FIG. 30 depicts, in accordance with an embodiment herein, L-Tg and M-Tg mice have proximal migration of colonic inflammation. Representative EISLE stained DSS (A) and adoptive transfer (C) colonic sections are shown. Histology scores for DSS (B) and adoptive transfer (D) were assessed. (E) Representative colonic specimen showing proximal migration of gross inflammation in the mice receiving L-Tg T-cells compared to WT T-cells. Data are expressed as mean±SD. Fields at 200× magnification were scored. ***$p<0.001$.
Figure 30:
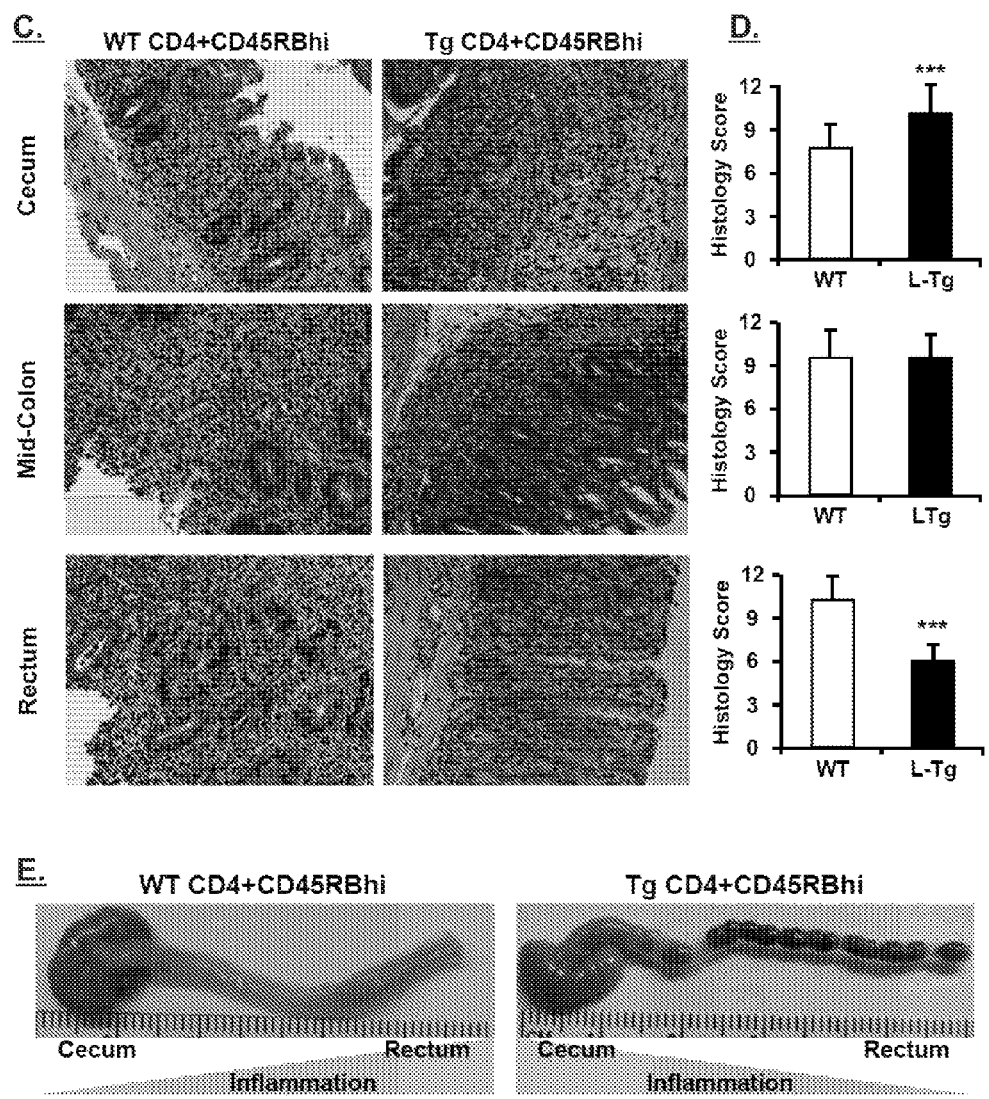

Compared to WT mice, increased collagen deposition was observed in older TL1A Tg mice. [57] Notably, the severity of fibrosis was worse in the induced chronic colitis models with constitutive TL1A expression where gross (not just histologic) colonic and intestinal strictures were observed. This may reflect the fact that the induced chronic colitis models led to an accelerated T-helper effector function where effector phase of the disease is reached earlier. In addition, TL1A may be an independent pro-fibrogenic gene to initiate the process of fibrosis since we previously found that TL1A expression resulted in increased colonic collagen deposition in the absence of detectable histologic inflammation. [67] Furthermore, in the current study, visible colonic strictures were observed in the mid-colon of only the TL1A Tg mice despite a similar degree of inflammation as compared to WT mice (FIGS. 30, 31). The pro-fibrotic effects of TL1A may be mediated. by TGF-$\beta$1 as its expression was increased in the non-structured colon of Tg compared to WT mice (FIG. 32C). However, other factors are likely involved and need to be explored further. The TL1A-Tg animal models, L-Tg and M-Tg transgenic mice, are the only in vivo model where overexpression of a single IBD associated gene lead to both gross intestinal and colonic fibrostenotic disease that is observed in Crohn's disease.

Compared to CD patients with low TL1A expression, higher TL1A producing CD patients had increased inflammation in the ileum and cecum with reduced inflammation in the sigmoid and rectum (FIG. 36). None of the CD patients in our study cohort used rectally-administered IBD therapy, therefore, the reduction in recto-sigmoid inflammation may be due to elevated TL1A expression. A significantly higher rate of intestinal strictures was found in CD patients with higher TL1A levels (Table 1), suggesting that TL1A may induce intestinal strictures in humans. This is consistent with previous reports showing that TL1A haplotype-B, which is associated with increased TL1A levels, is also characterized by increased need for surgery due to fibrostenotic CD disease. [4, 23] One limitation of the retrospective analysis is the small sample size, thus our findings need to be confirmed in an independent prospective study. Extraintestinal manifestations of CD can be seen including arthropathy, erythema nodosum, and more rarely hydronephrosis due to strictures along the genitourinary tract. [53, 71, 72] The presence of IBD-like skin lesions and arthropathy in older TL1A Tg mice were reported.11 In this study, hydronephrosis due to ureteral strictures was only observed in TL1A Tg mice during the development of chronic colitis (7%, 3/43). Ureteral involvement has been reported to occur in 3-6% of CD cases. [72] Interestingly, a higher frequency of ureteral structuring was found in our small cohort of CD patients expressing higher TL1A level (25%, 2/8, Table 1), suggesting that TL1A may also cause ureteral fibrosis.

In summary, TL1A modulates the severity and location of inflammation in the intestine and colon under colitogenic conditions. Sustained TL1A expression also induces structuring disease in the gut that is caused by increased collagen deposition and number of fibroblasts. Results from these TL1A Tg experimental models coupled with findings in CD patients suggest that TNFSF15 is a severity gene and that the cytokine TL1A, when over expressed, plays a central role generating one phenotypic form of complicated of CD.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the constructs for generating TL1A Tg mice, animal models based on TL1A expression, cells derived from such animal models, diagnostic and therapeutic approaches related to TLA1A and IBD, fibrosis and/or other diseases and conditions and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed, No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. it is contemplated that skilled artisans can employ such variations as appropriate, and the invention can be practiced otherwise than specifically described herein.

Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES

1. Shih D Q, Targan S R (2009) Insights into IBD Pathogenesis. Curr Gastroenterol Rep 11: 473-480.
2. Shih D Q, Targan S R, McGovern D (2008) Recent advances in IBD pathogenesis: genetics and immunobiology. Curr Gastroenterol Rep 10: 568-575.
3. Stappenheck T S, Rioux J D, Mizoguchi A, Saitoh T, Huett A, et al. (2010) Crohn disease: A current perspective on genetics, autophagy and immunity, Autophagy 7: Epub ahead of print.
4. Prehn J L, Mehdizadeh S. Landers C J, Luo X. Cha S C, et al. (2004) Potential role for TL1A, the new TNF-family member and potent costimulator of IFNgamma, in mucosal inflammation. Clin Immunol 112: 66-77.
5. Papadakis K A, Prehn J L, Landers C, Han Q, Luo X, et al. (2004) TL1A synergizes with IL-12 and IL-18 to enhance IFN-gamma production in human T-cells and NK cells. J Immunol 172: 7002-7007.
6. Cassatella M A, Pereira-da-Silva G, Tinazzi I, Facchetti F, Scapini P, et al. (2007) Soluble TNF-like cytokine (TL1A) production by immune complexes stimulated monocytes in rheumatoid arthritis, J Immunol 178: 7325-7333.
7. Prehn J L, Thomas L S, Landers C J, Yu Q T, Nilichelsen K S, et al (2007) The T cell costimulator TL1A is induced by FcgammaR signaling in human monocytes and dendritic cells. J Immunnol 178: 4033-4038.
8. Shih D Q, Kwan L Y, Chavez V. Cohavy O, Gonsky R, et al, (2009) Microbial induction of inflammatory bowel disease associated gene TL1A (TNFSF15) in antigen presenting cells. Eur Immunol 39: 3239-3250.
9. Takedatsu H, Michelson K S, Wei B, Landers C J, Thomas L S, et al. (2008) TL1A (TNFSF15) regulates the development of chronic colitis by modulating both T-helper 1 and T-helper 17 activation, Gastroenterology 135: 552-567.
10. Meylan F, Davidson T S, Kahle E, Kinder M, Acharya K, et al. (2008) The TNF-family receptor DR3 is essential for diverse T cell-mediated inflammatory diseases. Immunity 29: 79-89.
11. Fang L, Adkins B, Deyev V, Podack E R (2008) Essential role of TNF receptor superfamily 25 (TNFRST25) in the development of allergic lung inflammation. J Exp Med 205: 1037-1048.
12. Pappu B P, Borodovsky A, Zheng T S, Yang X, Wu P, et al. (2008) TL1A-DR3 interaction regulates Th17 cell function and Th17-mediated autoimmune disease. J Exp Med 205: 1049-1062.
13. Bamias G, Mishina M. Nyce M, Ross W G, Koilias G, et al. (2006) Role of TL1A and its receptor DR3 in two models of chronic murine ileitis. Proc Natl Acad Sci USA 103: 8441-8446.
14. Papadakis K A, Zhu D, Prehn J L, Landers C, Avanesyan A, et al. (2005) Dominant role for TL1A/DR3 pathway in IL-12 plus IL-18-induced IFNgamma production by peripheral blood and mucosal CCR9+ T lymphocytes, J Immunol 174: 4985-4990.
15. Bamias G, Martin C, 3rd, Marini M, Hoang S, Mishina M, et al. (2003) Expression, localization, and functional activity of TL1A, a novel Th1-polarizing cytokine in inflammatory bowel disease. J Immunol 171: 4868-4874.
16. Meylan F, Song Y J, Fuss I, Villarreal S, Kahle E, et al. (2010) The TNF-family cytokine TL1A drives IL-13-dependent small intestinal inflammation, Mucosal Immunol: Epub ahead of print.
17. Taraban V Y, Slebioda T J, Willoughby J E, Buchan S L, James S, et al. (2010) Sustained TL1A expression modulates effector and regulatory T-cell responses and drives intestinal goblet cell hyperplasia. Mucosal Immunol; Epub ahead of print.
18. Sasmono R T, Oceandy D, Pollard J W, Tong W, Pavli P, et al. (2003) A macrophage colony-stimulating factor receptor-green fluorescent protein transgene is expressed throughout the mononuclear phagocyte system of the mouse, Blood 101: 1155-1163.
19. Wang J, Lo J C, Foster A, Yu P, Chen H M, et al, (2001) The regulation of T cell homeostasis and autoimmunity by T cell-derived LIGHT. J Clin invest 108: 1771-1780.
20. Rachmilewitz D, Karmeli F, Shteingart S, Lee J, Takabayashi K, et al. (2006) Immunostimulatory oligonucleotides 21. Ostanin D V, Pavlick K P, Bharwani. S. D'Souza D, Furr K L, et al. (2006) T cell induced inflammation of the small and large intestine in immunodeficient mice. Am J Physiol Gastrointest Liver Physiol 290: G109-119.
22. Katakura K, Lee J, Rachmilewitz D, Li G, Eckmann L, et al. (2005) Toll-like receptor 9-induced type 1 IFN protects mice from experimental colitis. J Clin Invest 115: 695-702.
23. Picornell Y, Mei L, Taylor K, Yang H, Targan S R, et al. (2007) TNFSF15 is an ethnic-specific IBD gene. Inflamm Bowel Dis 13: 1333-1338.
24. Michelsen K S, Thomas L S, Taylor K D, Yu Q T, Mei L, et al. (2009) IBD associated TL1A gene (TNFSF15) haplotypes determine increased expression of TL1A protein. PLoS One 4: e4719.
25. Vidrich A, Buzan J M, Barnes S. Reuter B K, Skaar K, et al. (2005) Altered epithelial cell lineage allocation and global expansion of the crypt epithelial stem cell population are associated with ileitis in SAMP1/YitFc mice. Am J Pathol 166: 1055-1067.
26. Kosiewicz M M, Nast C C, Krishnan A, Rivera-Nieves J, Moskaluk C A, et al (2001) Th1-type responses mediate spontaneous ileitis in a novel murine model of Crohn's disease. J Clin Invest 107: 695-702.
27. Shinoda M, Shin-Ya M, Naito Y, Kishida T, Ito R, et al. (2010) Early-stage blocking of Notch signaling inhibits the depletion of goblet-cells in dextran sodium sulfate-induced colitis in mice. J Gastroenterol 45: 608-617.
28. Kajino-Sakamoto R, Inagaki M, Lippert E, Akira S, Robine S. et al. (2008) Enterocyte-derived TAK1 signaling prevents epithelium apoptosis and the development of ileitis and colitis. J Immunol 181: 1143-1152.
29. Koon H W, Shih D, Karagiannides I, Zhao D, Fazelbhoy Z, et al. (2010) Substance P Modulates Chronic Inflammation-Induced Colonic Fibrosis. Am J Pathol 177: 2300-2309.
30. Di Sabatino A. Jackson C L, Pickard K M, Buckley M, Rovedatti L, et al. (2009) Transforming growth factor beta signalling and matrix metalloproteinases in the mucosa overlying Crohn's disease strictures. Gut 58: 777-789.
31. Simmons J G, Pucilowska J B, Keku T O, Lund P K (2002) IGF-I and TGF-beta1 have distinct effects on phenotype and proliferation of intestinal fibroblasts. Am J Physiol Gastrointest Liver Physiol 283: G809-818.
32. Hieshima K, Kawasaki Y, Hanamoto H, Nakayama T, Nagakubo D, et al. (2004) CC chemokine ligands 25 and 28 play essential roles in intestinal extravasation of IgA antibody-secreting cells, J Immunol 173: 3668-3675.
33. Reiss Y, Proudfoot A E, Power C A, Campbell J J, Butcher E C (2001) CC chemokine receptor (CCR)4 and the CCR10 ligand cutaneous T cell-attracting chemokine (CTACK) in lymphocyte trafficking to inflamed skin. J Exp Med 194:1541-1547.
34. Soler D, Humphreys T L, Spinola S M, Campbell J J (2003) CCR4 versus CCR10 in human cutaneous TH lymphocyte trafficking Blood 101: 1677-1682. 35. Wurbel M A, Malissen M, Guy-Grand D, Meffre E, Nussenzweig M C, et al. (2001) Mice lacking the CCR9 CC-chemokine receptor show a mild impairment of early T- and B-cell development and a reduction in T-cell receptor gammadelta(+) gut intraepithelial lymphocytes. Blood 98: 2626-2632.
36. Marsal J, Svensson M, Ericsson A, Iranpour A H, Carramolino L, et al. (2002) Involvement of CCL25 (TECK) in the generation of the murine small-intestinal CD8alpha alpha+CD3+ intraepithelial lymphocyte compartment. Eur J Immunol 32: 3488-3497.
37. Svensson M, Marsal J, Ericsson A, Carramolino L, Broden T, et al. (2002) CCL25 mediates the localization of recently activated CD8alphabeta(+) lymphocytes to the small-intestinal mucosa. J Clin Invest 110: 1113-1121.
38. Zabel B A, Agace W W, Campbell J J, Heath H M, Parent D, et al. (1999) Human G protein-coupled receptor GPR-9-6/CC chemokine receptor 9 is selectively expressed on intestinal homing T lymphocytes, mucosal lymphocytes, and thymocytes and is required tier thymus-expressed chemokine-mediated chemotaxis. J Exp Med 190: 1241-1256.
39. Kunkel E J, Campbell J J, Haraldsen G, Pan J, Boisvert J, et al. (2000) Lymphocyte CC chemokine receptor 9 and epithelial thymus-expressed chemokine (TECK) expression distinguish the small intestinal immune compartment: Epithelial expression of tissue-specific chemokines as an organizing principle in regional immunity. J Exp Med 192: 761-768.
40. Papadakis K A, Prehn J, Nelson V, Cheng L, Binder S W, et at. (2000) The role of thymus-expressed chemokine and its receptor CCR9 on lymphocytes in the regional specialization of the mucosal immune system. J Immunol 165: 5069-5076.
41. Targan S R, Feagan B G, Fedorak R N, Lashner B A, Panaccione ft, et al (2007) Natalizumab for the treatment of active Crohn's disease: results of the ENCORE Trial. Gastroenterology 132: 1672-1683.
42. Kang Y J, Kim W J, Bae H U, Kim D I, Park Y B, et al, (2005) Involvement of TL1A and DR3 in induction of pro-inflammatory cytokines and matrix metalloproteinase-9 in atherogenesis. Cytokine 29: 229-235.
43. McLaren J E, Calder C J, McSharry B P, Sexton K, Salter R C, et at. (2010) The TNF-like protein 1A-death receptor 3 pathway promotes macrophage foam cell formation in vitro. J immunol 184: 5827-5834.
44. Migone T S, Zhang J, Luo X, Zhuang L, Chen C, et al. (2002) TL1A is a TNFlike ligand for DR3 and TR6/DcR3 and functions as a T cell costimulator. Immunity 16: 479-492.
45. Biener-Ramanujan E, Gonsky R, Ko B, Targan SR (2010) Functional signaling of membrane-bound TL1A induces IFN-gamma expression. FEBS Lett 584: 2376-2380.
46. Zhumabekov T, Corbella P, Tolaini M, Kioussis D (1995) improved version of a human CD2 minigene based vector for T cell-specific expression in transgenic mice. J Immunol Methods 185: 133-140.
47. Brocker T, Riedinger M, Karjalainen K (1997) Targeted expression of major histocompatibility complex (MHC) class II molecules demonstrates that dendritic cells can induce negative but not positive selection of thymocytes in vivo. J Exp Med 185: 541-550.
48. Shaikh R B, Santee S. Granger S W, Butrovich K, Cheung T, et at. (2001) Constitutive expression of LIGHT on T-cells leads to lymphocyte activation, inflammation, and tissue destruction. J immunol 167: 6330-6337.
49. Wang J, Anders R A, Wu Q, Peng D, Cho J H, et al, (2004) Dysregulated LIGHT expression on T-cells mediates intestinal inflammation and contributes to IgA nephropathy. J Clin Invest 113: 826-835.
50. Ivanov I I, Frutos Rde L, Manel N, Yoshinaga K, Rifkin D B, et al. (2008) Specific microbiota direct the differentiation of IL-17-producing T-helper cells in the mucosa of the small intestine. Cell Host Microbe 4: 337-349.

51. Ivanov I I, Atarashi K, Manel N, Brodie E L, Shima T, et al. (2009) Induction of intestinal Th17 cells by segmented filamentous bacteria. Cell 139: 485-498.
52. Wu H J, Ivanov I I, Darce J, Hattori K, Shirna T, et at. (2010) Gut-residing segmented filamentous bacteria drive autoimmune arthritis via T helper 17 cells. Immunity 32: 815-827.
53. Peyrin-Biroulet L, Loftus E V, Jr., Colombel J F, Sandborn W J: The natural history of ad Crohn's disease in population-based cohorts, Am J Gastroenterol 2010, 105:289-297.
54. Genome-wide association study of 14,000 cases of seven common diseases and 3,00(shared controls, Nature 2007, 447:661-678.
55. Schreiber T H, Wolf D, Podack E R: The role of TNERSF25:TNFSF15 in disease and health? Adv Exp Med Biol 2011, 691:289-298.
56. Shih D Q, Michelsen K S, Barrett R J, Biener-Ramanujan E, Gonsky R, Zhang X, Targan S R: Insights into TL1A and IBD pathogenesis, Adv Exp Med Biol 2011, 691:279-288.
57. Shih D Q, Barrett R, Zhang X, Yeager N, Koon H W, Phaosawasdi P, Song Y, Ko B, Wong M H, Michelsen K S, Martins G, Pothoulakis C, Targan S R: Constitutive TL1A (TNFSF15) expression on lymphoid or myeloid cells leads to mild intestinal inflammation and fibrosis, PLoS One 2011, 6:e16090.
58. Jones G W, Stumhofer J S, Foster T, Twohig J P, Hertzog P, Topley N, Williams A S, Hunter C A, Jenkins B J, Wang E C, Jones S A: Naive and activated T cells display differential responsiveness to TL1A that affects Th17 generation, maintenance, and proliferation, Faseb J 2011, 25:409-419.
59. Ostanin D V, Pavlick K P, Bharwani S. D'Souza D, Furr K L, Brown C M, Grisham M B: T cell-induced inflammation of the small and large intestine in immunodeficient mice, Am J Physiol Gastrointest Liver Physiol 2006, 290:G109-119.
60. Koon H W, Shift D, Karagiannides I, Zhao D, Fazelbhoy Z, Hing T, Xu H, Lu B, Gerard N, Pothoulakis C: Substance P Modulates Chronic Inflammation-Induced Colonic Fibrosis, Am J Pathol 2010, 177:2300-2309.
61. Shih D Q, Kwan L Y, Chavez V, Cohavy O, Gonsky R, Chang E Y, Chang C, Elson C O, Targan S R: Microbial induction of inflammatory bowel disease associated gene TL1A (TNFSF15) in antigen presenting cells, Eur J Immunol 2009, 39:3239-3250.
62. Rachmilewitz D, Karmeli F, Shteingart S, Lee J, Takabayashi K, Raz E: Immunostimulatory oligonucleotides inhibit colonic proinflammatory cytokine production in ulcerative colitis, Inflamm Bowel Dis 2006, 12:339-345.
63. Koon H W, Shih D, Karagiannides I, Zhao D, Fazelbhoy Z, Hing T, Xu H, Lu B, Gerard N, Pothoulakis C: Substance P Modulates Chronic Inflammation-Induced Colonic Fibrosis, Am J Pathol 2010, 177:2300-2309.
64. Lawrance I C, Maxwell L, Doe W: Inflammation location, but not type, determines the increase in TGF-beta1 and IGF-1 expression and collagen deposition in IBD intestine, Inflamm Bowel Dis 2001, 7:16-26.
65. Zimmermann E M, Li L, Hou Y T, Mohapatra N K, Pucilowska J B: Insulin-like growth factor and insulin-like growth factor binding protein 5 in Crohn's disease, Am J Physiol Gastrointest Liver Physiol 2001, 280: G1022-1029.
66. Bamias G, Martin C. 3rd, Marini M, Hoang S, Mishina M, Ross W G, Sachedina M A, Friel C M, Mize J, Bickston S J, Pizarro T T, Wei P, Cominelli F: Expression, localization, and functional activity of TL1A, a novel Th1-polarizing cytokine in inflammatory bowel disease, J Immunol 2003, 171:4868-4874.
67. Migone T S, Zhang J, Luo X, Zhuang L, Chen C, Hu B, Hong J S, Perry J W, Chen S F, Zhou J X, Cho Y H, Ullrich S, Kanakaraj P, Carrell J, Boyd E, Olsen H S, Hu G, Pukac L, Liu D, Ni J, Kim S. Gentz R. Feng P, Moore P A, Ruben S M, Wei P: TL1A is a TNF-like ligand for DR3 and TR6/DcR3 and functions as a T cell costimulator, Immunity 2002, 16:479-492.
68. Ivanov, I I, Atarashi K, Manel N, Brodie E L, Shima T, Karaoz U, Wei D, Goldfarb K C, Santee C A, Lynch S V, Tanouc T, Imaoka A, Itoh K, Takeda K, Umesaki Y, Honda K, Littman DR: Induction of intestinal Th17 cells by segmented filamentous bacteria, Cell 2009, 139:485-498.
69. Ivanov, I I, Frutos Rde L, Mattel N, Yoshinaga K, Rifkin D B, Sartor R B, Finlay B B, Littman D R: Specific microbiota direct the differentiation of IL-17-producing T-helper cells in the mucosa of the small intestine, Cell Host Microbe 2008, 4:337-349.
70. Wu H J, Ivanov, I I, Darce J, Hattori K, Shima T, Umesaki Y, Littman D R, Benoist C, Mathis D: Gut-residing segmented filamentous bacteria drive autoimmune arthritis via T helper 17 cells, Immunity 2010, 12:815-877.
71. Kruglik G D, Neiman H L, Sparberg M, Nudelman E, Mintzer R A, Rogers L F: Urological complications of regional enteritis, Gastrointest Radiol 1977, 1:375-378.
72. Ruffolo C, Angriman I, Scarpa M, Polese L, Barollo M, Bertin M, Pagano D, D'Amico D F: Minimally invasive management of Crohn's disease complicated by ureteral stenosis, Surg Laparosc Endosc Percutan Tech 2004, 14:292-294.
73. D'Haens G R, Geboes K, Peeters M, Baert F, Penninckx F, Rutgeerts P: Early lesions of recurrent Crohn's disease caused by infusion of intestinal contents in excluded ileum, Gastroenterology 1998, 114262-767.
74. Dieleman L A, Ridwan B U, Tennyson G S, Beagley K W, Bucy R P, Elson C O: Dextran sulfate sodium-induced colitis occurs in severe combined immunodeficient mice, Gastroenterology 1994, 107:1643-1652.
75. Dickman L A, Pena A S, Meuwissen S G, van Rees E P: Role of animal models for the pathogenesis and treatment of inflammatory bowel disease. Scand J Gastroenterol Suppl 1997, 223:99-104.

The invention claimed is:

1. An animal model for a disease and/or condition, comprising:
   a transgenic rodent with a transgene overexpressing TL1A, wherein the TL1A overexpression is specific to an antigen presenting cell (APC) or dendritic cell (DC).

2. An animal model for a disease and/or condition, comprising:
   a transgenic rodent with a transgene overexpressing TL1A, wherein the TL1A overexpression is specific to a T-cell.

3. The animal model of claim 1, wherein the transgenic rodent has increased T-cell expression of one or more of the markers selected from the group consisting of CD4, CD8, CD86, CCR9, CCR10, FoxP3, TNF-α, IFN-γ, IL-10 and/or IL-17.

4. The animal model of claim 1, wherein the antigen presenting cell (APC) or dendritic cell (DC) expresses a fluorescent marker.

5. The animal model of claim 1, wherein the transgenic rodent expresses TL1A and GFP in about 35, 40, 45, 50, or 55% of all myeloid cells in a sample of myeloid cells isolated from the transgenic rodent.

6. An animal model for a disease and/or condition, comprising:
   a transgenic rodent with a transgene overexpressing TL1A, wherein the TL1A overexpression is specific to a cell type, and wherein the transgenic rodent expresses TL1A and GFP in about 80, 85, 90, 95, or 99% of all T-cells in a sample of T-cells isolated from the transgenic rodent.

7. The animal model of claim 1, wherein the transgenic rodent exhibits fibrostenosis, inflammation in the gastrointestinal (GI) tract, weight loss, and/or an increase in disease-activity index.

8. The animal model of claim 7, wherein the fibrostenosis is induced using dextrose sodium sulfate (DSS).

9. The animal model of claim 1, wherein the disease and/or condition is inflammatory bowel disease (IBD).

10. The animal model of claim 2, wherein the transgenic rodent has increased T-cell expression of one or more of the markers selected from the group consisting of: CD4, CD8, CD86, CCR9, CCR10, FoxP3, TNF-α, IFN-γ, IL-10 and/or IL-17.

11. The animal model of claim 2, wherein the T-cell expresses a fluorescent marker.

12. The animal model of claim 2, wherein the transgenic rodent exhibits fibrostenosis, inflammation in the gastrointestinal (GI) tract, weight loss, and/or an increase in disease-activity index.

13. The animal model of claim 12, wherein the fibrostenosis is induced using dextrose sodium sulfate (DSS).

14. The animal model of claim 2, wherein the disease and/or condition is inflammatory bowel disease (IBD).

15. The animal model of claim 6, wherein the transgenic rodent has increased T-cell expression of one or more of the markers selected from the group consisting of: CD4, CD8, CD86, CCR9, CCR10, FoxP3, TNF-α, IFN-γ, IL-10 and/or IL-17.

16. The animal model of claim 6, wherein the transgenic rodent exhibits fibrostenosis, inflammation in the gastrointestinal (GI) tract, weight loss, and/or an increase in disease-activity index.

17. The animal model of claim 16, wherein the fibrostenosis is induced using dextrose sodium sulfate (DSS).

18. The animal model of claim 6, wherein the disease and/or condition is inflammatory bowel disease (IBD).

* * * * *

UNITED STATES PATENT AND TRADEMARK OFFICE
CERTIFICATE OF CORRECTION

PATENT NO. : 8,766,034 B2
APPLICATION NO. : 13/240117
DATED : July 1, 2014
INVENTOR(S) : David Q. Shih et al.

Page 1 of 1

It is certified that error appears in the above-identified patent and that said Letters Patent is hereby corrected as shown below:

In the Title Page, page 1 left column, at the item (75) Inventors, should read as follows:
        (75) Inventors:  David Q. Shih, Los Angeles, CA (US);
                            Stephan R. Targan, Santa Monica, CA (US)

Signed and Sealed this
Twenty-fifth Day of August, 2015

Michelle K. Lee
*Director of the United States Patent and Trademark Office*